(12) United States Patent
Micalizio

(10) Patent No.: US 12,391,723 B2
(45) Date of Patent: Aug. 19, 2025

(54) STEROIDS AND METHODS OF MANUFACTURE

(71) Applicant: Trustees of Dartmouth College, Hanover, NH (US)

(72) Inventor: Glenn C. Micalizio, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 17/818,873

(22) Filed: Aug. 10, 2022

(65) Prior Publication Data

US 2023/0018615 A1    Jan. 19, 2023

Related U.S. Application Data

(62) Division of application No. 16/637,675, filed as application No. PCT/IB2018/056205 on Aug. 16, 2018, now Pat. No. 11,459,353.

(60) Provisional application No. 62/605,551, filed on Aug. 16, 2017.

(51) Int. Cl.
  *C07J 11/00*   (2006.01)
  *A61P 35/00*   (2006.01)
  *C07J 15/00*   (2006.01)
  *C07J 75/00*   (2006.01)

(52) U.S. Cl.
  CPC .............. *C07J 11/00* (2013.01); *A61P 35/00* (2018.01); *C07J 15/00* (2013.01); *C07J 75/005* (2013.01)

(58) Field of Classification Search
  CPC .................................. C07J 11/00; C07J 75/005
  See application file for complete search history.

(56) References Cited

U.S. PATENT DOCUMENTS

2008/0138391 A1   6/2008   Carrara et al.
2008/0299220 A1   12/2008  Tamarkin et al.

FOREIGN PATENT DOCUMENTS

WO   WO 2019/035061 A1   2/2019

OTHER PUBLICATIONS

SID 274720190. Pubchem. 4-Methylene-5-phenyl-6-(Trimethylsily1)-7-Abeta-Methyl-2,3,3a,4,7,7a-Hexahydro-1 H-Indene-2Alpha-ol (Dec. 18, 2015).
The United States Patent and Trademark Office, International Search Report in International Application No. PCT/IB2018/056205 (Jan. 18, 2019).
The United States Patent and Trademark Office, Written Opinion of the International Searching Authority in International Application No. PCT/IB2018/056205 (Jan. 18, 2019).
Kim et al., Nature Chemistry, 10(1): 70-77, 2018.
Wai et al., Organic Letters, 20: 6220-6224, 2018.
U.S. Appl. No. 16/637,675, filed Feb. 7, 2020, Pending.

*Primary Examiner* — Susanna Moore
(74) *Attorney, Agent, or Firm* — Neal, Gerber & Eisenberg LLP

(57) ABSTRACT

Methods for producing enantiodefined polycyclic compounds, particularly tetracyclic compounds, are provided. More particularly, synthetic methods for producing biologically active enantiodefined steroidal compositions of both natural ("nat-") and unnatural ("ent-") absolute stereochemistry are provided. An exemplary method for manufacturing a tetracyclic compound comprises a step of forming a hydrindane intermediate through coupling of a suitably functionalized enyne with a suitably functionalized alkyne and subsequently performing an intramolecular ring-closing reaction to form the tetracyclic compound. Steroidal compounds obtained by this method and methods of using such steroidal compounds in human and/or animal therapeutics and medicines are also provided.

21 Claims, 6 Drawing Sheets

16-hydroxyestratrienes are selectively active estrogens estra-1,3,5(10),6,8-penta-
ene-3,16α-diol[a]

ent-estra-1,3,5(10),6,8-
pentaene-3,16α-diol

[a] = United States Patent: US 7,109,360 B1 (Sep. 19, 2006)

STEROIDS AND METHODS OF MANUFACTURE

CROSS REFERENCE TO RELATED APPLICATION

This application is a divisional of U.S. patent application Ser. No. 16/637,675, which is a National Stage Entry of International Patent Application No. PCT/IB2018/056205, filed on Aug. 16, 2018, which claims the priority of U.S. Patent Application No. 62/605,551, filed on Aug. 16, 2017; the entire contents of each of the aforementioned applications is hereby incorporated by reference.

FEDERALLY SPONSORED RESEARCH OR DEVELOPMENT

This invention was made with government support under R01 GM080266 awarded by the National Institutes of Health. The government has certain rights in the invention.

FIELD OF THE INVENTION

The present disclosure relates to methods of producing enantiodefined polycyclic ring compounds through unique intermediates and synthesis strategies. More particularly, the present disclosure provides synthetic methods of producing biologically active enantiodefined steroidal compositions of both natural and unnatural ("ent-") absolute stereochemistry. The present disclosure also relates to methods of using active natural and ent-steroidal compositions prepared from this method as biologically active (e.g., therapeutic) components in compositions and/or directly as human and/or animal therapeutics and medicines. The present disclosure further relates to methods of producing and using natural and ent-steroids in chemical, pharmacological, and biological studies and research.

BACKGROUND OF THE INVENTION

Steroids, as a class of biomolecules, have been intensely studied since the first correct structural elucidation of a natural steroid and the subsequent synthesis of equilenin in 1932 and 1939, respectively. Tremendous scientific effort has been expended to better understand the biological and physiological roles played by the myriad of naturally occurring steroids as well as to isolate natural steroids and to synthetically or semi-synthetically produce steroids and steroidal derivatives. Efforts in this area established a scientific foundation that has delivered >100 FDA-approved steroidal agents as therapeutics, leading to their current status as arguably the most well-studied and successful class of natural product-inspired pharmaceuticals.

Early scientific breakthroughs that established the steroid pharmaceutical industry were based on semisynthetic methods of production, wherein, available naturally occurring steroids were subsequently chemically transformed into high-value therapeutic agents. One such example, of a semisynthetic production pathway is the Merck bile acid-to-cortisone process. (See, Pines, S. H., Org. Proc. Res. Dev., 8, 708-724 [2004]). The resultant cortisone acetate produced via the Merck process is functionally identical to naturally produced cortisone (17a,21-dihydroxypregn-4-ene-3,11,20-trione) resulting from steroidogenesis. As such, the Merck process-derived cortisone shares both the beneficial potent anti-inflammatory properties as well as the potential deleterious systemic effects from long term use as naturally produced cortisone (e.g., hyperglycemia, insulin resistance, diabetes mellitus, osteoporosis, anxiety, depression, amenorrhoea, cataracts, Cushing's syndrome and glaucoma, and immune system suppression). Similarly, the testosterone, estrone, estradiol, progesterone, and cortisone steroids, produced using the Marker degradation, a synthetic route developed by American chemist Russell Earl Marker, share the same beneficial biological activities and potential side-effects with their steroidogenic cognates. (See, Marker, R. E., et al., J. Am. Chem. Soc., 62, 2525-2532 [1940]; Pines, S. H., Org. Proc. Res. Dev., 8, 708-724 [2004]; and Renneberg, R., Biotechnol. J., 3, 449-451 [2008]). The Merck and Marker processes stand out as important semisynthetic routes to producing valuable medicinal products.

In addition to the aforementioned semisynthetic routes to steroid production, there are a number of examples of de novo synthetic pathways for producing synthetic steroids starting from non-steroidal materials, notably the Smith-Torgov synthesis of estranes and biomimetic cation-olefin cyclization processes, among others. Semi-syntheses, nevertheless, remains the primary means by which pharmaceutically relevant steroids are prepared.

The aforementioned, and other presently available synthetic and semisynthetic routes to steroid production are, in summation, often complex, inefficient, and/or wholly incapable of producing advantageous collections (i.e., libraries) of highly oxygenated/functionalized steroidal target compositions necessary for advancement through modern drug development. Steroids have had a transformative impact on medicine and society, playing vital roles as oral contraceptives, treatments for cancer (including anti-angiogenic agents), heart failure, inflammation, pain, and traumatic brain injuries, among others, and as import chemical precursors for numerous steroid derivatives. Despite these many advances, substantial barriers persist that greatly limit the types of steroidal compositions that can efficiently be prepared and explored as potential medicines and biological tools/probes.

While semisynthetic routes to steroids (those beginning with a readily available natural steroid) have been incredibly powerful, they are not suitable for producing non-naturally occurring "ent-steroids" (defined by an unnatural absolute stereochemistry of the tetracycle). This point deserves further consideration, as diligent advancement of the new methods related to steroid synthesis have overtime positioned steroidal compositions as a "privileged" class of molecules (i.e., pharmacophores) within the pharmaceutical industry. While pairs of enantiomers share identical physical properties, and in the case of steroids "drug-like" properties, it is surprising that 100% of currently FDA-approved steroidal drugs are of the natural ('nat') antipode. As compared to natural steroids ("nat-steroids"), synthetic ent-steroidal compositions have complementary three dimensional structures while offering similar "drug-like" properties. As a result synthetic ent-steroids are privileged natural product-inspired scaffolds of great potential therapeutic relevance, and are distinct compositions in comparison to their natural isomers. (See, Akwa, Y., et al., Proc. Natl. Acad. Sci. U.S.A., 98, 14033-14037 [2001]; Green, P. S., et al., Endocrinology, 142, 400-406 [2001]; Biellmann, J. F., Chem. Rev., 103, 2019-2033 [2003]; Covey, D. F., Steroids, 74(7):577-585 [2009]; and Petit, G. H., et al., Eur. Neuropsychopharmacol., 21, 211-215 [2011]). In summary, ent-steroids are an important class of privileged pharmaceutical drug-like molecules that presently cannot be fully leveraged in biological and pharmaceutical research efforts because these molecules are not readily available from natural sources and existing chemical synthesis pathways are inefficient and not flexible enough to produce diverse collections of steroids suitable for drug discovery and development.

A practical method for efficient and stereospecific production of ent-steroids would enable scientists and physicians to better exploit the as yet untapped potential of ent-steroids as useful tools and therapeutics. Accordingly, what is needed are efficient and step-economical (i.e., concise), flexible, convergent, and enantiospecific methods of synthesizing synthetic nat- and/or ent-steroids having varying stereochemistry and substitution, and/or suitability for subsequent functionalization processes (i.e., manipulation of functionality in each ring of the characteristic tetracyclic nucleus) at research and/or production scale.

SUMMARY OF THE INVENTION

The present disclosure relates to methods of producing enantiodefined polycyclic ring compounds. More particularly, the present disclosure provides synthetic methods of producing biologically active steroidal compositions of both natural and unnatural absolute stereochemistry (nat- and ent-).

The present disclosure also relates to enantiodefined tetracyclic compounds (e.g., steroidal tetracycles) obtainable by or accessible from the methods described herein.

The present disclosure also relates to methods of using tetracyclic compounds, including natural and ent-steroidal compounds that are accessible from this method, as biologically active (e.g., therapeutic) components in compositions and/or directly as human and/or animal therapeutics and medicines. The present disclosure further relates to methods of producing and using natural and ent-steroids in chemical, pharmacological, and biological studies and research.

The present disclosure relates to tetracyclic steroidal compounds having a structure corresponding to Formula (IA), Formula (IB), Formula (IC), or Formula (ID):

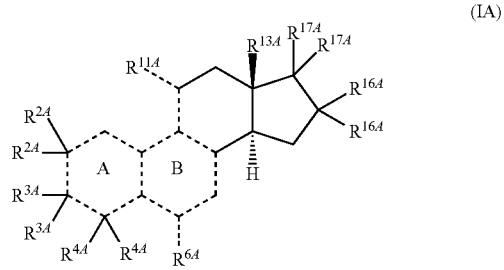

(IA)

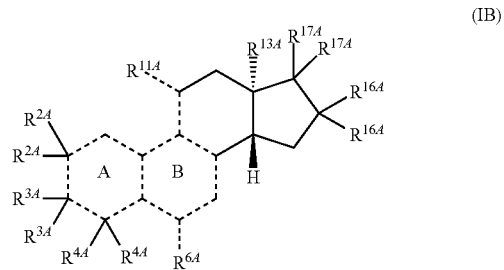

(IB)

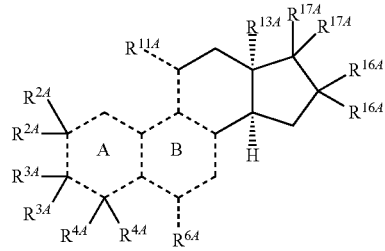

(IC)

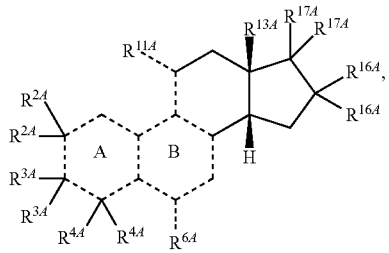

(ID)

wherein the variables (R groups) are defined herein.

The present disclosure also relates to methods for making such compounds, pharmaceutical compositions containing such compounds, and method for using such compounds and compositions to, for example, treat proliferative disease such as cancer or neurodegenerative diseases.

The present disclosure also relates to intermediate compounds useful for making tetracyclic steroidal compounds disclosed herein.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying Figures of which:

DETAILED DESCRIPTION OF THE INVENTION

Figure 1:
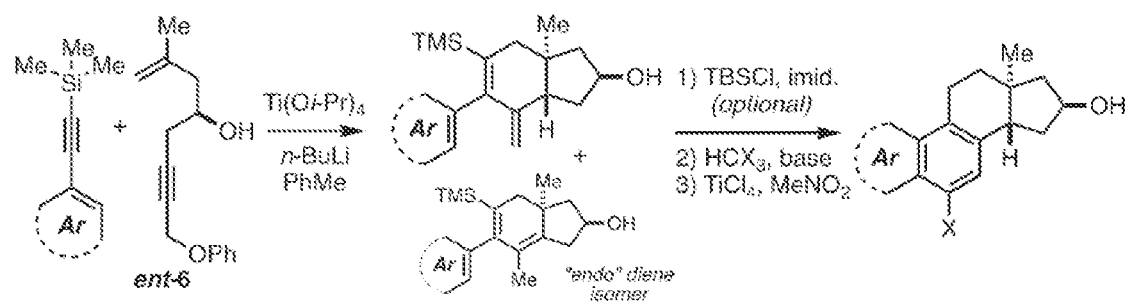
FIG. 1 shows a generalized chemical pathway useful for generating a wide range of steroidal systems in a concise and enantiospecific manner.

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Definitions

The terminology used herein is for the purpose of describing particular embodiments only and is not intended to be limiting of the invention. That the present disclosure may be more readily understood, select terms are defined below As used in the specification and the appended claims, unless specified to the contrary, the following terms have the meaning indicated:

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "agonist" as used herein refers to a compound having the ability to initiate or enhance a biological function and/or a target protein. Preferred agonists herein specifically interact with (e.g., bind to) their target(s).

The terms "antagonist" and "inhibitor" are used interchangeably, and they refer to a compound having the ability to inhibit a biological function and/or a target protein. Preferred antagonists/inhibitors herein specifically interact with (e.g., bind to) their target(s).

The term "antiangiogenic" refers to the ability to inhibit or impair the formation of blood vessels, including but not limited to inhibiting endothelial cell proliferation, endothelial cell migration, and capillary tube formation.

The term "cell proliferation" refers to a phenomenon by which the cell number has changed as a result of division. This term also encompasses cell growth by which the cell morphology has changed (e.g., increased in size) consistent with a proliferative signal.

The terms "co-administration," "administered in combination with," and their grammatical equivalents, encompass administration of two or more agents to a subject so that both agents and/or their metabolites are present in the subject at the same time. Co-administration includes simultaneous administration in separate compositions, administration at different times in separate compositions, or administration in a composition in which both agents are present. Co-administered agents may be in the same formulation. Co-administered agents may also be in different formulations.

The term "in vivo" refers to an event that takes place in a subject's body. The term "in vitro" refers to an event that takes places outside of a subject's body. For example, an in vitro assay encompasses any assay run outside of a subject assay. In vitro assays encompass cell-based assays in which cells alive or dead are employed. In vitro assays also encompass cell-free assays in which no intact cells are employed.

The term "neoplastic condition" refers to the presence of cells possessing abnormal growth characteristics, such as uncontrolled proliferation, immortality, metastatic potential, rapid growth and proliferation rate, perturbed oncogenic signaling, and certain characteristic morphological features. This includes but is not limited to the growth of benign or malignant cells (e.g., tumor cells), including such growth that correlates with overexpression of a tyrosine or serine/threonine kinase.

The term "pharmaceutically acceptable" is used adjectivally to mean that the modified noun is appropriate for use as a pharmaceutical product or as a part of a pharmaceutical product. The phrase "pharmaceutically acceptable" further denotes those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The term "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

The terms "pharmaceutically acceptable carrier" or "pharmaceutically acceptable excipient" include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the invention is contemplated. Supplementary active ingredients can also be incorporated into the compositions.

The terms "prevent", "preventing" and "prevention" (i) refer to a method for preventing the onset of a condition, disorder, or disease and/or the attendant symptoms thereof or barring a subject from acquiring a condition, disorder, or disease and/or (ii) refer to an approach for obtaining beneficial or desired results including but not limited to prophylactic benefit. As used herein, "prevent", "preventing" and "prevention" also include delaying the onset of a condition, disorder, or disease and/or the attendant symptoms thereof and reducing a subject's risk of acquiring a condition, disorder, or disease. For prophylactic benefit, the compositions may be administered to a patient at risk of developing a particular disease, or to a patient reporting one or more of the physiological symptoms of a disease, even though a diagnosis of this disease may not have been made.

The term "prophylactic effect" includes delaying or eliminating the appearance of a disease or condition, delaying or eliminating the onset of symptoms of a disease or condition, slowing, halting, or reversing the progression of a disease or condition, or any combination thereof.

The term "steroid" refers to a compound having carbon atoms arranged in a 4-ring structure. (See, e.g., J. American Chemical Society, 82:5525-5581 (1960); and, Pure and Applied Chemistry, 31:285-322 (1972)).

The term "subject" refers to an animal, such as a mammal, for example a human or other primate. The methods described herein can be useful in both human therapeutics, pre-clinical, and veterinary applications. In some embodiments, the subject is a mammal, and in some embodiments, the subject is human.

A "sub-therapeutic amount" of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

A "synergistically effective" therapeutic amount or "synergistically effective" amount of an agent or therapy is an amount which, when combined with an effective or sub-therapeutic amount of another agent or therapy, produces a greater effect than when either of the two agents are used alone. In some embodiments, a synergistically effective therapeutic amount of an agent or therapy produces a greater effect when used in combination than the additive effects of each of the two agents or therapies when used alone. The term "greater effect" encompasses not only a reduction in symptoms of the disorder to be treated, but also an improved side effect profile, improved tolerability, improved patient compliance, improved efficacy, or any other improved clinical outcome.

The term "therapeutic effect" encompasses a therapeutic benefit and/or a prophylactic benefit as described herein.

The term "therapeutically effective amount" refers to a sufficient amount of the compound to treat a condition, disorder, or disease, at a reasonable benefit/risk ratio applicable to any medical treatment. When used in a medical treatment, a therapeutically effective amount of one of the present compounds can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers.

The terms "treatment", "treating", "palliating" and "ameliorating" are used interchangeably as context indicates. In particular, these terms (i) refer to a method for alleviating or abrogating a condition, disorder, or disease and/or the attendant symptoms thereof and/or (ii) refer to an approach for obtaining beneficial or desired results including but not limited to therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

The term "hydrocarbyl" or "hydrocarbon" refers to moieties consisting exclusively of the elements carbon and hydrogen, in a straight or branched chain, or alternatively a cyclic structure, which may optionally be substituted with other hydrocarbon, halo (e.g., chlorine, fluorine, bromine) or hetero (e.g., oxygen, sulfur) substituents. These moieties include alkyl, alkenyl, alkynyl and aryl moieties as well as alkyl, alkenyl, alkynyl and aryl moieties substituted with other aliphatic or cyclic hydrocarbon groups such as, for example, alkaryl, alkenaryl and alkynaryl. In some instances, the number of carbon atoms in a hydrocarbon substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms.

The term "substituted" is intended to indicate that one or more hydrogens on the substituent indicated in the expression using "substituted" is replaced with another group(s), provided that the indicated atom's normal valency is not exceeded, and that the substitution results in a stable compound. If a particular substituent is described as being "substituted", it means that there are one or more substituents other than hydrogen attached to that particular substituent. Thus, for example, a substituted alkyl is an alkyl in which at least one non-hydrogen substituent is in the place of a hydrogen atom on the alkyl. If a particular substituent is described as being "optionally substituted", that particular substituent may be either (1) not substituted or (2) substituted. Combinations of variables or substituents are permissible only if such combinations result in stable compounds. Stable compounds are compounds that can be isolated from a reaction mixture.

"Acyl" refers an "R" group appended to the parent molecular moiety through a carbonyl group and includes the groups (alkyl)-C(O)—, (aryl)-C(O)—, (heteroaryl)-C(O)—, (heteroalkyl)-C(O)—, and (heterocycloalkyl)-C(O)—, wherein the group is attached to the parent structure through the carbonyl functionality. In some embodiments, it is a $C_1$-$C_{10}$ acyl radical which refers to the total number of chain or ring atoms of the alkyl, aryl, heteroaryl or heterocycloalkyl portion of the acyl group plus the carbonyl carbon of acyl, i.e., three other ring or chain atoms plus carbonyl. If the R radical is heteroaryl or heterocycloalkyl, the hetero ring or chain atoms contribute to the total number of chain or ring atoms.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group may consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_4$ alkyl group. Typical alkyl groups include, but are in no way limited to, methyl, ethyl, propyl, isopropyl, n-butyl, iso-butyl, sec-butyl, tert-butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

The term "lower alkyl" or "$C_1$-$C_6$-alkyl" means a straight or branched hydrocarbon chain containing from 1 to 6 carbon atoms.

The terms "alkene" or "alkenyl" refer to a straight or branched hydrocarbon chain radical group consisting solely of carbon and hydrogen atoms, containing at least one carbon-carbon double bond, and having from two to ten carbon atoms (i.e., $C_2$-$C_{10}$ alkenyl). In certain embodiments, an alkenyl comprises two to eight carbon atoms. In other embodiments, an alkenyl comprises two to five carbon atoms (e.g., $C_2$-$C_5$ alkenyl). The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like.

The term "alkyne" or "alkynyl" refers to a straight or branched hydrocarbon chain radical group consisting solely of carbon and hydrogen atoms, containing at least one carbon-carbon triple bond, having from two to ten carbon atoms (i.e., $C_2$-$C_{10}$ alkynyl). In other embodiments, an alkynyl has two to five carbon atoms (e.g., $C_2$-$C_5$ alkynyl). The alkynyl is attached to the rest of the molecule by a single bond, for example, ethynyl, propynyl, butynyl, pentynyl, hexynyl, and the like.

The term "alkoxy" refers to the group —O-alkyl, including from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkyl, is an alkyl group which encompasses both straight and branched chain alkyls of from 1 to 4 carbon atoms.

"Amide" or "amido" refers to a chemical moiety with formula —C(O)N(R)$_2$ or —NHC(O)R, where R is selected from the group consisting of hydrogen, alkyl, cycloalkyl, aryl, heteroaryl (bonded through a ring carbon) and heteroalicyclic (bonded through a ring carbon), each of which moiety may itself be optionally substituted. In some embodiments it is a $C_1$-$C_4$ amido or amide radical, which includes the amide carbonyl in the total number of carbons in the radical. The $R^2$ of —N(R)$_2$ of the amide may optionally be taken together with the nitrogen to which it is attached to form a 4-, 5-, 6-, or 7-membered ring. An amide may be an amino acid or a peptide molecule attached to a compound of Formula (I), thereby forming a prodrug. Any amine, hydroxy, or carboxyl side chain on the compounds described herein can be amidified. The procedures and specific groups to make such amides are known to those of skill in the art and can readily be found in reference sources such as Greene and Wuts, Protective Groups in Organic Synthesis, 3rd Ed., John Wiley & Sons, New York, N.Y., 1999, which is incorporated herein by reference in its entirety.

"Amino" or "amine" refers to a —N(R$^a$)$_2$ radical group, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N(R$^a$)$_2$ group has two R$^a$ other than hydrogen they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl.

The terms "aromatic" or "aryl" refer to an aromatic radical with six to fourteen ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. The term includes monocyclic or fused-ring polycyclic (i.e., rings which share adjacent pairs of ring atoms) groups. In the case of a polycyclic aryl, only one ring of the polycyclic system is required to be aromatic while the remaining ring(s) may be saturated, partially saturated or unsaturated. Representative examples of aryl include, but are not limited to, phenyl, naphthalenyl, indenyl, indanyl, and tetrahydronapthyl.

The terms "aryl-alkyl", "arylalkyl" and "aralkyl" refers to an aryl group, as defined herein, appended to the parent molecular moiety through an alkylene group, as defined herein. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxyphenyl)butyl, and 10-phenyldecyl. Either portion of the moiety is unsubstituted or substituted.

"Cycloalkyl" refers to a monocyclic or polycyclic radical that contains only carbon and hydrogen, and may be saturated, or partially unsaturated, and contains from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include, but are not limited to, cyclopropyl, cyclobutyl, cyclopentyl, cyclopentenyl, cyclohexyl, cyclohexenyl, cycloseptyl, cyclooctyl, cyclononyl, and cyclodecyl. A cycloalkyl may alternatively be polycyclic or contain more than one ring. Examples of polycyclic cycloalkyls include bridged, fused, and spirocyclic carbocyclyls (e.g., norbornyl).

The term "bicycloalkyl" refers to a structure consisting of two cycloalkyl moieties, unsubstituted or substituted, that have two or more atoms in common. If the cycloalkyl moieties have exactly two atoms in common they are said to be "fused". Examples include, but are not limited to, bicyclo [3.1.0]hexyl, perhydronaphthyl, and the like. If the cycloalkyl moieties have more than two atoms in common they are said to be "bridged." Examples include, but are not limited to, bicyclo[3.2.1]heptyl ("norbornyl"), bicyclo[2.2.2]octyl, and the like.

The term "cycloalkenyl" refers to a cyclic aliphatic 3 to 8 membered ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl, and the like.

The term "halo" or "halogen" refers to fluoro, chloro, bromo, or iodo.

The term "haloalkyl" refers to an alkyl group substituted with one or more halo groups, for example chloromethyl, 2-fluoroethyl, 2-bromoethyl, 3-iodopropyl, 2,2,2-trifluoroethyl, trifluoromethyl, difluoromethyl, pentafluoroethyl, 2-chloro-3-fluoropentyl, and trifluoropropyl such as 3,3,3-trifluoropropyl, perfluoropropyl, 8-chlorononyl, and the like.

The term "haloalkenyl" refers to an alkenyl group substituted with one or more halo groups (one or more hydrogen atoms of the alkenyl group are replaced by a halogen atom).

The term "haloalkynyl" refers to an alkynyl group substituted with one or more independent halo groups (one or more hydrogen atoms of the alkynyl group are replaced by a halogen atom).

The term "haloalkoxy" refers to an alkoxy group substituted with one or more halo groups, for example chloromethoxy, trifluoromethoxy, difluoromethoxy, perfluoroisobutoxy, and the like.

The term "heteroatom" or "ring heteroatom" includes oxygen (O), nitrogen (N), sulfur (S), phosphorus (P), and silicon (Si) and, preferably oxygen (O), nitrogen (N), or sulfur (S).

The terms "heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g., $C_1$-$C_4$ heteroalkyl which refers to the chain length in total, which in this example is 1 to 4 atoms long or a 5- to 14-membered heteroaryl ring which refers to the number of ring atoms, which in this example is 5 to 14 ring atoms. For example, a —$CH_2OCH_2CH_3$ radical is referred to as a "$C_4$" heteroalkyl, which includes the heteroatom center in the atom chain length description. Connection to the rest of the molecule may be through either a heteroatom or a carbon in the heteroalkyl chain.

The terms "heteroaryl" or "heteroaromatic" refer to a 5- to 18-membered aromatic radical (e.g., 5- to 14-membered heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range; e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. A heteroaryl may be monocyclic or polycyclic (i.e., may contain more than one ring). In the case of a polycyclic heteroaryl, only one ring of the polycyclic system is required to be aromatic while the remaining ring(s) may be saturated, partially saturated or unsaturated. The polycyclic heteroaryl group may be fused or non-fused. An N-containing "heteroaromatic" or "heteroaryl" moiety refers to an aromatic group in which at least one of the skeletal atoms of the ring is a nitrogen atom. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl).

The terms "heteroarylalkyl", "heteroarylalkyl", "heteroaryl-alkyl", "heteroaryl-alkyl", "hetaralkyl" and "heteroaralkyl" are used to describe a heteroaryl group, as defined herein, appended to the parent molecular moiety through an alkylene group, as defined herein. The alkylene chain can be branched or straight chain forming a linking portion of the heteroaralkyl moiety with the terminal heteroaryl portion, as defined above, for example 3-furylmethyl, thenyl, furfuryl, and the like. Either portion of the moiety is unsubstituted or substituted.

The term "heterocycloalkyl" refers to a stable 3- to 18-membered non-aromatic ring radical that comprises at least one ring heteroatom selected from nitrogen, oxygen and sulfur. Whenever it appears herein, a numerical range such as "3 to 18" refers to each integer in the given range; e.g., "3 to 18 ring atoms" means that the heterocycloalkyl group may consist of 3 ring atoms, 4 ring atoms, etc., up to and including 18 ring atoms. In some embodiments, it is a 5- to 10-membered heterocycloalkyl. In some embodiments, it is a 4- to 10-membered heterocycloalkyl. In some embodiments, it is a 3- to 10-membered heterocycloalkyl. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]

dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxothiomorpholinyl, and 1,1-dioxothiomorpholinyl. "Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

The term "oxo" refers to an oxygen that is double bonded to a carbon atom. One in the art understands that an "oxo" requires a second bond from the atom to which the oxo is attached. Accordingly, it is understood that oxo cannot be substituted onto an aryl or heteroaryl ring, unless it forms part of the aromatic system as a tautomer.

Unless otherwise defined herein, scientific and technical terms used in connection with the present disclosure shall have the meanings that are commonly understood by those of ordinary skill in the art. The meaning and scope of the terms should be clear, however, in the event of any latent ambiguity, definitions provided herein take precedent over any dictionary or extrinsic definition.

Further, unless otherwise required by context, singular terms shall include pluralities and plural terms shall include the singular. For example, the singular forms "a", "an" and "the" are intended to include the plural forms as well, unless the context clearly indicates otherwise.

In this application, the use of "or" means "and/or" unless stated otherwise. Furthermore, the use of the term "including", as well as other forms, such as "includes" and "included", is not limiting. Furthermore, to the extent that the terms "including", "includes", "having", "has", "with", or variants thereof are used in either the detailed description and/or the claims, such terms are intended to be inclusive in a manner similar to the term "comprising."

In certain aspects, the present disclosure relates to compounds (and methods of making such compounds, compositions comprising such compounds, and methods of using such compounds) comprising a general tetracyclic steroidal (A, B, C, D) ring structure, as follows:

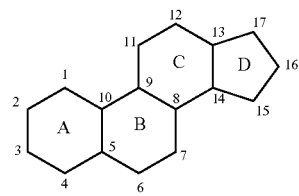

The numbering convention throughout the present disclosure is in accordance with numbered structure above.

In reference to the general tetracyclic steroidal (A, B, C, D) ring structure, it will be well appreciated that in view of the disclosure contained herein as well as the teachings in the relevant fields of art, the compounds, compositions, and methods of the present disclosure are not limited to any particular respective constituent (R) group(s) at the various numbered carbon atoms in the general tetracyclic steroidal (A, B, C, D) ring structure. Moreover, it will be well appreciated that in view of the disclosure contained herein as well as the teachings in the relevant fields of art, the compounds, compositions, and methods of the present disclosure may comprise ones in which the A ring of the general tetracyclic steroidal (A, B, C, D) ring structure can be saturated, partially unsaturated, or completely unsaturated; likewise, the B ring of the general tetracyclic steroidal (A, B, C, D) ring structure can be saturated, partially unsaturated, or completely unsaturated.

In some exemplary embodiments of the general tetracyclic steroidal (A, B, C, D) ring structure, each numbered carbon atom contains one or more substituents (as the rules of valency allow), wherein each substituent is independently selected from the group consisting of hydrogen; $C_1$-$C_4$ alkyl; $C_2$-$C_4$ alkenyl; $C_2$-$C_4$ alkynyl; —$CF_3$; halo; =O; —OH; —O-($C_1$-$C_4$-alkyl); —$OCH_2F$; —$OCHF_2$; —$OCF_3$; —OC(O)-($C_1$-$C_4$-alkyl); —OC(O)-($C_1$-$C_4$-alkyl); —OC(O)NH-($C_1$-$C_4$-alkyl); —OC(O)N($C_1$-$C_4$-alkyl)$_2$; —OC(S)NH-($C_1$-$C_4$-alkyl); —OC(S)N($C_1$-$C_4$-alkyl)$_2$; —SH; —S-($C_1$-$C_4$-alkyl); —S(O)-($C_1$-$C_4$-alkyl); —S(O)$_2$-($C_1$-$C_4$-alkyl); —SC(O)-($C_1$-$C_4$-alkyl); —SC(O)O-($C_1$-$C_4$-alkyl); —$NH_2$; —N(H)-($C_1$-$C_4$-alkyl); —N($C_1$-$C_4$-alkyl)$_2$; —N(H)C(O)-($C_1$-$C_4$-alkyl); —N($CH_3$)C(O)-($C_1$-$C_4$-alkyl); —N(H)C(O)—$CF_3$; —N($CH_3$)C(O)—$CF_3$; —N(H)C(S)-($C_1$-$C_4$-alkyl); —N($CH_3$)C(S)-($C_1$-$C_4$-alkyl); —N(H)S(O)$_2$-($C_1$-$C_4$-alkyl); —N(H)C(O)$NH_2$; —N(H)C(O)NH-($C_1$-$C_4$-alkyl); —N($CH_3$)C(O)NH-($C_1$-$C_4$-alkyl); —N(H)C(O)N($C_1$-$C_4$-alkyl)$_2$; —N($CH_3$)C(O)N($C_1$-$C_4$-alkyl)$_2$; —N(H)S(O)$_2$$NH_2$; —N(H)S(O)$_2$NH-($C_1$-$C_4$-alkyl); —N($CH_3$)S(O)$_2$NH-($C_1$-$C_4$-alkyl); —N(H)S(O)$_2$N($C_1$-$C_4$-alkyl)$_2$; —N($CH_3$)S(O)$_2$N($C_1$-$C_4$-alkyl)$_2$; —N(H)C(O)O-($C_1$-$C_4$-alkyl); —N($CH_3$)C(O)O-($C_1$-$C_4$-alkyl); —N(H)S(O)$_2$O-($C_1$-$C_4$-alkyl); —N($CH_3$)S(O)$_2$O-($C_1$-$C_4$-alkyl); —N($CH_3$)C(S)NH-($C_1$-$C_4$-alkyl); —N($CH_3$)C(S)N($C_1$-$C_4$-alkyl)$_2$; —N($CH_3$)C(S)O-($C_1$-$C_4$-alkyl); —N(H)C(S)$NH_2$; —$NO_2$; —$CO_2H$; —$CO_2$-($C_1$-$C_4$-alkyl); —C(O)N(H)OH; —C(O)N($CH_3$)OH; —C(O)N($CH_3$)OH; —C(O)N($CH_3$)O-($C_1$-$C_4$-alkyl); —C(O)N(H)-($C_1$-$C_4$-alkyl); —C(O)N($C_1$-$C_4$-alkyl)$_2$; —C(S)N(H)-($C_1$-$C_4$-alkyl); —C(S)N($C_1$-$C_4$-alkyl)$_2$; —C(NH)N(H)-($C_1$-$C_4$-alkyl); —C(NH)N($C_1$-$C_4$-alkyl)$_2$; —C($NCH_3$)N(H)-($C_1$-$C_4$-alkyl); —C($NCH_3$)N($C_1$-$C_4$-alkyl)$_2$; —C(O)-($C_1$-$C_4$-alkyl); —C(NH)-($C_1$-$C_4$-alkyl); —C($NCH_3$)-($C_1$-$C_4$-alkyl); —C(NOH)-($C_1$-$C_4$-alkyl); —C($NOCH_3$)-($C_1$-$C_4$-alkyl); —CN; —CHO; —$CH_2OH$; —$CH_2O$-($C_1$-$C_4$-alkyl); —$CH_2NH_2$; —$CH_2N(H)$-($C_1$-$C_4$-alkyl); —$CH_2N(C_1$-$C_4$-alkyl)$_2$; $C_6$-$C_{14}$-aryl; 5- to 14-membered heteroaryl; $C_3$-$C_{14}$-cycloalkyl; and 5- to 14-membered heterocyclyl.

In certain embodiments, unless otherwise stated or indicated by context, a substituent of the general tetracyclic steroidal (A, B, C, D) ring structure, such as an alkyl, alkenyl, alkynyl, cycloalkyl, aryl, heteroalkyl, heteroalkenyl, heteroalkynyl, heterocycloalkyl, or heteroaryl, is optionally substituted with one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(NR$^a$)N($R^a$)$_2$, —N($R^a$)S(O)$_t$$R^a$ (where t is 1 or 2), —S(O)$_t$O$R^a$ (where t is 1 or 2), —S(O)$_t$N ($R^a$)$_2$ (where t is 1 or 2), or —$PO_3$($R^a$)$_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

It is to be noted that the present disclosure encompasses a number of compounds having one or more chiral centers therein. Generally speaking, therefore, it is to be understood that the configuration at one or more of these chiral centers may change without departing from the scope of the intended invention; that is, it is to be understood that the present disclosure extends to compounds specifically or generally described herein as well as all related diastereomers and enantiomers.

In certain aspects, the present disclosure provides methods for synthetic production of tetracyclic compositions comprising nat-as well ent-steroidal core chemical structures.

In certain embodiments, a group of the compositions of the present disclosure comprise the nat-steroidal structure of Formula (nat) or the ent-steroidal structure of Formula (ent):

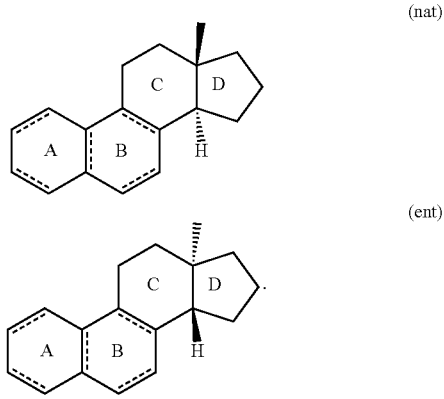

B. Synthetic Methods and Intermediate Compounds

In one aspect, the present disclosure provides a method for manufacturing a tetracyclic compound, such as a compound having the general tetracyclic steroidal (A, B, C, D) ring structure described herein.

In certain embodiments, the method comprises a step of forming a hydrindane of Formula (Ei) as an intermediate through coupling of a suitably functionalized enyne (Ci) with a suitably functionalized alkyne (Di). Scheme 3b depicts an exemplary reaction for forming the intermediate hydrindane of Formula (Ei).

Scheme 3b Formation of intermediate hydrindane (Ei)

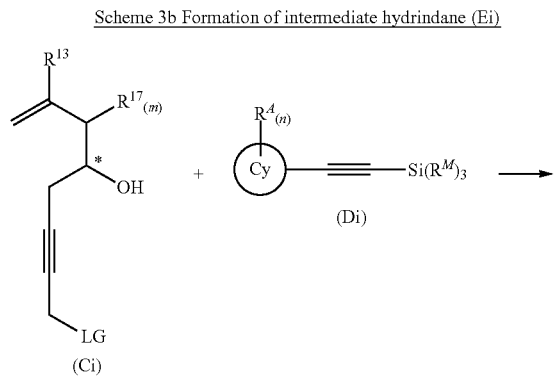

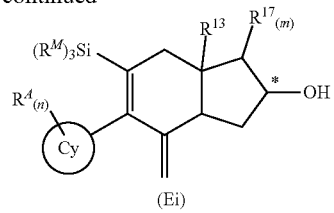

In Scheme 3b, a compound of Formula Ci is reacted with a compound of Formula Di to give a hydrindane of Formula Ei.

With respect to a compound of Formula Ci (and, where applicable, the product of the reaction, a hydrindane of Formula Ei), LG is a leaving group; each $R^{17}$ is independently selected from the group consisting of hydrogen, $C_{1-10}$-alkyl, $C_{2-10}$-alkenyl, $C_{2-10}$-alkynyl, $C_{1-10}$-haloalkyl, and halogen, or two $R^{17A}$ together form an oxo; and m is an integer selected from 0, 1, and 2; $R^{13}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy; wherein any $C_{3-8}$-cycloalkyl, 3- to 10-membered heterocycloalkyl, $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy. Exemplary leaving groups include, but are not limited to, halogen, —O—$Ar^1$, where $Ar^1$ is a substituted or unsubstituted $C_{6-10}$-aryl or 5- to 10-membered heteroaryl, in particular O-phenyl, and —$OSO_2R^{1a}$, wherein $R^{1a}$ is aryl, such as p-tolyl or phenyl; alkyl such as methyl or ethyl; fluoroalkyl such as trifluoromethyl, perfluorobutyl ($C_4F_9$), perfluoropentyl, perfluorohexyl, and perfluorooctyl; -fluoroalkyl-O-fluoroalkyl such as perfluoroethoxyethyl; —$N(alkyl)_2$; fluoro; or imidazolyl.

With respect to a compound of Formula Di (and the product of the reaction, a hydrindane of Formula Ei), Cy is $C_{3-8}$-cycloalkyl, 3- to 10-membered heterocycloalkyl, $C_{6-10}$-aryl, or 5- to 10-membered heteroaryl; each $R^M$ is independently selected from the group consisting of hydrogen, $C_{1-6}$-alkyl, trimethylsilyl, $C_{6-10}$-aryl, 5- to 10-membered heteroaryl, arylalkyl, and —$OR^{MX}$, wherein $R^{MX}$ is hydrogen, $C_{1-6}$-alkyl, or $C_{6-10}$-aryl; $R^A$ is selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, or two $R^A$ together form an oxo, wherein $R^{AX}$ is $C_{1-6}$-alkyl, $C_{2-10}$-alkenyl, $C_{2-10}$-alkynyl, $C_{1-10}$-haloalkyl, —$C(O)$-$C_{1-10}$-alkyl, —$C(O)$-$C_{6-10}$-aryl, —$C(O)$-heteroaryl, —$S(O)_2R^{Z1}$, $C_{6-10}$-aryl, or 5- to 10-membered heteroaryl, $R^{AY}$ is hydrogen, $C_{1-6}$-alkyl, $C_{2-10}$-alkenyl, $C_{2-10}$-alkynyl, $C_{1-10}$-haloalkyl, —$C(O)$-$C_{1-10}$-alkyl, —$C(O)$-$C_{6-10}$-aryl, —$C(O)$-heteroaryl, $C_{6-10}$-aryl, or 5- to 10-membered heteroaryl, wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy; and n is an integer selected from the group consisting of 0, 1, 2, 3, 4, 5, 6, 7, 8, 9, and 10; wherein any $C_{3-8}$-cycloalkyl, 3- to 10-membered heterocycloalkyl, $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In certain embodiments, the method further comprises a step (e.g., step (b)) of treating the hydrindane of Formula Ei to install a C6 carbon and provide a reactive intermediate for B-ring formation.

In certain embodiments, the method further comprises a step (e.g., step (c)) of performing an intramolecular ring-closing reaction to form the tetracyclic compound.

In certain embodiments, step (b) comprises cyclopropanation of the compound of Formula Ei to form a compound of Formula (Fi):

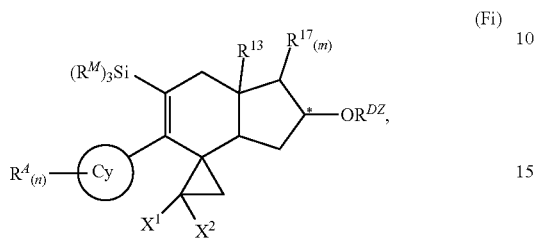

wherein $X^1$ and $X^2$ are independently selected from the group consisting of hydrogen, $C_{1-10}$-alkyl, $C_{2-10}$-alkenyl, $C_{2-10}$-alkynyl, $C_{1-10}$-haloalkyl, halogen, oxygen, —$OR^{BX}$, —$SR^{BY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl; and $R^{DX}$ is hydrogen or an oxygen protecting group. In some such embodiments, the cyclopropanation reaction occurs in an organic solvent, such as a halogenated organic solvent (e.g., $CHBr_3$). In some such embodiments, the cyclopropanation reaction occurs in the presence of a base, such as an alkali metal hydroxide (e.g., KOH). In some such embodiments, the cyclopropanation reaction occurs in the presence of a phase transfer catalyst, such as a quaternary ammonium salt, particularly trialkylbenzyl and tetraalkyl ammonium halides (e.g., benzyltriethylammonium chloride). In certain embodiments, $X^1$ is halogen, preferably bromo. In certain embodiments, $X^2$ is halogen, preferably bromo. In some such embodiments, $X^1$ and $X^2$ are both halogen. In some such embodiments, $X^1$ and $X^2$ are both bromo. In certain embodiments, $R^{DZ}$ is hydrogen. In certain embodiments, $R^{DZ}$ is an oxygen protecting group. Exemplary oxygen protecting groups include, but are not limited to, methyl, tert-butyloxycarbonyl (BOC), methoxymethyl (MOM), tert-butyldimethylsilyl (TBS), tert-butyldiphenylsilyl (TBDPS), and tribenzylsilyl. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference. In some such embodiments, higher yields may be encountered if protection of the secondary alcohol (at C16) is conducted prior to cyclopropanation.

In certain embodiments, step (b) further comprises treatment of the compound of Formula Fi with an acid, such as $TiCl_4$, $SnCl_4$, $BF_3OEt_2$, preferably $TiCl_4$, in an organic solvent, such as dichloromethane, chlorobenzene, ethylenechloride, 1,2-dichlorobenzene, nitromethane, tetrachlorethane, or mixtures thereof, preferably nitromethane, optionally in the presence of a protic additive (i.e. methanol, ethanol, isopropanol). In certain embodiments, the reaction occurs under an inert atmosphere, such as $N_2$.

In certain embodiments, step (b) comprises an intramolecular Friedel-Crafts alkylation reaction.

In certain embodiments, the method comprises a step of forming the compound of Formula (Ci). Schemes 3a and 3a' depict exemplary reactions for forming a the compound of Formula (Ci).

Scheme 3a and 3a' Formation of a compound of Formula (Ci)

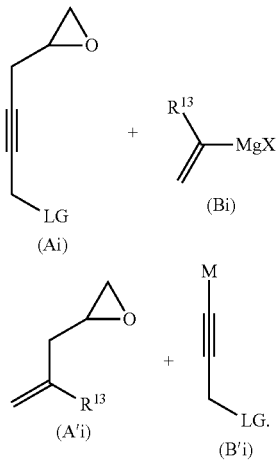

In Scheme 3a, a compound of Formula (Ai) is reacted with a compound of Formula (Bi) to give a compound of Formula (Ci).

In Scheme 3a', a compound of Formula (A'i) is reacted with a compound of Formula (B'i) to give a compound of Formula (C'i).

With respect to a compound of Formula (Ai) (and the product of the reaction, a compound of Formula (Ci)), LG is a leaving group. Exemplary leaving groups include, but are not limited to, halogen, —O—$Ar^1$, where $Ar^1$ is a substituted or unsubstituted $C_{6-10}$-aryl or 5- to 10-membered heteroaryl, in particular —O-phenyl, and —$OSO_2R^{1a}$, wherein $R^{1a}$ is aryl, such as p-tolyl or phenyl; alkyl such as methyl or ethyl; fluoroalkyl such as trifluoromethyl, perfluorobutyl ($C_4F_9$), perfluoropentyl, perfluorohexyl, and perfluorooctyl; -fluoroalkyl-O-fluoroalkyl such as perfluoroethoxyethyl; —N(alkyl)$_2$; fluoro; or imidazolyl. In certain embodiments, LG is —O-phenyl.

With respect to compound of Formula (Bi), X is a halogen or pseudohalogen. Exemplary psuedohalogens include, but are not limited to, cyano (—CN) and thiocyanate (—SCN). In certain embodiments, X is halogen. In certain particular embodiments, X is bromo.

With respect to a compound of Formula (B'i) (and, where applicable, the product of the reaction, a compound of Formula (Ci)), LG is a leaving group and M is a metal, such as Li, Na, K, and preferably Li.

In one aspect the present disclosure includes a method for manufacturing a C18 steroid compound of Formula (II) and, preferably, a compound of Formula (IIA):

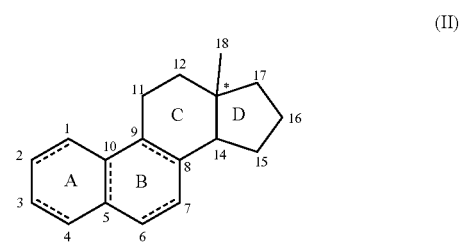

-continued

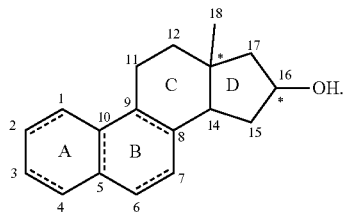
(IIA)

With respect to a compound of Formula (II) or Formula (IIA), each ---- independently represents a single bond or a double bond and each of the numbered carbons is covalently attached to one or more hydrogen atoms and/or one or more R groups to complete the valency of the respective carbon atom.

In certain embodiments, the method comprises forming a B-ring from an intermediate ACD-ring containing compound of Formula (Eii):

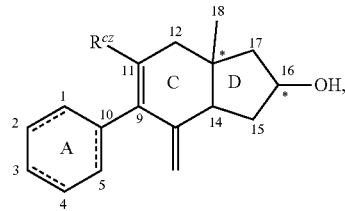
(Eii)

wherein $R^{CZ}$ is hydrogen or $Si(R^M)_3$, wherein each $R^M$ is independently selected from the group consisting of hydrogen, $C_{1-6}$-alkyl, trimethylsilyl, $C_{6-10}$-aryl, 5- to 10-membered heteroaryl, arylalkyl, and $-OR^{MX}$, wherein $R^{MX}$ is hydrogen, $C_{1-6}$-alkyl, or $C_{6-10}$-aryl; and each of the numbered carbons is covalently attached to one or more hydrogen atoms and/or one or more R groups to complete the valency of the respective carbon atom. In certain embodiments, each $R^M$ is $C_{1-6}$-alkyl. In some such embodiments, each $R^M$ is methyl. In certain embodiments, at least one $R^M$ is $C_{6-10}$-aryl and the remaining $R^M$ are hydrogen or $C_{1-6}$-alkyl. In certain embodiments, at least one $R^M$ is 5- to 10-membered heteroaryl (e.g., furyl) and the remaining $R^M$ are hydrogen or $C_{1-6}$-alkyl.

In certain embodiments, the intermediate ACD-ring containing compound of Formula (Eii) is formed by reacting a compound of Formula (Cii) with a compound of Formula (Dii):

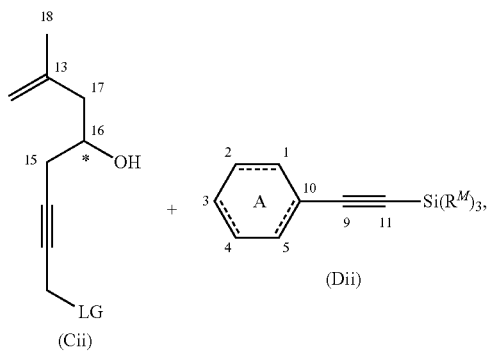
(Cii) (Dii)

wherein LG is a leaving group; and each $R^M$ is independently selected from the group consisting of hydrogen, $C_{1-6}$-alkyl, trimethylsilyl, $C_{6-10}$-aryl, 5- to 10-membered heteroaryl, arylalkyl, and $-OR^{MX}$, wherein $R^{MX}$ is hydrogen, $C_{1-6}$-alkyl, or $C_{6-10}$-aryl. Exemplary leaving groups include, but are not limited to, halogen, $-O-Ar^1$, where $Ar^1$ is a substituted or unsubstituted $C_{6-10}$-aryl or 5- to 10-membered heteroaryl, in particular $-O$-phenyl, and $-OSO_2R^{1a}$, wherein $R^{1a}$ is aryl, such as p-tolyl or phenyl; alkyl such as methyl or ethyl; fluoroalkyl such as trifluoromethyl, perfluorobutyl ($C_4F_9$), perfluoropentyl, perfluorohexyl, and perfluorooctyl; -fluoroalkyl-O-fluoroalkyl such as perfluoroethoxyethyl; $-N(alkyl)_2$; fluoro; or imidazolyl.

In certain embodiments, the method further comprises forming a compound Formula (IIB') from a compound of Formula (IIB) through Birch reduction and subsequent hydrolysis:

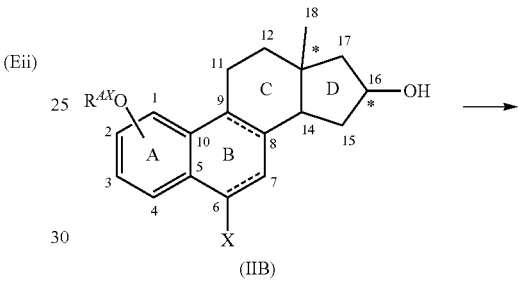
(IIB)

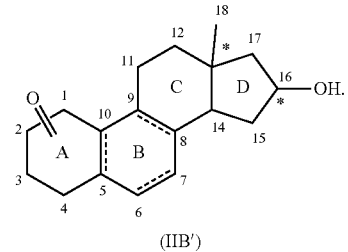
(IIB')

With respect to a compound of Formula (IIB), $R^{AX}$ is $C_{1-6}$-alkyl, $C_{2-10}$-alkenyl, $C_{2-10}$-alkynyl, $C_{1-10}$-haloalkyl, $-C(O)-C_{1-10}$-alkyl, $-C(O)-C_{6-10}$-aryl, $-C(O)$-heteroaryl, $-S(O)_2R^{Z1}$, $C_{6-10}$-aryl, or 5- to 10-membered heteroaryl; and X is a halogen or pseudohalogen. Each ---- independently represents a single bond or a double bond.

In certain embodiments, the method further comprises forming a compound of Formula (III) by (a) oxidation of a compound of Formula (IIA) to form a ketone of Formula (IIA') and (b) enolization of the ketone of Formula (IIA'):

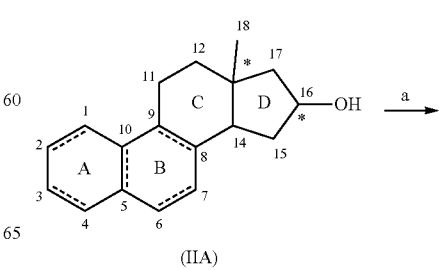
(IIA)

-continued

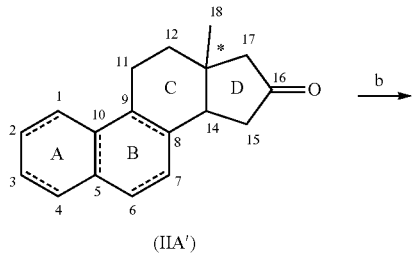

(IIA')

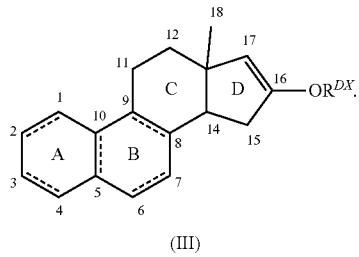

(III)

With respect to compounds of Formula (III), $R^{DX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl. Each ---- independently represents a single bond or a double bond.

In certain embodiments, the method further comprises forming a compound of Formula (IV) by (a) C6-borylation/oxidation of a compound of Formula (IIC) to form a compound of Formula (IIC') and (b) dearomative oxidation of the compound of Formula (IIC'):

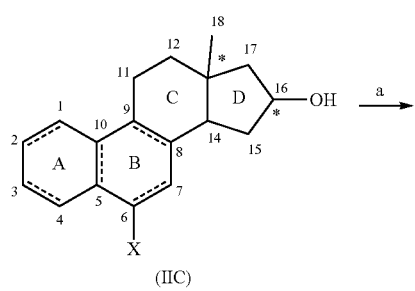

-continued

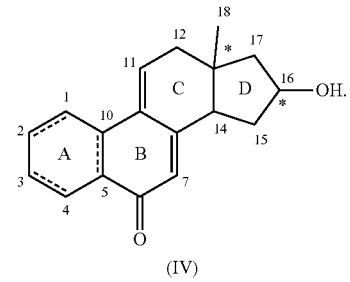

(IV)

With respect to compounds of Formula (IIC), X is a halogen or pseudohalogen. Each ---- independently represents a single bond or a double bond.

In certain embodiments, the method further comprises forming a compound Formula (IIC″) through coupling a compound of Formula (IIB) with a boronic acid or related organometalloid coupling partner (i.e. boronic ester, trialkylborane, etc):

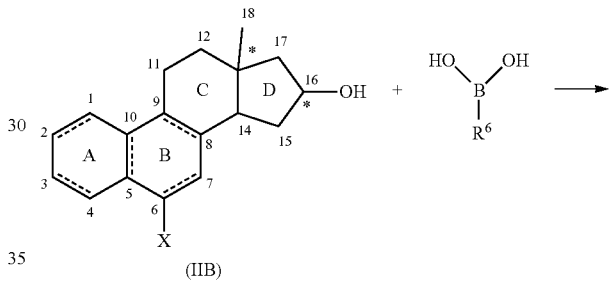

(IIB)

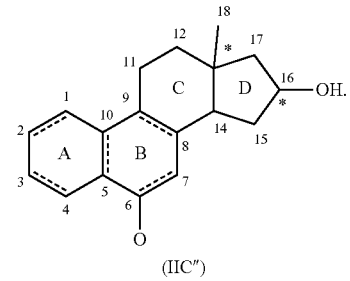

(IIC″)

With respect to a compound of Formula (IIB), X is a halogen or pseudohalogen; $R^6$ is selected from the group consisting of hydrogen, $C_{1-10}$-alkyl, $C_{2-10}$-alkenyl, $C_{2-10}$-alkynyl, $C_{1-10}$-haloalkyl, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl, wherein $R^{BX}$ is $C_{1-6}$-alkyl, $C_{2-10}$-alkenyl, $C_{2-10}$-alkynyl, $C_{1-10}$-haloalkyl, $C_{6-10}$-aryl, or 5- to 10-membered heteroaryl. Each ---- independently represents a single bond or a double bond.

In certain embodiments, the method further comprises forming a compound of Formula (IIA) by oxidizing a compound of Formula (IIA″):

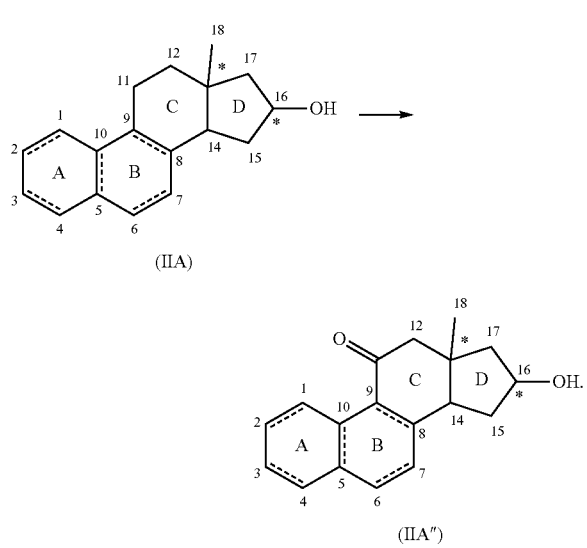

(IIA)

(IIA″)

With respect to a compound of Formula (IIA) and a compound of Formula (IIA″), each ---- independently represents a single bond or a double bond.

In one aspect, the present disclosure provides methods for producing enantiodefined polycyclic ring compounds. The methods of the present disclosure for producing enantiodefined polycyclic ring compounds and the resulting compositions are exemplified in the following general chemical scheme(s).

In certain embodiments, a steroidal tetracycle is produced from a hydrindane. Scheme 1 depicts an exemplary reaction for forming a steroidal tetracycle (G).

Scheme 1 Formation of steroidal tetracycle (G) from hydrindane (E)

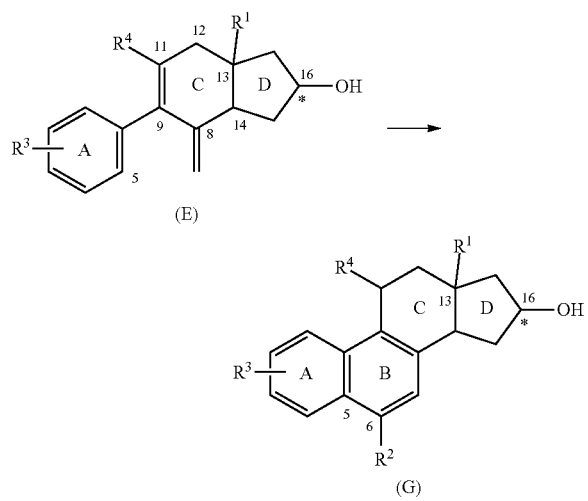

While the present disclosure is not limited to any particular mechanism(s) or mode(s) of action of the products of the synthesis process, it was contemplated that late-stage establishment of a steroidal tetracycle (i.e., steroidal A, B, C, D ring structure) as shown by an exemplary compound of Formula (Gi), below:

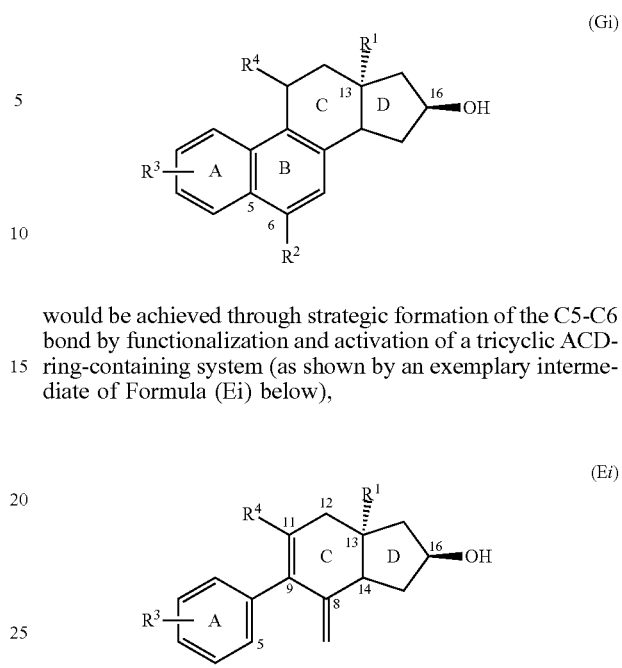

would be achieved through strategic formation of the C5-C6 bond by functionalization and activation of a tricyclic ACD-ring-containing system (as shown by an exemplary intermediate of Formula (Ei) below), as described herein. (An exemplary Scheme 1 reaction is shown in Example 2). Molecules of the general structure of intermediate of Formula (Ei) (e.g., functionalized/unsaturated hydrindanes), as shown above, are valuable intermediates in the subsequent synthetic methods of the present disclosure.

In certain embodiments, such intermediate compounds of Formula (E) above are produced using one or more conventional reaction(s); in certain particularly preferred examples of these embodiments. Scheme 2 depicts an exemplary reaction for forming a hydrindane of Formula (E).

Scheme 2
Formation of hydrindane (E) from alkyne (D) and chiral enyne (C)

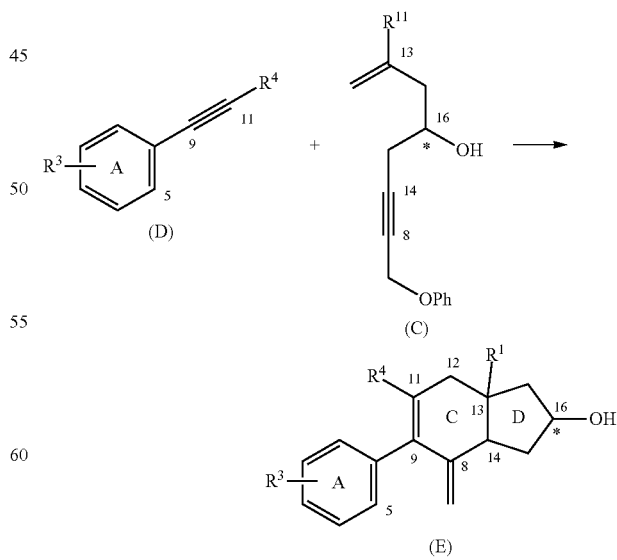

While not limited to any particular mechanisms, the present disclosure contemplates using metallacycle-mediated annulative cross-coupling reaction(s) between a suitably functionalized alkyne, exemplified by functionalized alkyne of Formula (D), reacted with a suitable chiral enyne, exemplified by chiral enyne of Formula (C) to produce the aforementioned functionalized hydrindane of Formula (E). (An exemplary Scheme 2 reaction is shown in Example 1).

In some exemplary embodiments of Scheme 1 and Scheme 2, $R^1$, $R^2$, $R^3$, and $R^4$ are each independently selected from the group consisting of $C_1$-$C_4$ alkyl; $C_2$-$C_4$ alkenyl; $C_2$-$C_4$ alkynyl; —$CF_3$; halo; =O; —OH; —O-($C_1$-$C_4$-alkyl); —$OCH_2F$; —$OCHF_2$; —$OCF_3$; —OC(O)-($C_1$-$C_4$-alkyl); —OC(O)-($C_1$-$C_4$-alkyl); —OC(O)NH-($C_1$-$C_4$-alkyl); —OC(O)N($C_1$-$C_4$-alkyl)$_2$; —OC(S)NH-($C_1$-$C_4$-alkyl); —OC(S)N($C_1$-$C_4$-alkyl)$_2$; —SH; —S-($C_1$-$C_4$-alkyl); —S(O)-($C_1$-$C_4$-alkyl); —S(O)$_2$-($C_1$-$C_4$-alkyl); —SC(O)-($C_1$-$C_4$-alkyl); —SC(O)O-($C_1$-$C_4$-alkyl); —$NH_2$; —N(H)-($C_1$-$C_4$-alkyl); —N($C_1$-$C_4$-alkyl)$_2$; —N(H)C(O)-($C_1$-$C_4$-alkyl); —N($CH_3$)C(O)-($C_1$-$C_4$-alkyl); —N(H)C(O)—$CF_3$; —N($CH_3$)C(O)-$CF_3$; —N(H)C(S)-($C_1$-$C_4$-alkyl); —N($CH_3$)C(S)-($C_1$-$C_4$-alkyl); —N(H)S(O)$_2$-($C_1$-$C_4$-alkyl); —N(H)C(O)$NH_2$; —N(H)C(O)NH-($C_1$-$C_4$-alkyl); —N($CH_3$)C(O)NH-($C_1$-$C_4$-alkyl); —N(H)C(O)N($C_1$-$C_4$-alkyl)$_2$; —N($CH_3$)C(O)N($C_1$-$C_4$-alkyl)$_2$; —N(H)S(O)$_2$$NH_2$; —N(H)S(O)$_2$NH-($C_1$-$C_4$-alkyl); —N($CH_3$)S(O)$_2$NH-($C_1$-$C_4$-alkyl); —N(H)S(O)$_2$N($C_1$-$C_4$-alkyl)$_2$; —N($CH_3$)S(O)$_2$N($C_1$-$C_4$-alkyl)$_2$; —N(H)C(O)O-($C_1$-$C_4$-alkyl); —N($CH_3$)C(O)O-($C_1$-$C_4$-alkyl); —N(H)S(O)$_2$O-($C_1$-$C_4$-alkyl); —N($CH_3$)S(O)$_2$O-($C_1$-$C_4$-alkyl); —N($CH_3$)C(S)NH-($C_1$-$C_4$-alkyl); —N($CH_3$)C(S)N($C_1$-$C_4$-alkyl)$_2$; —N($CH_3$)C(S)O-($C_1$-$C_4$-alkyl); —N(H)C(S)$NH_2$; —$NO_2$; —$CO_2$H; —$CO_2$-($C_1$-$C_4$-alkyl); —C(O)N(H)OH; —C(O)N($CH_3$)OH; —C(O)N($CH_3$)OH; —C(O)N($CH_3$)O-($C_1$-$C_4$-alkyl); —C(O)N(H)-($C_1$-$C_4$-alkyl); —C(O)N($C_1$-$C_4$-alkyl)$_2$; —C(S)N(H)-($C_1$-$C_4$-alkyl); —C(S)N($C_1$-$C_4$-alkyl)$_2$; —C(NH)N(H)-($C_1$-$C_4$-alkyl); —C(NH)N($C_1$-$C_4$-alkyl)$_2$; —C($NCH_3$)N(H)-($C_1$-$C_4$-alkyl); —C($NCH_3$)N($C_1$-$C_4$-alkyl)$_2$; —C(O)-($C_1$-$C_4$-alkyl); —C(NH)-($C_1$-$C_4$-alkyl); —C($NCH_3$)-($C_1$-$C_4$-alkyl); —C(NOH)-($C_1$-$C_4$-alkyl); —C($NOCH_3$)-($C_1$-$C_4$-alkyl); —CN; —CHO; —$CH_2$OH; —$CH_2$O-($C_1$-$C_4$-alkyl); —$CH_2NH_2$; —$CH_2$N(H)-($C_1$-$C_4$-alkyl); —$CH_2$N($C_1$-$C_4$-alkyl)$_2$; $C_6$-$C_{14}$-aryl; 5- to 14-membered heteroaryl; $C_3$-$C_{14}$-cycloalkyl; and 5- to 14-membered heterocyclyl.

In certain embodiments, unless otherwise stated or indicated by context, a substituent of a compound utilized in and/or produced by Scheme 1 and/or Scheme 2, such as an alkyl, alkenyl, alkynyl, cycloalkyl, aryl, heteroalkyl, heteroalkenyl, heteroalkynyl, heterocycloalkyl, or heteroaryl, is optionally substituted with one or more of substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —OC(O)$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, —N($R^a$)C(N$R^a$)N($R^a$)$_2$, —N($R^a$)S(O)$_t$$R^a$ (where t is 1 or 2), —S(O)$_t$O$R^a$ (where t is 1 or 2), —S(O)$_t$N($R^a$)$_2$ (where t is 1 or 2), or —$PO_3$($R^a$)$_2$ where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

More particularly, one contemplated synthetic embodiment starting with simple chiral precursors is described as follows.

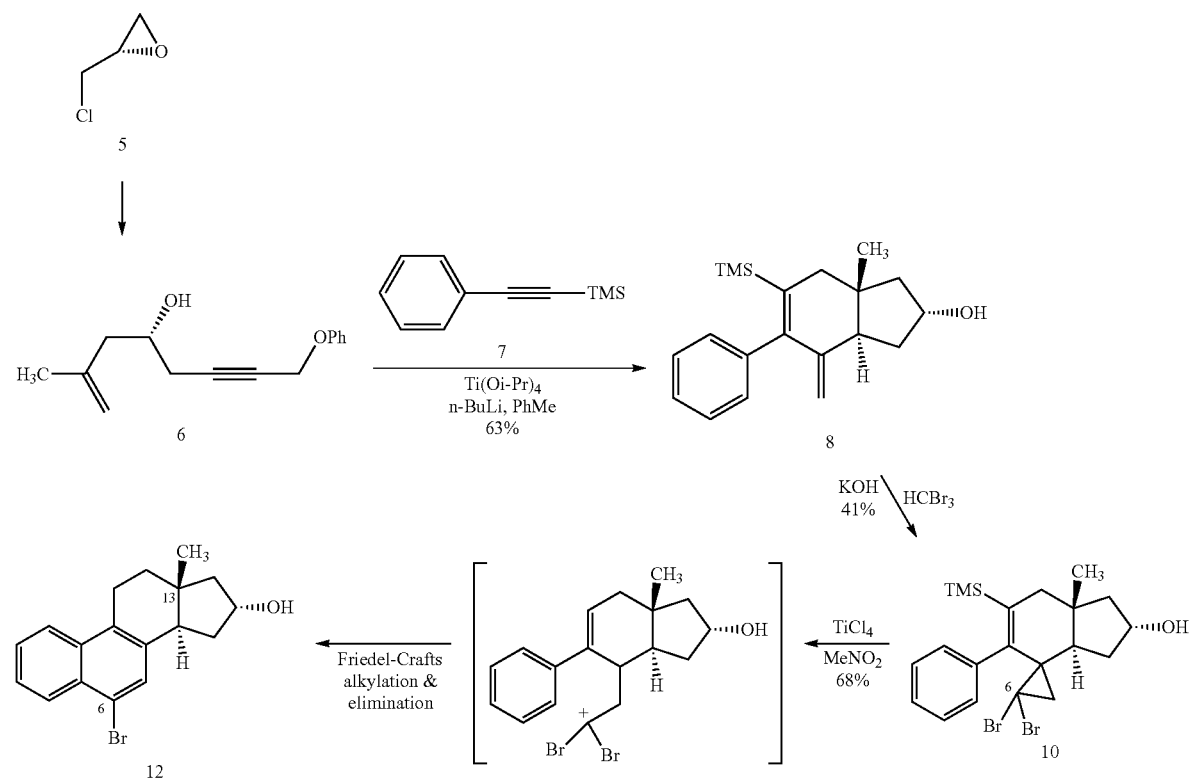

Briefly, in one embodiment a suitable chiral (optically active) bifunctional reagent (e.g., a three carbon starting material such as, but not limited to, epichlorohydrin 5) that is transformed to a substitute enyne (i.e., 6, prepared according to either: A) a two-step procedure, comprising (i) phenylpropargyl ether, n-BuLi, THF, −78° C. to rt (17%); and (ii) 2-propenylmagnesium bromide, CuI, THF, −78° C. to rt (70%); or, B) a three-step procedure, comprising (i) phenylpropargyl ether, n-BuLi, THF, $BF_3OEt_2$, −78° C.; (ii) KOt-Bu, $Et_2O$; and (iii) 2-propenylmagnesium bromide, CuI, THF, −78° C. to rt (63% over three steps)). While this synthetic pathway was employed in preferred embodiments to generate enynes that were advanced to steroidal compounds through the methods described in this invention, other pathways to functionalized enynes are understood to be compatible with the methods of this invention (i.e., including but not limited to the use of a substituted epoxyalcohol as described in Greszler, S. N., et al., *J. Am. Chem. Soc.* 2012, 134, 2766-2774, and Jeso, V., et al., *J. Am. Chem. Soc.*, 2014, 136, 8209-8212). Intermolecular metallacycle-mediated annulative cross-coupling of the enyne 6 with TMS-phenylacetylene 7 delivers hydrindane 8.

More particularly, the present disclosure contemplates a functionalization method wherein it is possible to install the steroidal C6 carbon in concert with revealing a reactive intermediate for B-ring formation. Preferably, a cyclopropanation reaction is used to accomplish this, here selectively engaging the 1,1-disubstituted alkene of 8 to produce the vinylcyclopropane intermediate 10. It is further contemplated, in certain specific embodiments, where the resulting cyclopropanation efficiency is undesirably low (or deemed inefficient) that overall yields can be increased (efficiency increased) by protecting the secondary alcohol prior to cyclopropanation (i.e., as its corresponding tertbutyldimethylsilyl ether ("TBS")). In certain preferred embodiments, the vinylcyclopropane intermediate 10 (or its TBS-protected derivative) is then treated with $TiCl_4$ in nitromethane (optionally in the presence of a protic additive, e.g., isopropanol).

While the present disclosure is not limited to any particular mechanism(s), and the compositions and methods of the present disclosure are not intended to be so limited, the present disclosure contemplates that the reaction of $TiCl_4$ with the D-ring hydroxy group [(or potentially with adventitious water, or an "O—H-containing" additive (i.e., isopropanol)] produces an in situ protic acid that converts vinylcyclopropane intermediate 10 to a reactive homoallylic cation intermediate (depicted above in brackets) through a process of protodesilylation, protonation of the resulting styrenyl alkene, and subsequent regioselective cyclopropane fragmentation. Ring closure is then accomplished through a bond-forming process that likely procedes by using the aromatic ring as a nucleophile in an intramolecular Friedel-Crafts alkylation, yielding an intermediate that is transformed to steroidal product 12 through loss of HBr (in 68% yield). In similar, but alternative embodiments, the reaction is augmented by the addition of suitable acid(s) in amounts and concentrations sufficient to yield the steroidal products of interest. It is understood that the "D-ring" C16-OH is not a required functionality for the acid-mediated B-ring-forming process.

Another contemplated synthetic embodiment starting with simple chiral precursors is described is depicted in the following reaction scheme:

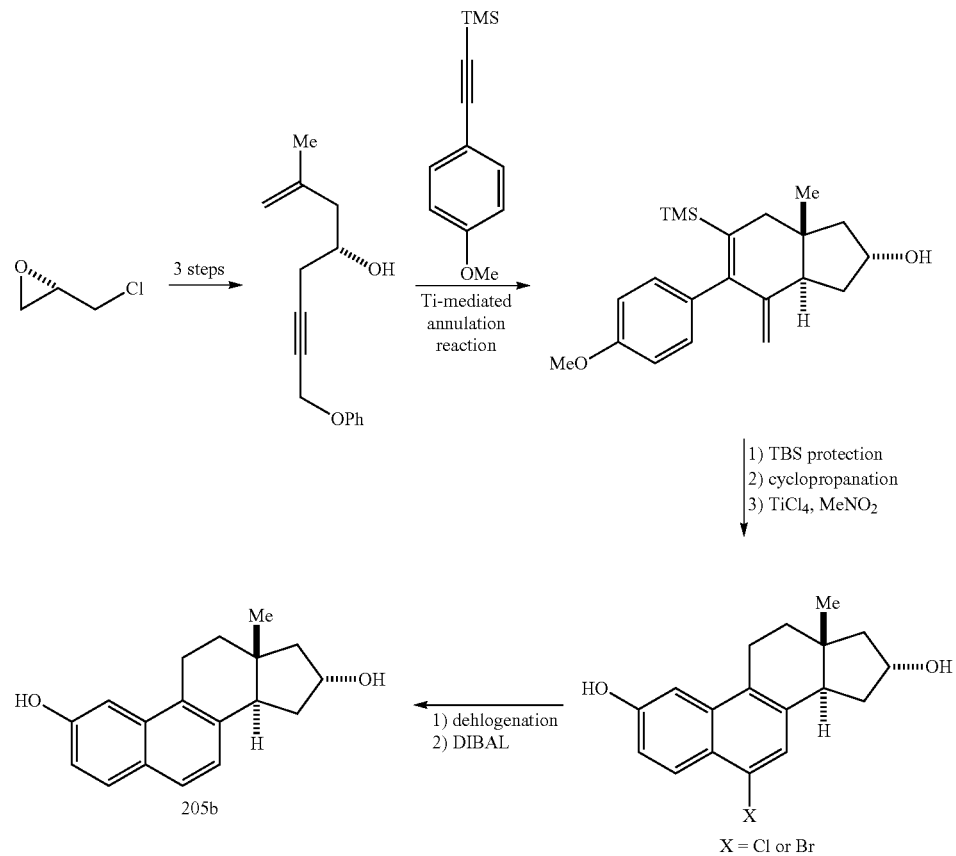

This overall process is contemplated to provide an angularly substituted trans-fused hydrindane in a convergent manner from acyclic precursors as well as to establish three $\sigma_{C-C}$ bonds and two stereocenters (one of which is quaternary).

In one aspect, the present disclosure includes intermediate compounds useful in the preparation of, inter alia, steroidal tetracycles disclosed herein.

In one particular aspect, the present disclosure provides an intermediate compound of Formula (Ei):

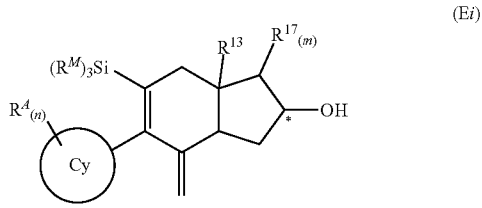

(Ei)

With respect to a compound of Formula (Ei), Cy is $C_{3-8}$-cycloalkyl, 3- to 10-membered heterocycloalkyl, $C_{6-10}$-aryl, or 5- to 10-membered heteroaryl;

each $R^M$ is independently selected from the group consisting of hydrogen, trimethylsilyl, $C_{1-6}$-alkyl, $C_{6-10}$-aryl, 5- to 10-membered heteroaryl, arylalkyl, and —$OR^{MX}$, wherein $R^{MX}$ is hydrogen, $C_{1-6}$-alkyl, or $C_{6-10}$-aryl;

n is an integer selected from the group consisting of 0, 1, 2, 3, 4, 5, 6, 7, 8, 9, and 10;

m is an integer selected from 0, 1, and 2;

$R^A$ is selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, or two $R^A$ together form an oxo,
wherein $R^{AX}$ is $C_{1-6}$-alkyl, $C_{2-10}$-alkenyl, $C_{2-10}$-alkynyl, $C_{1-10}$-haloalkyl, —$C(O)$-$C_{1-10}$-alkyl, —$C(O)$-$C_{6-10}$-aryl, —$C(O)$-heteroaryl, —$S(O)_2R^{Z1}$, $C_{6-10}$-aryl, or 5- to 10-membered heteroaryl,
wherein $R^{AY}$ is hydrogen, $C_{1-6}$-alkyl, $C_{2-10}$-alkenyl, $C_{2-10}$-alkynyl, $C_{1-10}$-haloalkyl, —$C(O)$-$C_{1-10}$-alkyl, —$C(O)$-$C_{6-10}$-aryl, —$C(O)$-heteroaryl, $C_{6-10}$-aryl, or 5- to 10-membered heteroaryl,
wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy;

$R^{13}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy; and each $R^{17}$ is independently selected from the group consisting of hydrogen, $C_{1-10}$-alkyl, $C_{2-10}$-alkenyl, $C_{2-10}$-alkynyl, $C_{1-10}$-haloalkyl, and halogen, or two $R^{17A}$ together form an oxo;

wherein any $C_{3-8}$-cycloalkyl, 3- to 10-membered heterocycloalkyl, $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In certain embodiments, Cy is a substituted or unsubstituted $C_{6-10}$-aryl or 5- to 10-membered heteroaryl. In some such embodiments, Cy is unsubstituted phenyl. In some such embodiments, Cy is phenyl substituted with one or more $C_{1-6}$-alkyl, $C_{1-6}$-alkoxy, or halogen.

In certain embodiments, at least one $R^M$ is $C_{1-6}$-alkyl and, preferably, all three $R^M$ are $C_{1-6}$-alkyl (e.g., each $R^M$ is methyl to form trimethylsilyl).

In certain embodiments, $R^{13}$ is $C_{1-6}$-alkyl.

In certain embodiments, each $R^{17}$ is hydrogen.

In another particular aspect, the present disclosure provides an intermediate compound of Formula (Fi):

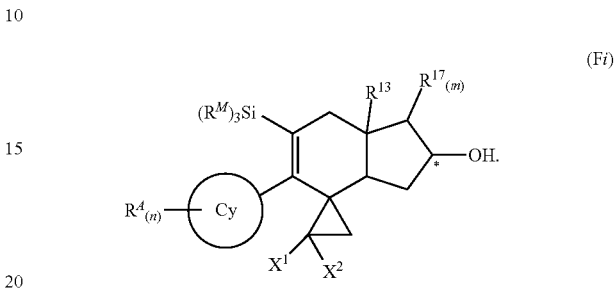

(Fi)

With respect to a compound of Formula (Fi), Cy is $C_{3-8}$-cycloalkyl, 3- to 10-membered heterocycloalkyl, $C_{6-10}$-aryl, or 5- to 10-membered heteroaryl;

each $R^M$ is independently selected from the group consisting of hydrogen, trimethylsilyl, $C_{1-6}$-alkyl, $C_{6-10}$-aryl, 5- to 10-membered heteroaryl, arylalkyl, and —$OR^{MX}$, wherein $R^{MX}$ is hydrogen, $C_{1-6}$-alkyl, or $C_{6-10}$-aryl;

n is an integer selected from the group consisting of 0, 1, 2, 3, 4, 5, 6, 7, 8, 9, and 10;

m is an integer selected from 0, 1, and 2;

$R^A$ is selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, or two $R^A$ together form an oxo,
wherein $R^{AX}$ is $C_{1-6}$-alkyl, $C_{2-10}$-alkenyl, $C_{2-10}$-alkynyl, $C_{1-10}$-haloalkyl, —$C(O)$-$C_{1-10}$-alkyl, —$C(O)$-$C_{6-10}$-aryl, —$C(O)$-heteroaryl, —$S(O)_2R^{Z1}$, $C_{6-10}$-aryl, or 5- to 10-membered heteroaryl,
wherein $R^{AY}$ is hydrogen, $C_{1-6}$-alkyl, $C_{2-10}$-alkenyl, $C_{2-10}$-alkynyl, $C_{1-10}$-haloalkyl, —$C(O)$-$C_{1-10}$-alkyl, —$C(O)$-$C_{6-10}$-aryl, —$C(O)$-heteroaryl, $C_{6-10}$-aryl, or 5- to 10-membered heteroaryl,
wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy;

$R^{13}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy;

each $R^{17}$ is independently selected from the group consisting of hydrogen, $C_{1-10}$-alkyl, $C_{2-10}$-alkenyl, $C_{2-10}$-alkynyl, $C_{1-10}$-haloalkyl, and halogen, or two $R^{17A}$ together form an oxo; and $X^1$ and $X^2$ are independently selected from the group consisting of hydrogen, $C_{1-10}$-alkyl, $C_{2-10}$-alkenyl, $C_{2-10}$-alkynyl, $C_{1-10}$-haloalkyl, halogen, oxygen, —$OR^{BX}$, —$SR^{BY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl;

wherein any $C_{3-8}$-cycloalkyl, 3- to 10-membered heterocycloalkyl, $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In certain embodiments, Cy is a substituted or unsubstituted $C_{6-10}$-aryl or 5- to 10-membered heteroaryl. In some such embodiments, Cy is unsubstituted phenyl. In some such embodiments, Cy is phenyl substituted with one or more $C_{1-6}$-alkyl, $C_{1-6}$-alkoxy, or halogen.

In certain embodiments, at least one $R^M$ is $C_{1-6}$-alkyl and, preferably, all three $R^M$ are $C_{1-6}$-alkyl (e.g., each $R^M$ is methyl to form trimethylsilyl).

In certain embodiments, $R^{13}$ is $C_{1-6}$-alkyl.

In certain embodiments, each $R^{17}$ is hydrogen.

In still other particular aspects, the present disclosure provides a vinylcyclopropane intermediate of Formula (Fii):

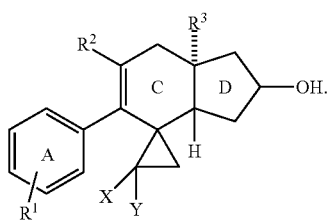

With respect to a compound of Formula (Fii), X and Y represent a halogen atom (e.g., F, Cl, Br, and/or I) or in cases where a single halogen atom is present (i.e., X=Br), the other group (Y) can be a variety of other substituents including, but not limited to, alkyl, aryl, heteroaryl, and other heteroatomic groups capable of supporting the subsequent ring closing reaction (i.e., OR, NR, $NR_2$ SR, where R=alkyl, aryl, heteroaryl, acyl, and the like). Moreover, $R^1$, $R^2$, and $R^3$ can be as described above, for example, each of $R^1$, $R^2$, and $R^3$ may be independently selected from the group consisting of $C_1$-$C_4$ alkyl; $C_2$-$C_4$ alkenyl; $C_2$-$C_4$ alkynyl; —$CF_3$; halo; =O; —OH; —O-($C_1$-$C_4$-alkyl); —$OCH_2F$; —$OCHF_2$; —$OCF_3$; —OC(O)-($C_1$-$C_4$-alkyl); —OC(O)-($C_1$-$C_4$-alkyl); —OC(O)NH-($C_1$-$C_4$-alkyl); —OC(O)N($C_1$-$C_4$-alkyl)$_2$; —OC(S)NH-($C_1$-$C_4$-alkyl); —OC(S)N($C_1$-$C_4$-alkyl)$_2$; —SH; —S-($C_1$-$C_4$-alkyl); —S(O)-($C_1$-$C_4$-alkyl); —S(O)$_2$-($C_1$-$C_4$-alkyl); —SC(O)-($C_1$-$C_4$-alkyl); —SC(O)O-($C_1$-$C_4$-alkyl); —$NH_2$; —N(H)-($C_1$-$C_4$-alkyl); —N($C_1$-$C_4$-alkyl)$_2$; —N(H)C(O)-($C_1$-$C_4$-alkyl); —N($CH_3$)C(O)-($C_1$-$C_4$-alkyl); —N(H)C(O)—$CF_3$; —N($CH_3$)C(O)—$CF_3$; —N(H)C(S)-($C_1$-$C_4$-alkyl); —N($CH_3$)C(S)-($C_1$-$C_4$-alkyl); —N(H)S(O)$_2$-($C_1$-$C_4$-alkyl); —N(H)C(O)$NH_2$; —N(H)C(O)NH-($C_1$-$C_4$-alkyl); —N($CH_3$)C(O)NH-($C_1$-$C_4$-alkyl); —N(H)C(O)N($C_1$-$C_4$-alkyl)$_2$; —N($CH_3$)C(O)N($C_1$-$C_4$-alkyl)$_2$; —N(H)S(O)$_2NH_2$; —N(H)S(O)$_2$NH-($C_1$-$C_4$-alkyl); —N($CH_3$)S(O)$_2$NH-($C_1$-$C_4$-alkyl); —N(H)S(O)$_2$N($C_1$-$C_4$-alkyl)$_2$; —N($CH_3$)S(O)$_2$N($C_1$-$C_4$-alkyl)$_2$; —N(H)C(O)O-($C_1$-$C_4$-alkyl); —N($CH_3$)C(O)O-($C_1$-$C_4$-alkyl); —N(H)S(O)$_2$O-($C_1$-$C_4$-alkyl); —N($CH_3$)S(O)$_2$O-($C_1$-$C_4$-alkyl); —N($CH_3$)C(S)NH-($C_1$-$C_4$-alkyl); —N($CH_3$)C(S)N($C_1$-$C_4$-alkyl)$_2$; —N($CH_3$)C(S)O-($C_1$-$C_4$-alkyl); —N(H)C(S)$NH_2$; —$NO_2$; —$CO_2H$; —$CO_2$-($C_1$-$C_4$-alkyl); —C(O)N(H)OH; —C(O)N($CH_3$)OH; —C(O)N($CH_3$)OH; —C(O)N($CH_3$)O-($C_1$-$C_4$-alkyl); —C(O)N(H)-($C_1$-$C_4$-alkyl); —C(O)N($C_1$-$C_4$-alkyl)$_2$; —C(S)N(H)-($C_1$-$C_4$-alkyl); —C(S)N($C_1$-$C_4$-alkyl)$_2$; —C(NH)N(H)-($C_1$-$C_4$-alkyl); —C(NH)N($C_1$-$C_4$-alkyl)$_2$; —C($NCH_3$)N(H)-($C_1$-$C_4$-alkyl); —C($NCH_3$)N($C_1$-$C_4$-alkyl)$_2$; —C(O)-($C_1$-$C_4$-alkyl); —C(NH)-($C_1$-$C_4$-alkyl); —C($NCH_3$)-($C_1$-$C_4$-alkyl); —C(NOH)-($C_1$-$C_4$-alkyl); —C($NOCH_3$)-($C_1$-$C_4$-alkyl); —CN; —CHO; —$CH_2OH$; —$CH_2$O-($C_1$-$C_4$-alkyl); —$CH_2NH_2$; —$CH_2$N(H)-($C_1$-$C_4$-alkyl); —$CH_2$N($C_1$-$C_4$-alkyl)$_2$; $C_6$-$C_{14}$-aryl; 5- to 14-membered heteroaryl; $C_3$-$C_{14}$-cycloalkyl; and 5- to 14-membered heterocyclyl.

In certain embodiments, an alkyne of Formula (D) is used to form an A-CD-containing tricycle of Formula (E), which is then used to produce a steroidal tetracycle. As illustrated in FIG. 1, the methods of the present disclosure and the chemical pathways therein are useful for generating a wide range of steroidal systems in a concise and enantiospecific fashion.

Certain particular exemplary embodiments are described in the Examples and in the following Tables 1-8. Common Notations in Tables 1-8: (a) yield reported is for the combination of diene isomers (trans-fused product containing an exo-1,1-disubstituted alkene+bicyclic product containing an endocyclic diene); (b) stereoselectivity for the annulation process (trans:cis) is typically ~6:1; (c) yield reported is for the 2-3 step sequence; and (d) regioselectivity is based on $^1$H NMR of the crude reaction product).

TABLE 1

| Alkyne of Formula (D) | Yield (%) | A-CD Tricycle (trans isomer:endo diene)$^{a,b}$ | Yield$^c$ (%) | 19-nor Steroid (rs)$^d$ |
|---|---|---|---|---|
| TMS—≡—Ph (7) | 69 | TMS, Me, 16-OH, H (ent-8) (4:1) | 26$^e$ | TMS, Me, 13-OH, H, Br (ent-12) |

Notation:
$^e$cyclization sequence was conducted without protection of the C16 hydroxy group.

Table 1, demonstrates the facility of certain embodiments of the present disclosure wherein an ent-steroid, ent-6 (derived from (+)-epichlorohydrin 5), was converted to steroidal product ent-12. The efficiency of the two-step ring-closing process (ent-8→ent-12) illustrates the challenge of accomplishing cyclopropanation in the presence of the C16-OH.

TABLE 2

| Alkyne of Formula (D) | Yield (%) | A-CD Tricycle (trans isomer:endo diene)[a,b] | Yield[c] (%) | 19-nor Steroid (rs)[d] |
|---|---|---|---|---|
| 13 (TMS-alkyne, 3-MeO-phenyl) | 43 | 14 (5:1) | 57 | 15 (≥ 20:1) |

TABLE 3

| Alkyne of Formula (D) | Yield (%) | A-CD Tricycle (trans isomer:endo diene)[a,b] | Yield[c] (%) | 19-nor Steroid (rs)[d] |
|---|---|---|---|---|
| 16 (TMS-alkyne, 3,4,5-tri-MeO-phenyl) | 57 | 17 (2.5:1) | 33 | 18 (≥ 20:1) |

Table 2 illustrates that in certain embodiments the efficiency of the overall process is substantially greater if the C16 hydroxy group is silylated prior to cyclopropanation and, when taken with the illustration in Table 3, demonstrates the capability of the present methods to produce A-ring aromatic steroids containing varied oxygenation patterns (compounds 15 and 18).

TABLE 4

| Alkyne of Formula (D) | Yield (%) | A-CD Tricycle (trans isomer:endo diene)[a,b] | Yield[c] (%) | 19-nor Steroid (rs)[d] |
|---|---|---|---|---|
| 19 (TMS-alkyne, 4-Cl-phenyl) | 51 | 20 (2.4:1) | —[f] | 21a (2-Cl):21b (3-Cl) (~1:1) |

Notation:
[f] yield for this unselective process was not determined.

Figure 2:
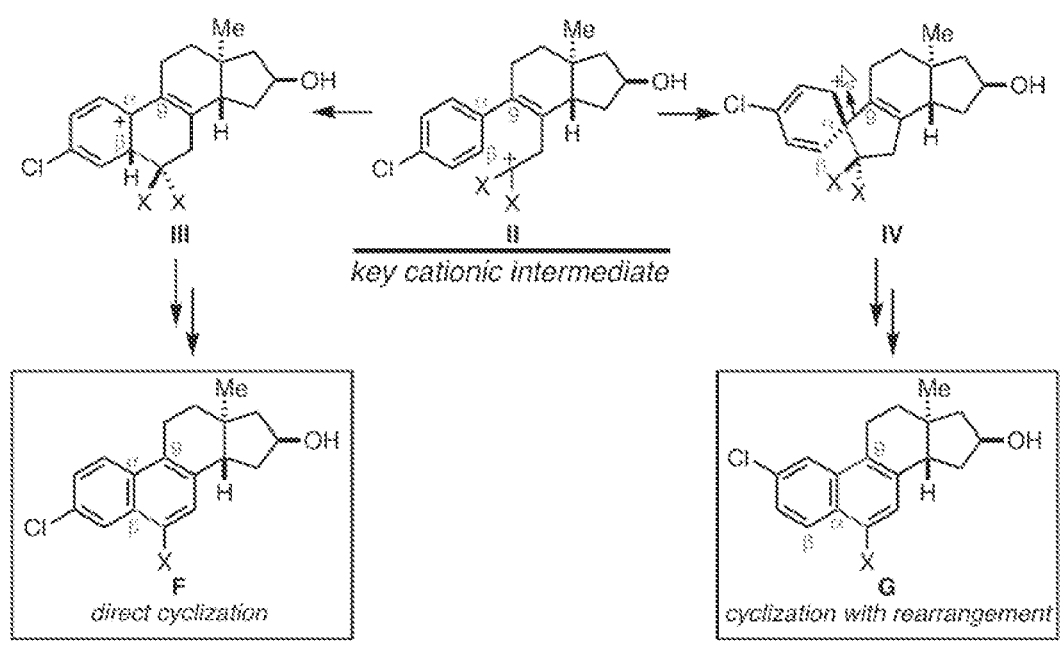
FIG. 2 shows the mechanistic divergence in the vinylcyclopropane rearrangement and intramolecular Friedel-Crafts alkylation process, wherein, formation of C—C bonds is depicted in intermediate (III) between C5-C6; in intermediate (IV) between C5-C6; in intermediate (F) between C5-C6; and in intermediate (G) between C5-C6 and C9-C10, respectively. Reaction by way of intermediate III does not proceed by rearrangement after C5-C6 bond-formation, and reaction by way of intermediate IV proceeds by an alkyl shift after formation of the C5-C6 bond.

As illustrated in Table 4, the use of the p-chloro-substituted phenylacetylene 19 led to the discovery that the final ring closure can proceed with additional rearrangement. In this embodiment, steroidal products 21a and 21b were produced in roughly equal proportions. While the present disclosure is not limited to any particular mechanism(s), it is contemplated that this observation is consistent with the proposed (non-limiting) mechanism depicted in FIG. 2, where cyclization is thought to proceed either through direct Friedel-Crafts alkylation (II→III→F), or by initial formation of a spirocyclic intermediate and subsequent rearrangement with selective migration of C9 (II→IV→G).

TABLE 5

| Alkyne of Formula (D) | Yield (%) | A-CD Tricycle (trans isomer:endo diene)$^{a,b}$ | Yield$^c$ (%) | 19-nor Steroid (rs)$^d$ |
|---|---|---|---|---|
| 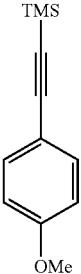 22 | 55 | 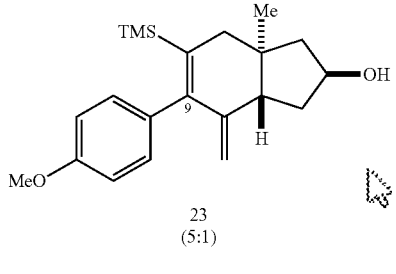 [SMILES: C=C1C(c2ccc(OC)cc2)=C([Si](C)(C)C)C[C@@]2(C)C[C@@H](O)C[C@H]12] 23 (5:1) | 34 | 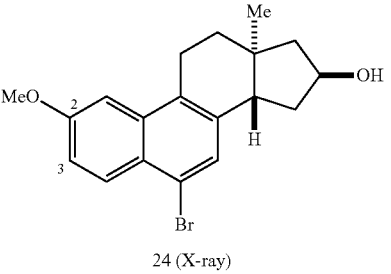 24 (X-ray) (≥ 20:1) |

Table 5 illustrates that certain preferred embodiments of the present disclosure achieve high levels of selectivity in favor of ring closure by rearrangement. In particular, in this embodiment, the p-methoxy-substituent of compound 23 plays a significant role in biasing the course of reaction. While the present disclosure is not limited to any particular mechanism(s), it is contemplated that this observation is likely due to the electronic contribution of the electron rich aromatic, favoring the formation of a spirocyclic intermediate similar to intermediate IV represented in FIG. 2. The production of the C2-methoxy-substituted steroid 24 was found to proceed with very high levels of selectivity (rs≥20:1).

TABLE 6

| Alkyne of Formula (D) | Yield (%) | A-CD Tricycle (trans isomer:endo diene)$^{a,b}$ | Yield$^c$ (%) | 19-nor Steroid (rs)$^d$ |
|---|---|---|---|---|
| 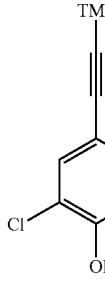 25 | 49 | 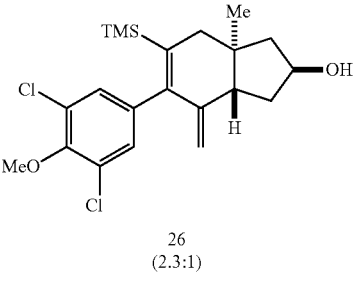 [SMILES: C=C1C(c2cc(Cl)c(OC)c(Cl)c2)=C([Si](C)(C)C)C[C@@]2(C)C[C@@H](O)C[C@H]12] 26 (2.3:1) | 31 | 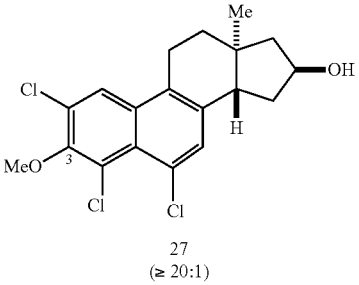 [SMILES: COc1c(Cl)cc2c3c(cc(Cl)c2c1Cl)[C@H]1C[C@H](O)C[C@]1(C)CC3] 27 (≥ 20:1) |

Table 6, illustrates still further embodiments of the present disclosure wherein the modification of A-ring substitution (compound 26) restored a preference for cyclization without rearrangement. More particularly, in this embodiment, cyclization delivered the C3-methoxy-substituted steroid 27 as a single regioisomer in a 31% yield (over three steps). While not limited to any particular mechanism(s), it is contemplated that this observation is consistent with steric effects stemming from the chloride substituents that may dissuade oxonium ion formation in the spirocyclic intermediate (i.e., an oxonium ion intermediate would be destabilized by significant 1,5-interactions between the methyl group of the oxonium ion and one of the ortho chlorine substituents).

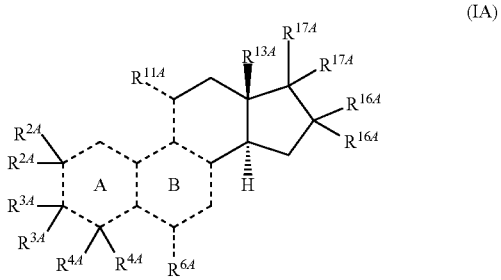

(IA)

TABLE 7

| Alkyne of Formula (D) | Yield (%) | A-CD Tricycle (trans isomer:endo diene)[a,b] | Yield[c] (%) | 19-nor Steroid (rs)[d] |
|---|---|---|---|---|
| 28 | 52 | 29 (4:1) | 68 | 30 (≥ 20:1) |

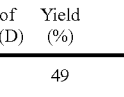

TABLE 8

| Alkyne of Formula (D) | Yield (%) | A-CD Tricycle (trans isomer:endo diene)[a,b] | Yield[c] (%) | 19-nor Steroid (rs)[d] |
|---|---|---|---|---|
| 31 | 49 | 32 (5:1) | 46 | 33 (3:1) |

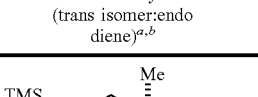

Table 7 and Table 8 provide yet additional embodiments and examples that illustrate the utility and selectivity of the various methods of the present disclosure to produce steroidal products having varying A-ring structures and substitutions.

C. Exemplary Steroidal Compounds

In one aspect, this disclosure provides a compound, intermediate, or salt thereof, wherein the compound either has a structure corresponding to Formula (IA), Formula (IB), Formula (IC), or Formula (ID), or could be transformed to such structures by methods well known to those skilled in the art of synthetic organic chemistry:

-continued

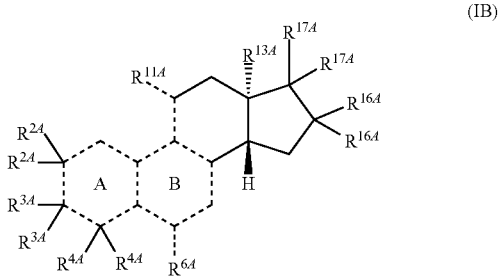

(IB)

-continued

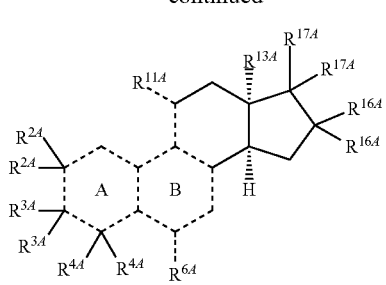

(IC)

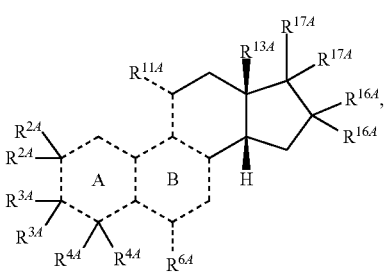

(ID)

wherein
each $R^{2A}$ and each $R^{4A}$ is independently absent or, when present, selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl, or two $R^{2A}$ together or two $R^{4A}$ together form an oxo,
wherein $R^{AX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, —C(O)-O-$C_{1-10}$-alkyl, —C(O)—O-$C_{6-10}$-aryl, —C(O)—O-heteroaryl, —C(O)—$NR^{Z1}R^{Z2}$, —$S(O)_2R^{Z1}$, $C_{6-10}$-aryl, or 5- to 10-membered heteroaryl,
wherein $R^{AY}$ is hydrogen, $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl,
wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy;
each $R^{3A}$ is independently absent or, when present, selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;
$R^{6A}$ is selected from the group consisting of hydrogen, $C_{1-10}$-alkyl, $C_{2-10}$-alkenyl, $C_{2-10}$-alkynyl, $C_{1-10}$-haloalkyl, halogen, oxygen, boronic acid, boronic acid ester, —$OR^{BX}$, —$SR^{BY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl,
wherein $R^{BX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl, wherein $R^{BY}$ is hydrogen, $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl;
$R^{11A}$ is selected from the group consisting of hydrogen, oxygen, and $OR^{CX}$,
wherein $R^{CX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl;
$R^{13A}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy;
each $R^{16A}$ is independently selected from the group consisting of hydrogen, hydroxy, —$OR^{DX}$, —$SR^{DY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, and, —C(O)-$C_{1-10}$-alkyl, or two $R^{16A}$ together form an oxo,
wherein $R^{DX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl,
wherein $R^{DY}$ is hydrogen, $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl;
each $R^{17A}$ is independently selected from the group consisting of hydrogen, $C_{1-10}$-alkyl, $C_{2-10}$-alkenyl, $C_{2-10}$-alkynyl, $C_{1-10}$-haloalkyl, and halogen, or two $R^{17A}$ together form an oxo;
each ---- independently represents a single bond or a double bond;
the A ring is saturated, partially unsaturated, or completely unsaturated; and
the B ring is saturated, partially unsaturated, or completely unsaturated;
wherein any $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In one aspect, this disclosure provides a compound or salt thereof, wherein the compound has a structure corresponding to Formula (IA-1) or Formula (IA-2), or could be transformed to such structures by methods well known to those skilled in the art of synthetic organic chemistry:

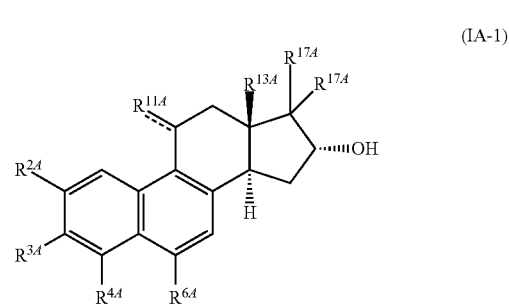

(IA-1)

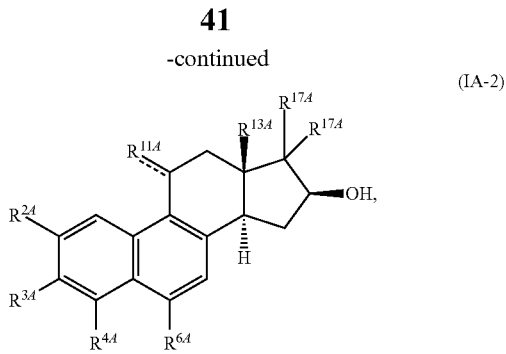

(IA-2)

wherein
- each of $R^{2A}$ and $R^{4A}$ are independently selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;
- $R^{3A}$ is selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;
- $R^{6A}$ is selected from the group consisting of hydrogen, $C_{1-10}$-alkyl, $C_{2-10}$-alkenyl, $C_{2-10}$-alkynyl, $C_{1-10}$-haloalkyl, halogen, —$OR^{BX}$, —$SR^{BY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl;
- $R^{11A}$ is selected from the group consisting of hydrogen, oxygen, and $OR^{CX}$,
  - wherein if $R^{11A}$ is oxygen, then ---- represents a double bond and if $R^{11A}$ is hydrogen or $OR^{CX}$, then ---- represents a single bond;
- $R^{13A}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy; and
- each $R^{17A}$ is independently selected from the group consisting of hydrogen, $C_{1-10}$-alkyl, $C_{2-10}$-alkenyl, $C_{2-10}$-alkynyl, $C_{1-10}$-haloalkyl, and halogen;
- wherein any $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In certain embodiments, $R^{2A}$ and $R^{4A}$ each is independently selected from the group consisting of hydrogen, $C_{1-6}$-alkyl, halogen, hydroxy, and —$OR^{AX}$; $R^{3A}$ is selected from the group consisting of hydrogen, $C_{1-6}$-alkyl, and —$OR^{AX}$; $R^{6A}$ is selected from the group consisting of hydrogen, halogen, —$OR^{BX}$, $C_{6-10}$-aryl optionally substituted with one or more $C_{1-6}$-alkoxy, and $C_{6-10}$-aryl-$C_{2-6}$-alkynyl, wherein the $C_{6-10}$-aryl of the $C_{6-10}$-aryl-$C_{2-6}$-alkynyl is unsubstituted; $R^{11A}$ is hydrogen; $R^{13A}$ is selected from the group consisting of $C_{1-6}$-alkyl and $C_{6-10}$-aryl-$C_{1-6}$-alkyl, wherein the $C_{6-10}$-aryl of the $C_{6-10}$-aryl-$C_{1-6}$-alkyl is unsubstituted; and each $R^{17A}$ is hydrogen.

In one aspect, this disclosure provides a compound or salt thereof, wherein the compound has a structure corresponding to Formula (IB-1) or Formula (IB-2), or could be transformed to such structures by methods well known to those skilled in the art of synthetic organic chemistry:

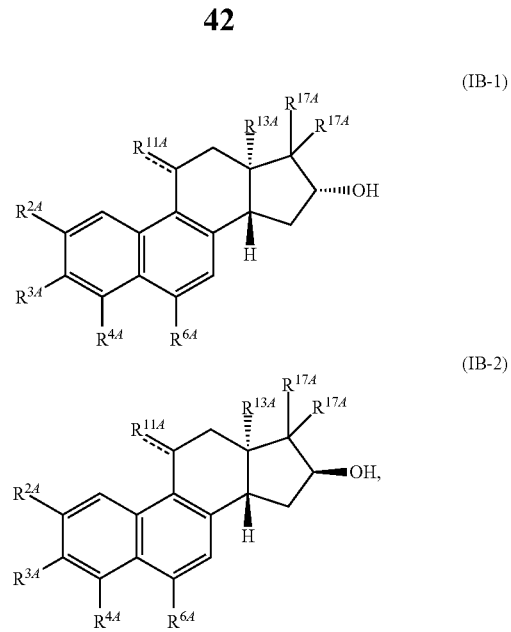

(IB-1)

(IB-2)

wherein
- each of $R^{2A}$ and $R^{4A}$ are independently selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;
- $R^{3A}$ is selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;
- $R^{6A}$ is selected from the group consisting of hydrogen, $C_{1-10}$-alkyl, $C_{2-10}$-alkenyl, $C_{2-10}$-alkynyl, $C_{1-10}$-haloalkyl, halogen, —$OR^{BX}$, —$SR^{BY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl;
- $R^{11A}$ is selected from the group consisting of hydrogen, oxygen, and $OR^{CX}$,
  - wherein if $R^{11A}$ is oxygen, then ---- represents a double bond and if $R^{11A}$ is hydrogen or $OR^{CX}$, then ---- represents a single bond;
- $R^{13A}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy; and
- each $R^{17A}$ is independently selected from the group consisting of hydrogen, $C_{1-10}$-alkyl, $C_{2-10}$-alkenyl, $C_{2-10}$-alkynyl, $C_{1-10}$-haloalkyl, and halogen;
- wherein any $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In certain embodiments, $R^{2A}$ and $R^{4A}$ each is independently selected from the group consisting of hydrogen, $C_{1-6}$-alkyl, halogen, hydroxy, and —$OR^{AX}$; $R^{3A}$ is selected from the group consisting of hydrogen, $C_{1-6}$-alkyl, and —$OR^{AX}$; $R^{6A}$ is selected from the group consisting of hydrogen, halogen, —$OR^{BX}$, $C_{6-10}$-aryl optionally substituted with one or more $C_{1-6}$-alkoxy, and $C_{6-10}$-aryl-$C_{2-6}$- alkynyl, wherein the $C_{6-10}$-aryl of the $C_{6-10}$-aryl-$C_{2-6}$-alkynyl is unsubstituted; $R^{11A}$ is hydrogen; $R^{13A}$ is selected from the group consisting of $C_{1-6}$-alkyl and $C_{6-10}$-aryl-$C_{1-6}$-alkyl, wherein the $C_{6-10}$-aryl of the $C_{6-10}$-aryl-$C_{1-6}$-alkyl is unsubstituted; and each $R^{17A}$ is hydrogen.

In one aspect, this disclosure provides a compound or salt thereof, wherein the compound has a structure corresponding to Formula (IC-1) or Formula (IC-2), or could be transformed to such structures by methods well known to those skilled in the art of synthetic organic chemistry:

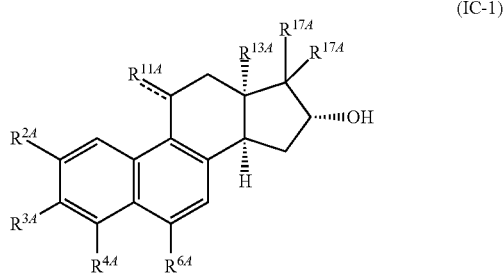

(IC-1)

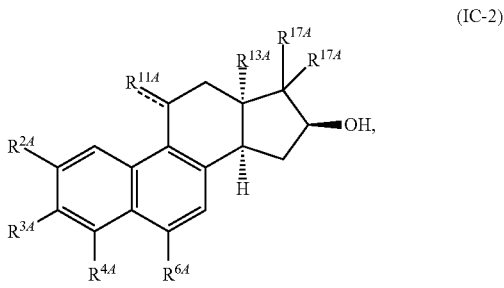

(IC-2)

wherein
each of $R^{2A}$ and $R^{4A}$ are independently selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;

$R^{3A}$ is selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;

$R^{6A}$ is selected from the group consisting of hydrogen, $C_{1-10}$-alkyl, $C_{2-10}$-alkenyl, $C_{2-10}$-alkynyl, $C_{1-10}$-haloalkyl, halogen, —$OR^{BX}$, —$SR^{BY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl;

$R^{11A}$ is selected from the group consisting of hydrogen, oxygen, and $OR^{CX}$,
wherein if $R^{11A}$ is oxygen, then ---- represents a double bond and if $R^{11A}$ is hydrogen or $OR^{CX}$, then ---- represents a single bond;

$R^{13A}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy; and each $R^{17A}$ is independently selected from the group consisting of hydrogen, $C_{1-10}$-alkyl, $C_{2-10}$-alkenyl, $C_{2-10}$-alkynyl, $C_{1-10}$-haloalkyl, and halogen;

wherein any $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In certain embodiments, $R^{2A}$ and $R^{4A}$ each is independently selected from the group consisting of hydrogen, $C_{1-6}$-alkyl, halogen, hydroxy, and —$OR^{AX}$; $R^{3A}$ is selected from the group consisting of hydrogen, $C_{1-6}$-alkyl, and —$OR^{AX}$; $R^{6A}$ is selected from the group consisting of hydrogen, halogen, —$OR^{BX}$, $C_{6-10}$-aryl optionally substituted with one or more $C_{1-6}$-alkoxy, and $C_{6-10}$-aryl-$C_{2-6}$-alkynyl, wherein the $C_{6-10}$-aryl of the $C_{6-10}$-aryl-$C_{2-6}$-alkynyl is unsubstituted; $R^{11A}$ is hydrogen; $R^{13A}$ is selected from the group consisting of $C_{1-6}$-alkyl and $C_{6-10}$-aryl-$C_{1-6}$-alkyl, wherein the $C_{6-10}$-aryl of the $C_{6-10}$-aryl-$C_{1-6}$-alkyl is unsubstituted; and each $R^{17A}$ is hydrogen.

In one aspect, this disclosure provides a compound or salt thereof, wherein the compound has a structure corresponding to Formula (ID-1) or Formula (ID-2), or could be transformed to such structures by methods well known to those skilled in the art of synthetic organic chemistry:

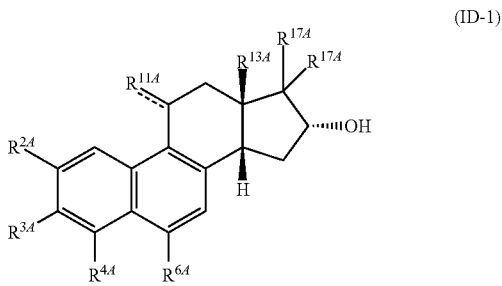

(ID-1)

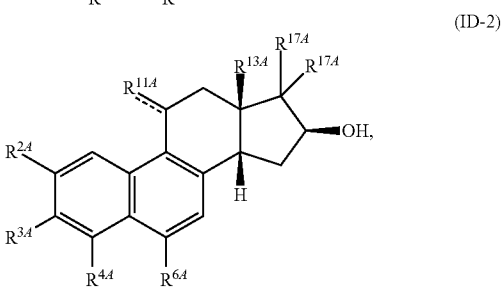

(ID-2)

wherein
each of $R^{2A}$ and $R^{4A}$ are independently selected from the group consisting of hydrogen, $C_{1-10}$-alkyl, $C_{2-10}$-alkenyl, $C_{2-10}$-alkynyl, $C_{1-10}$-haloalkyl, halogen, hydroxy, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;

$R^{3A}$ is selected from the group consisting of hydrogen, $C_{1-10}$-alkyl, $C_{2-10}$-alkenyl, $C_{2-10}$-alkynyl, $C_{1-10}$-haloalkyl, halogen, —$OR^{AX}$, —$SR^{AY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, and 5- to 10-membered heteroaryl;

$R^{6A}$ is selected from the group consisting of hydrogen, $C_{1-10}$-alkyl, $C_{2-10}$-alkenyl, $C_{2-10}$-alkynyl, $C_{1-10}$-haloalkyl, halogen, $OR^{BX}$, —$SR^{BY}$, —$S(O)_2NR^{Z1}R^{Z2}$, —$S(O)_2R^{Z1}$, —$S(O)R^{Z1}$, —$NR^{Z1}R^{Z2}$, —$N(R^{Z1})C(O)R^{Z2}$, —$N(R^{Z1})S(O)_2R^{Z2}$, $C_{6-10}$-aryl, 5- to 10-membered heteroaryl, $C_{6-10}$-aryl-$C_{1-6}$-alkyl, $C_{6-10}$-aryl-$C_{2-6}$-alkenyl, and $C_{6-10}$-aryl-$C_{2-6}$-alkynyl;

$R^{11A}$ is selected from the group consisting of hydrogen, oxygen, and $OR^{CX}$,
  wherein if $R^{11A}$ is oxygen, then ---- represents a double bond and if $R^{11A}$ is hydrogen or $OR^{CX}$, then ---- represents a single bond;
$R^{13A}$ is selected from the group consisting of $C_{1-6}$-alkyl and $C_{6-10}$-aryl-$C_{1-6}$-alkyl, wherein the $C_{6-10}$-aryl is optionally substituted one or more halogen, $C_{1-6}$-alkyl, $C_{1-6}$-haloalkyl, or $C_{1-6}$-alkoxy; and
each $R^{17A}$ is independently selected from the group consisting of hydrogen, $C_{1-10}$-alkyl, $C_{2-10}$-alkenyl, $C_{2-10}$-alkynyl, $C_{1-10}$-haloalkyl, and halogen;
  wherein any $C_{6-10}$-aryl or 5- to 10-membered heteroaryl is optionally substituted with one or more halogen, $C_{1-6}$-alkyl, $C_{1-6}$-haloalkyl, or $C_{1-6}$-alkoxy.

In certain embodiments, $R^{2A}$ and $R^{4A}$ each is independently selected from the group consisting of hydrogen, $C_{1-6}$-alkyl, halogen, hydroxy, and —$OR^{AX}$; $R^{3A}$ is selected from the group consisting of hydrogen, $C_{1-6}$-alkyl, and —$OR^{AX}$; $R^{6A}$ is selected from the group consisting of hydrogen, halogen, —$OR^{BX}$, $C_{6-10}$-aryl optionally substituted with one or more $C_{1-6}$-alkoxy, and $C_{6-10}$-aryl-$C_{2-6}$-alkynyl, wherein the $C_{6-10}$-aryl of the $C_{6-10}$-aryl-$C_{2-6}$-alkynyl is unsubstituted; $R^{11A}$ is hydrogen; $R^{13A}$ is selected from the group consisting of $C_{1-6}$-alkyl and $C_{6-10}$-aryl-$C_{1-6}$-alkyl, wherein the $C_{6-10}$-aryl of the $C_{6-10}$-aryl-$C_{1-6}$-alkyl is unsubstituted; and each $R^{17A}$ is hydrogen.

$R^{2A}$

In certain embodiments of any aspect disclosed herein, $R^{2A}$ is selected from the group consisting of hydrogen, $C_{1-6}$-alkyl, halogen, hydroxy, and —$OR^{AX}$, wherein $R^{AX}$ is $R^{AX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, —C(O)—O-$C_{1-10}$-alkyl, —C(O)—O-$C_{6-10}$-aryl, —C(O)—O-heteroaryl, —C(O)—$NR^{Z1}R^{Z2}$, —$S(O)_2R^{Z1}$, $C_{6-10}$-aryl, or 5- to 10-membered heteroaryl and wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy.

In some such embodiments, $R^{2A}$ is hydrogen. In some such embodiments, $R^{2A}$ is $C_{1-6}$-alkyl, including, but not limited to, methyl, ethyl, n-propyl, isopropyl, n-butyl, isobutyl, or tert-butyl. In some such embodiments, $R^{2A}$ is halogen, including, but not limited to, fluoro or chloro. In some such embodiments, $R^{2A}$ is hydroxy. In some such embodiments, $R^{2A}$ is —$OR^{AX}$.

$R^{3A}$

In certain embodiments of any aspect disclosed herein, $R^{3A}$ is selected from the group consisting of hydrogen, $C_{1-6}$-alkyl, and —$OR^{AX}$.

In some such embodiments, $R^{3A}$ is hydrogen. In some such embodiments, $R^{3A}$ is $C_{1-6}$-alkyl, including, but not limited to, methyl, ethyl, n-propyl, isopropyl, n-butyl, isobutyl, or tert-butyl. In some such embodiments, $R^{3A}$ is —$OR^{AX}$.

$R^{4A}$

In certain embodiments of any aspect disclosed herein, $R^{4A}$ is selected from the group consisting of hydrogen, $C_{1-6}$-alkyl, halogen, hydroxy, and —$OR^{AX}$, wherein $R^{AX}$ is $R^{AX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, —C(O)—O-$C_{1-10}$-alkyl, —C(O)—O-$C_{6-10}$-aryl, —C(O)—O-heteroaryl, —C(O)—$NR^{Z1}R^{Z2}$, —$S(O)_2R^{Z1}$, $C_{6-10}$-aryl, or 5- to 10-membered heteroaryl and wherein each of $R^{Z1}$ and $R^{Z2}$ are independently hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy.

In some such embodiments, $R^{4A}$ is hydrogen. In some such embodiments, $R^{4A}$ is $C_{1-6}$-alkyl, including, but not limited to, methyl, ethyl, n-propyl, isopropyl, n-butyl, isobutyl, or tert-butyl. In some such embodiments, $R^{4A}$ is halogen, including, but not limited to, fluoro or chloro. In some such embodiments, $R^{4A}$ is hydroxy. In some such embodiments, $R^{4A}$ is —$OR^{AX}$.

$R^{AX}$

In certain embodiments of any aspect disclosed herein, $R^{AX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, —C(O)—O-$C_{1-10}$-alkyl, —C(O)—O-$C_{6-10}$-aryl, —C(O)—O-heteroaryl, —C(O)—$NR^{Z1}R^{Z2}$, —$S(O)_2R^{Z1}$, $C_{6-10}$-aryl, or 5- to 10-membered heteroaryl.

In some such embodiments, $R^{AX}$ is $C_{1-6}$-alkyl. In some such embodiments, $R^{AX}$ is $C_{2-10}$-alkenyl. In some such embodiments, $R^{AX}$ is $C_{2-10}$-alkynyl. In some such embodiments, $R^{AX}$ is $C_{1-10}$-haloalkyl. In some such embodiments, $R^{AX}$ is, —C(O)-$C_{1-10}$-alkyl. In some such embodiments, $R^{AX}$ is —C(O)-$C_{6-10}$-aryl. In some such embodiments, $R^{AX}$ is —C(O)-heteroaryl. In some such embodiments, $R^{AX}$ is —C(O)—O-$C_{1-10}$-alkyl. In some such embodiments, $R^{AX}$ is —C(O)—O-$C_{6-10}$-aryl. In some such embodiments, $R^{AX}$ is —C(O)—O-heteroaryl. In some such embodiments, $R^{AX}$ is $C_{6-10}$-aryl. In some such embodiments, $R^{AX}$ is 5- to 10-membered heteroaryl. In some such embodiments, $R^{AX}$ is —C(O)—$NR^{Z1}R^{Z2}$. In some such embodiments, $R^{AX}$ is —$S(O)_2R^{Z1}$.

$R^{Z1}$

In certain embodiments of any aspect disclosed herein, $R^{Z1}$ is hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy.

In some such embodiments, $R^{Z1}$ is hydrogen. In some such embodiments, $R^{Z1}$ is $C_{1-6}$-alkyl. In some such embodiments, $R^{Z1}$ is $C_{2-10}$-alkenyl. In some such embodiments, $R^{Z1}$ is $C_{2-10}$-alkynyl. In some such embodiments, $R^{Z1}$ is $C_{1-10}$-haloalkyl. In some such embodiments, $R^{Z1}$ is $C_{6-10}$-aryl. In some such embodiments, $R^{Z1}$ is 5- to 10-membered heteroaryl. In some such embodiments, $R^{Z1}$ is hydroxy. In some such embodiments, $R^{Z1}$ is $C_{1-6}$-alkoxy.

$R^{Z2}$

In certain embodiments of any aspect disclosed herein, $R^{Z2}$ is hydrogen, $C_{1-6}$-alkyl, $C_{2-10}$-alkenyl, $C_{2-10}$-alkynyl, $C_{1-10}$-haloalkyl, $C_{6-10}$-aryl, 5- to 10-membered heteroaryl, hydroxy, or $C_{1-6}$-alkoxy.

In some such embodiments, $R^{Z2}$ is hydrogen. In some such embodiments, $R^{Z2}$ is $C_{1-6}$-alkyl. In some such embodiments, $R^{Z2}$ is $C_{2-10}$-alkenyl. In some such embodiments, $R^{Z2}$ is $C_{2-10}$-alkynyl. In some such embodiments, $R^{Z2}$ is $C_{1-10}$-haloalkyl. In some such embodiments, $R^{Z2}$ is $C_{6-10}$-aryl. In some such embodiments, $R^{Z2}$ is 5- to 10-membered heteroaryl. In some such embodiments, $R^{Z2}$ is hydroxy. In some such embodiments, $R^{Z2}$ is $C_{1-6}$-alkoxy.

$R^{6A}$

In certain embodiments of any aspect disclosed herein, $R^{6A}$ is selected from the group consisting of hydrogen, halogen, —$OR^{BX}$, $C_{6-10}$-aryl optionally substituted with one or more $C_{1-6}$-alkoxy, and $C_{6-10}$-aryl-$C_{2-6}$-alkynyl, wherein the $C_{6-10}$-aryl of the $C_{6-10}$-aryl-$C_{2-6}$-alkynyl is substituted or unsubstituted.

In some such embodiments, $R^{6A}$ is hydrogen. In some such embodiments, $R^{6A}$ is halogen. In some such embodiments, $R^{6A}$ is —$OR^{BX}$. In some such embodiments, $R^{6A}$ is unsubstituted $C_{6-10}$-aryl. In some such embodiments, $R^{6A}$ is $C_{6-10}$-aryl substituted with one or more $C_{1-6}$-alkoxy. In some such embodiments, $R^{6A}$ is $C_{6-10}$-aryl-$C_{2-6}$-alkynyl, wherein the $C_{6-10}$-aryl of the $C_{6-10}$-aryl-$C_{2-6}$-alkynyl is unsubstituted.

$R^{BX}$

In certain embodiments of any aspect disclosed herein, $R^{BX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl.

In some such embodiments, $R^{BX}$ is $C_{1-6}$-alkyl. In some such embodiments, $R^{BX}$ is $C_{2-10}$-alkenyl. In some such embodiments, $R^{BX}$ is $C_{2-10}$-alkynyl. In some such embodiments, $R^{BX}$ is $C_{1-10}$-haloalkyl. In some such embodiments, $R^{BX}$ is —C(O)-$C_{1-10}$-alkyl. In some such embodiments, $R^{BX}$ is —C(O)-$C_{6-10}$-aryl. In some such embodiments, $R^{BX}$ is —C(O)-heteroaryl. In some such embodiments, $R^{BX}$ is $C_{6-10}$-aryl. In some such embodiments, $R^{BX}$ is 5- to 10-membered heteroaryl.

$R^{11A}$

In certain embodiments of any aspect disclosed herein, $R^{11A}$ is selected from the group consisting of hydrogen, oxygen (double bonded to the C11 carbon atom), and $OR^{CX}$.

In some such embodiments, $R^{11A}$ is hydrogen. In some such embodiments, $R^{11A}$ is oxygen (double bonded to the C11 carbon atom). In some such embodiments, $R^{11A}$ is $OR^{CX}$.

$R^{CX}$

In certain embodiments of any aspect disclosed herein, $R^{CX}$ is $C_{1-6}$-alkyl, $C_{2-10}$-alkenyl, $C_{2-10}$-alkynyl, $C_{1-10}$-haloalkyl, —C(O)-$C_{1-10}$-alkyl, —C(O)-$C_{6-10}$-aryl, —C(O)-heteroaryl, $C_{6-10}$-aryl, or 5- to 10-membered heteroaryl.

In some such embodiments, $R^{CX}$ is $C_{1-6}$-alkyl. In some such embodiments, $R^{CX}$ is $C_{2-10}$-alkenyl. In some such embodiments, $R^{CX}$ is $C_{2-10}$-alkynyl. In some such embodiments, $R^{CX}$ is $C_{1-10}$-haloalkyl. In some such embodiments, $R^{CX}$ is —C(O)-$C_{1-10}$-alkyl. In some such embodiments, $R^{CX}$ is —C(O)-$C_{6-10}$-aryl. In some such embodiments, $R^{CX}$ is —C(O)-heteroaryl. In some such embodiments, $R^{CX}$ is $C_{6-10}$-aryl. In some such embodiments, $R^{CX}$ is 5- to 10-membered heteroaryl.

$R^{13A}$

In certain embodiments of any aspect disclosed herein, $R^{13A}$ is selected from the group consisting of $C_{1-6}$-alkyl and $C_{6-10}$-aryl-$C_{1-6}$-alkyl, wherein the $C_{6-10}$-aryl of the $C_{6-10}$-aryl-$C_{1-6}$-alkyl is substituted or unsubstituted.

In some such embodiments, $R^{13A}$ is $C_{1-6}$-alkyl. In some such embodiments, $R^{13A}$ is $C_{6-10}$-aryl-$C_{1-6}$-alkyl, wherein the $C_{6-10}$-aryl of the $C_{6-10}$-aryl-$C_{1-6}$-alkyl is unsubstituted. In some such embodiments, $R^{13A}$ is $C_{6-10}$-aryl-$C_{1-6}$-alkyl, wherein the $C_{6-10}$-aryl of the $C_{6-10}$-aryl-$C_{1-6}$-alkyl is substituted.

$R^{17A}$

In certain embodiments of any aspect disclosed herein, $R^{17A}$ is selected from the group consisting of hydrogen, $C_{1-10}$-alkyl, $C_{2-10}$-alkenyl, $C_{2-10}$-alkynyl, $C_{1-10}$-haloalkyl, and halogen.

In some such embodiments, $R^{17A}$ is hydrogen. In some such embodiments, $R^{17A}$ is $C_{1-10}$-alkyl. In some such embodiments, $R^{17A}$ is $C_{2-10}$-alkenyl. In some such embodiments, $R^{17A}$ is $C_{2-10}$-alkynyl. In some such embodiments, $R^{17A}$ is $C_{1-10}$-haloalkyl. In some such embodiments, $R^{17A}$ is halogen.

In one aspect, this disclosure provides a compound or salt thereof, wherein the compound has a structure corresponding to one of the following samnaunde.

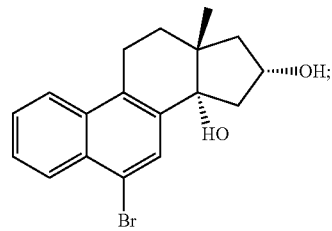
12

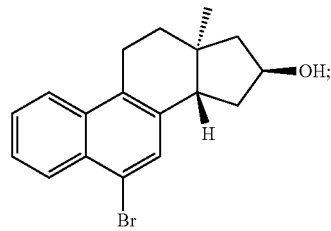
ent-12

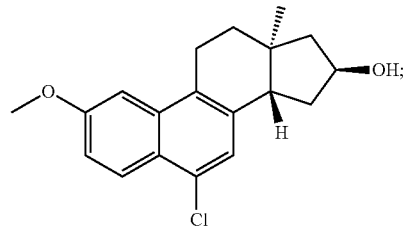
15

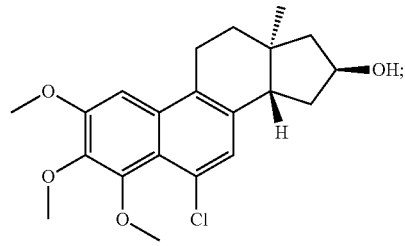
18

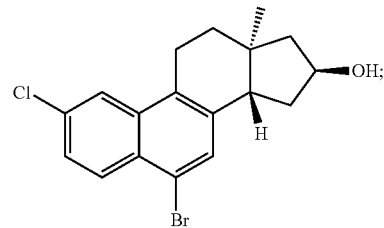
21a

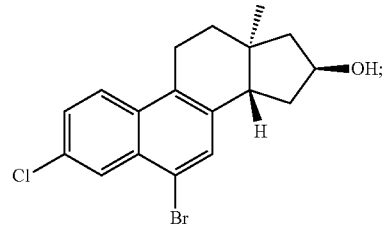
21b

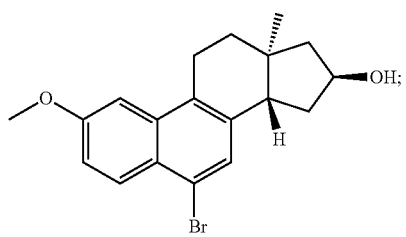
24
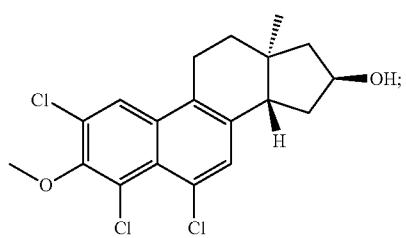
27
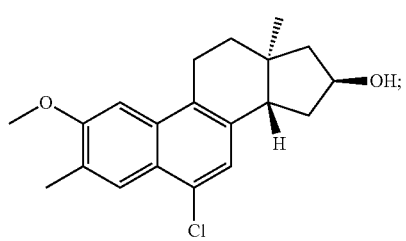
30
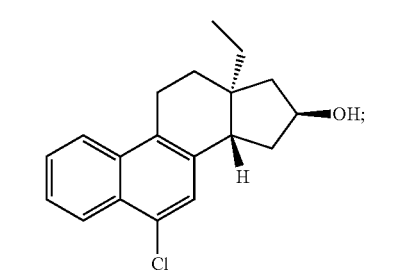
34
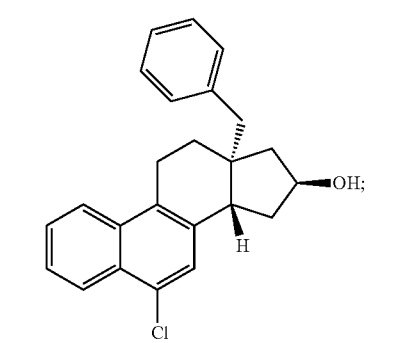
35
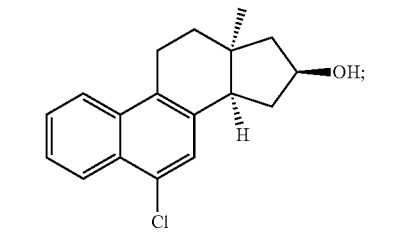
36
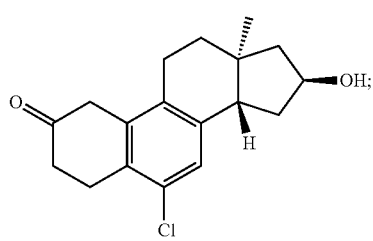
37
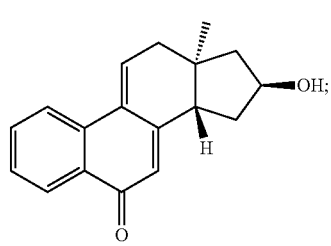
39
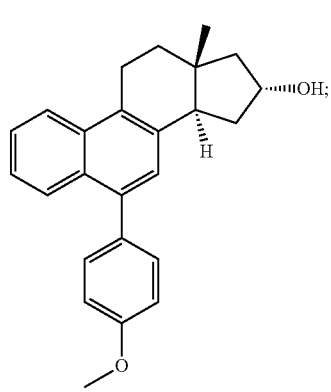
40
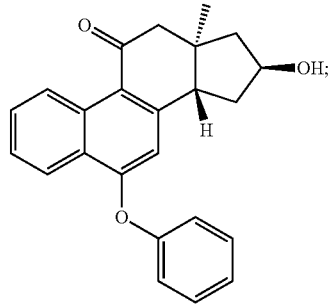
41
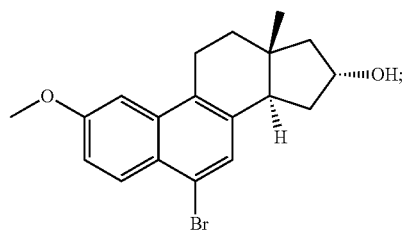
201a
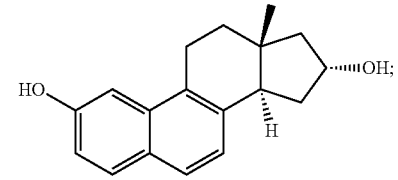
205b 201b
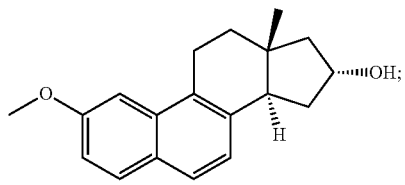
208b
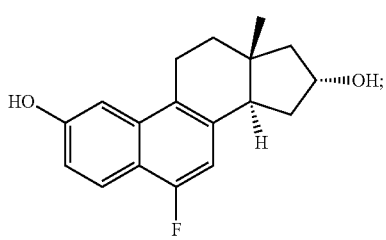
208a
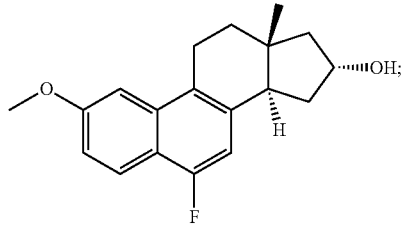
205c
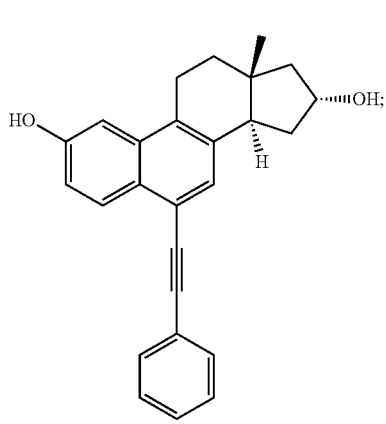
201c
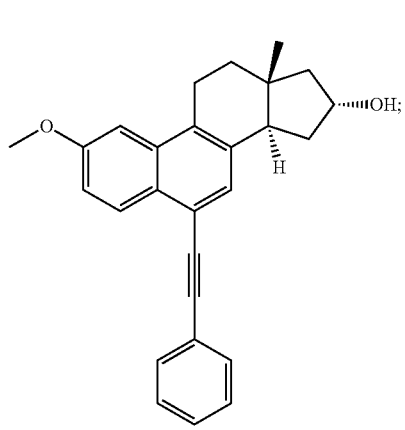
205a
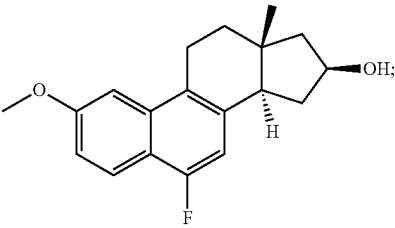
208c
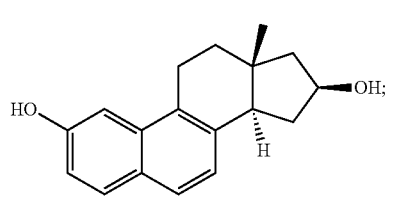
207b
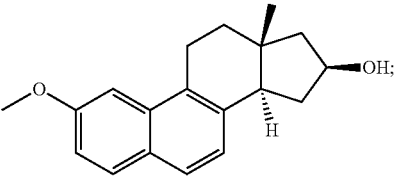
206b
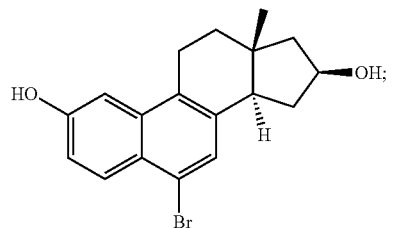
207a
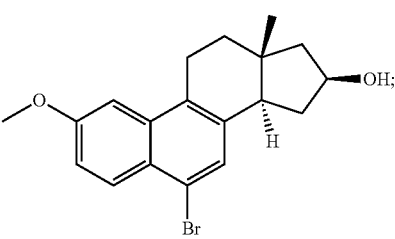
206a -continued

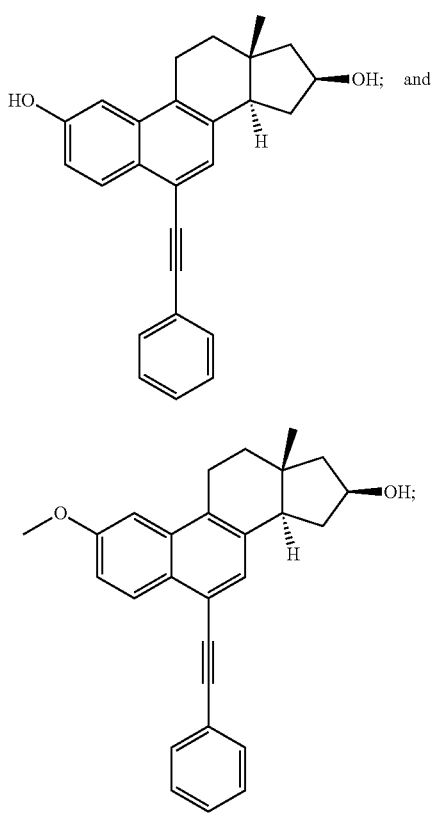

207c

206c

Figure 3A:
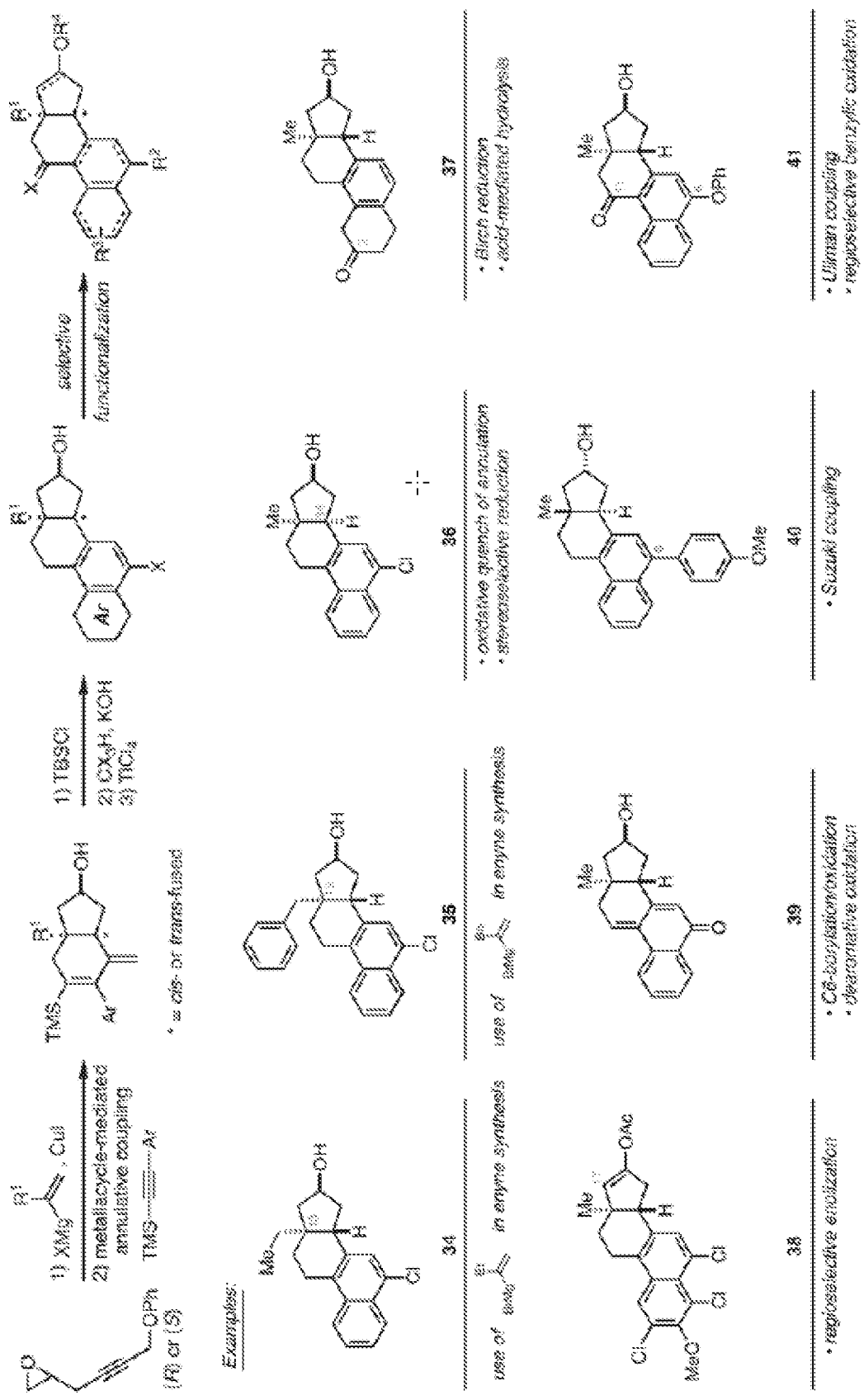
FIG. 3A shows production of several exemplary steroids with varying substitution and stereochemistry (e.g., steroidal compounds 34-41).

The present disclosure provides enantiospecific methods of producing steroids from readily available chiral starting materials that can be designed to comprise a range of steroidal systems (and semi-or partial-steroidal systems) preferentially further encompassing additional substitution(s) and varying stereochemistry. Notably, FIG. 3A and Example 2W (steroid 34), Example 2Y (steroid 35), Example 2Z (steroid 36), Example 3A (steroid 37), Example 4B (steroid 38), Example 5A (steroid 39), Example 6A (steroid 40), Example 7A (steroid 41), and FIG. 3C (steroids 27 and 43) among other embodiments, provide exemplary methods and resulting steroidal compositions encompassing varied additional substitution(s) and stereochemistries. Similarly, FIG. 3B and Example 8A (steroid ent-12) describe one embodiment of a method wherein multigram quantities of an enantiodefined steroidal product can be readily obtained.

Figure 3B:
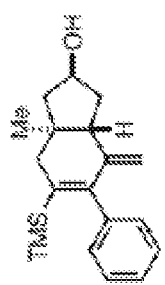
FIG. 3B shows a multigram-scale preparation of a synthetic ent-steroid (steroid ent-12).
Figure 3B:
Figure 3B:
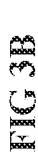

In steroidal products 34 and 35, the C13 quaternary center at the junction of rings C and D was altered simply by changing the Grignard reagent used to prepare the initial enyne for annulation ($R^1$=Et or Bn). In product 36, the stereochemistry at C14 was altered by using a variant of the metallacycle-mediated annulation process that furnishes the cis-fused isomer. (Kim, W. S., et al., Tetrahedron Lett., 56, 3557-3559 [2015]). Success here demonstrated that the relative stereochemistry of the CD-ring fusion (cis- or trans-fused) did not significantly impact the overall success of the steroid synthesis. Finally, simple functional group manipulations can be used to gain access to steroidal compositions possessing varied structure within each of the four rings of the tetracycle (steroid products 37-41). In one such embodiment, the present methods provide a means of producing a stable naphthoquinone methide (steroid 39). Finally, as depicted in FIG. 3B, the present synthesis methods and pathway are capable of producing multigram quantities of steroidal products. In one such exemplary embodiment, 4.0 g of steroid ent-12 was prepared in just five steps from epoxide 42 with an overall isolated yield of 20%.

Figure 3C:
FIG. 3C shows the preparation of ent-estra-1,3,5(10),6,8-pentaene-3,16α-diol.
Figure 3C:
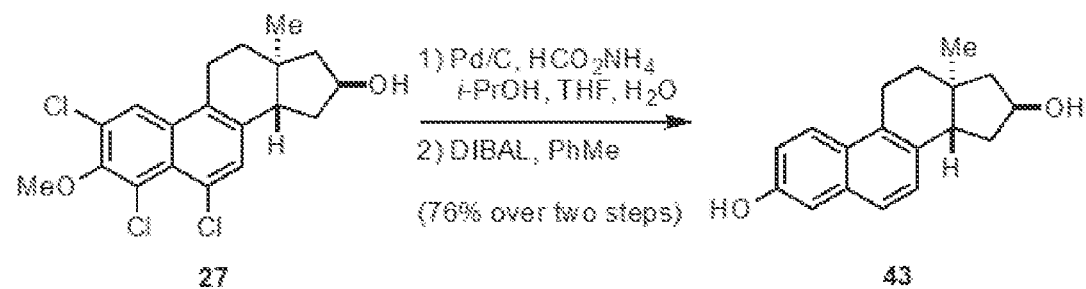

In still further embodiments, the present disclosure provides synthetic methods and pathways to produce ent-steroidal antipodes of medicinally relevant agents. For example, 16-hydroxyestratrienes have been identified as synthetic estrogens that have a dissociation in favor of their estrogenic action on bone rather than the uterus. (FIG. 3C). In one such example, while estra-1,3,5(10),6,8-pentaene-3,16α-diol is a representative member of this class, its enantiomer has never been described. Because the enantiomer of estradiol is known to have neurological activity of potential value for the treatment of traumatic brain injury, and lacks activity as an estrogenic compound, ent-estranes provide a broader class of steroidal compounds with useful "non-steroidal" pharmaceutical properties. More particularly, one of the products from this synthesis pathway (steroid 27) can be easily transformed to ent-estra-1,3,5(10),6,8-pentaene-3,16α-diol (steroid 43). (FIG. 3C).

In yet another embodiment, steroidal compound 39, a novel synthetic ent-steroid prepared using methods of the present disclosure, demonstrated marked growth inhibition in three human cancer cell lines with 50% inhibitory concentrations of 1.2-4 µM (0.32-1.07 µg/mL) ((FIG. 3D); cells were plated at 1000 cells/well of a 96 well plate. The following day, compound 39 was added in 2-fold dilutions (8 wells/concentration). After 7 days growth, cells were lysed and analyzed for total DNA content as previously described in Montano, R., et al., Mol Cancer Therap., 2012, 11, [427-438]).

D. Methods of Use

In at least one aspect, the present disclosure includes a method for treating or preventing a proliferative disease in a subject in need of such treatment or prevention. In certain embodiments, the subject is a mammal. In certain embodiments, the mammal is a human. The proliferative disease may be, for example, associated with: 1) the pathological proliferation of normally quiescent cells; 2) the pathological migration of cells from their normal location (e.g., metastasis of neoplastic cells); or 3) pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases. In particular, exemplary cancers that may treated or prevented include breast cancer, prostate cancer, ovarian cancer, acute myeloid leukemia, and glioma.

Another aspect of the present disclosure includes a method for treating or preventing schizophrenia in a subject in need of such treatment or prevention. In certain embodiments, the subject is a mammal. In certain embodiments, the mammal is a human.

Still another aspect of the present disclosure includes a method for treating or preventing neurodegeneration in a subject in need of such treatment or prevention. In certain embodiments, the subject is a mammal. In certain embodiments, the mammal is a human. In some such embodiments, the human subject is suffering from or at risk for a neurodegenerative disease such as spinal cord injury (SCI), multiple sclerosis (MS), Parkinson's disease (PD), and Alzheimer's disease (AD).

Yet another aspect of the present disclosure includes a method for treating or preventing neuropathic pain in a subject in need of such treatment or prevention. In certain embodiments, the subject is a mammal. In certain embodiments, the mammal is a human.

One aspect of the present disclosure includes a method for treating or preventing a disease mediated by ER-β in a subject in need of such treatment or prevention. In certain embodiments, the subject is a mammal. In certain embodiments, the mammal is a human.

Another aspect of the present disclosure includes a method for treating or preventing a disease treatable or preventable by selectively modulating ER-β in a subject in need of such treatment or prevention. In certain embodiments, the subject is a mammal. In certain embodiments, the mammal is a human.

In certain embodiments, for any of the aforementioned aspects, the methods comprise administering to the subject a therapeutically effective amount of a compound of Formula (I) or a pharmaceutically acceptable salt thereof. In some such embodiments, the methods comprise administering to the subject a therapeutically effective amount of a compound of Formula (IA) or a pharmaceutically acceptable salt thereof. In some such embodiments, the methods comprise administering to the subject a therapeutically effective amount of a compound of Formula (IB) or a pharmaceutically acceptable salt thereof. In some such embodiments, the methods comprise administering to the subject a therapeutically effective amount of a compound of Formula (IC) or a pharmaceutically acceptable salt thereof. In some such embodiments, the methods comprise administering to the subject a therapeutically effective amount of a compound of Formula (ID) or a pharmaceutically acceptable salt thereof. In some such embodiments, the methods comprise administering to the subject a therapeutically effective amount of Compound 39 or a pharmaceutically acceptable salt thereof. In some such embodiments, the methods comprise administering to the subject a therapeutically effective amount of Compound 205b or a pharmaceutically acceptable salt thereof.

In certain embodiments, for any of the aforementioned aspects, the methods comprise administering to the subject a therapeutically effective amount of a compound of Formula (II) or a pharmaceutically acceptable salt thereof.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). In certain embodiments, dosage unit compositions contain such amounts or submultiples thereof to make up the daily dose. In many instances, the administration of the compound or salt will be repeated a plurality of times. In certain embodiments, multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

The activity of a compound can be determined using various known methods. For example, the anti-proliferative activity of a compound can be determined using various known methods, including in vitro and in vivo antiproliferative assays using cancer cell lines such as MDA-MB-231 (human breast adenocarcinoma), AsPC-1 (human pancreas adenocarcinoma ascites metastasis), and A549 (lung carcinoma).

In at least one aspect, the present disclosure provides methods for producing one or more steroids of the natural enantiomeric configuration. Natural steroids, in these specific embodiments, are taken as being medically, pharmaceutically, or biologically relevant steroids otherwise produced by steroidogenesis in nature (i.e., in an animal, fungus, or plant). In preferred embodiments, the present disclosure provides methods for concise and enantiospecific synthesis of nat- and/or ent-steroid species comprising (or chemically related to) a licensed steroid drug product and/or active ingredient (e.g., licensed by recognized regulatory agency or body such as, but not limited to, the: Food and Drug Administration ("FDA"), European Medicines Agency ("EMA"), The Therapeutic Goods Administration ("TGA"), China Food and Drug Administration ("CFDA"), The Central Drugs Standard Control Organization ("CDSCO"), National Institute of Health Sciences ("NIHS"), Ministry of Food and Drug Safety ("MFDS") and the like), and derivatives, isomers, precursors, and/or enantiomers thereof, at research and/or production scale quantities.

In still further embodiments, the present disclosure provides nat- and/or ent-steroid compositions that are medically useful by themselves or as incorporated into medicinal formulations to treat, prevent, and/or cure, a range of diseases and medical conditions related to, but not limited to, cancers, tumors, and other hyper-proliferative diseases, cardiovascular diseases, inflammation, pain, autoimmune diseases and disorders (e.g., Crohn's disease, ulcerative colitis, psoriasis, psoriatic arthritis, juvenile arthritis and ankylosing spondilitis, autoimmune diabetes, multiple sclerosis, systemic lupus erythematosus, rheumatoid spondylitis, gouty arthritis, allergy, autoimmune uveitis, nephrotic syndrome, multisystem autoimmune diseases, autoimmune hearing loss, adult respiratory distress syndrome, shock lung, chronic pulmonary inflammatory disease, pulmonary sarcoidosis, pulmonary fibrosis, silicosis, idiopathic interstitial lung disease, chronic obstructive pulmonary disease, asthma, restenosis, spondyloarthropathies, Reiter's syndrome, autoimmune hepatitis, inflammatory skin disorders, vasculitis of large vessels, medium vessels or small vessels, endometriosis, prostatitis and Sjogren's syndrome, and the like), and brain injuries, including trauma both physical and chemically induced, among other diseases, and as import chemical precursors for additional steroid derivatives. In still other embodiments, the present disclosure provides steroid compositions and steroid based compositions useful for regulating growth and or reproductive function/dysfunction in an organism (e.g., estrogen, progesterone, testosterone, pregnenolone, and the like).

The present disclosure further contemplates that certain nat- and/or ent-steroidal compositions provided herein are useful analytes (ligands) in studies to understand steroid-membrane receptor interactions from a mechanistic as well as an applied drug discovery and development point of view. More particularly, it is contemplated that the present compositions are useful in studies to differentiate steroid-membrane receptor interactions from other intercellular and intracellular steroid-receptor interactions (e.g., steroid-nuclear receptor interactions). Even more particularly, certain steroid compositions of the present disclosure are useful in mechanistic studies aimed at distinguishing the direct effects of steroid-membrane receptor interaction(s) (e.g., binding the receptor of interest) from indirect effects resulting from steroid caused membrane perturbation(s) (e.g., alteration of the membrane environment).

The novel ent-steroids of the present disclosure (e.g., mirror images of naturally occurring steroids) are useful tools for distinguishing between various actions of steroids in membranes and/or receptor-mediated signaling pathways.

While the present disclosure is not limited to any particular mechanism(s) or mode(s) of action, it is contemplated that the nat- and ent-steroids made using the methods of the present disclosure can be used in studies/assays designed to differentiate the direct and indirect effects of steroids on membrane receptor function. Enantiomeric steroids (i.e., the nat- and ent-steroids) are mirror images of one another that share identical physicochemical properties. It is further contemplated, that since steroid receptor binding pockets are typically well-defined and structurally maintained, one enantiomeric ligand (e.g., the nat-steroid enantiomer) will preferentially bind to the receptor in comparison to the other enantiomer (e.g., the ent-steroid enantiomer). It is understood that ligand-receptor binding (in the case of steroid enantiomers) is enantioselective (i.e., one enantiomer will bind more effectively than the other enantiomer). Excluding the steroid-receptors, the remaining membrane constituents (e.g., lipids (phospholipids, glycolipids, and sterols), proteins, and carbohydrates) exist in a dynamic environment. It is further contemplated that the steroid's physiochemical properties will be more important in affecting the membrane than its enantiomeric configuration (i.e., nat- versus ent-). In other words, both nat- and ent-steroids are contemplated to have nearly equivalent (non-enantioselective) effects on the membrane. Accordingly, the direct steroid-receptor binding effects as well as the indirect effects of steroid caused membrane perturbation should be distinguishable by measuring the differences in steroid-receptor enantioselectivity. (See, Biellmann, J. F., Chem. Rev., 103, 2019-2033 [2003]; Covey, D. F., Steroids, 74(4):577-585 [2009]). Nevertheless, certain ent-steroids are, or nearly are, as effective as their nat-steroid counterpart at modulating protein function.

Various compositions of the present disclosure are useful for modulating (e.g., increasing or decreasing the activity or function thereof) particular membrane protein targets (e.g., steroid receptors). Those skilled in the art will appreciate that certain steroidal compositions produced according to the present disclosure can be characterized and/or classified according to the rapid non-genomic actions of steroids and the Mannheim Classification. (See, Falkenstein, E., et al., J. Clin. Endocrinol. Metab., 85, 2072-2075 [2000]; Losel, R., and Wehling, M., Nat. Rev. Mol. Cell Biol., 4, 46-56 [2003]; and Wehling, M., and Losel, R., J. Steroid Biochem. Mol. Biol., 102, 180-183 [2006]).

The nat- and ent-steroidal compositions of the present disclosure are not contemplated to be limited to interactions only with target steroid membrane receptors, indeed, other biological macro-/molecules are known to interact (e.g., bind) with steroids including, but not limited to, enzymes, receptors, transporters, antibodies, peptides (e.g., poly-, proteins), lipids, saccharides (e.g., mono-, di-, oligo-, poly-saccharides), nucleotides (e.g., mono-, di-, oligo-, poly-nucleotides), biomimetics, and the like.

E. Compositions

In at least one aspect, the present disclosure includes compositions comprising a compound described herein or a salt thereof. In certain embodiments, the composition comprises a compound of Formula (I) or a salt thereof. In certain embodiments, the composition comprises a compound of Formula (IA) or a salt thereof. In certain embodiments, the composition comprises a compound of Formula (IB) or a salt thereof. In certain embodiments, the composition comprises a compound of Formula (IC) or a salt thereof. In certain embodiments, the composition comprises a compound of Formula (ID) or a salt thereof. In certain embodiments, the composition comprises a compound of Formula (II) or a salt thereof.

In certain embodiments, the composition comprises one or more conventional pharmaceutically acceptable carriers. Pharmaceutically acceptable carriers include, without limitation, a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations. Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

In at least one aspect, the present disclosure includes pharmaceutical compositions comprising a therapeutically effective amount of a compound described herein in combination with one or more pharmaceutically acceptable carriers. In certain embodiments, the pharmaceutical compositions comprise a compound of formula (I) or a salt thereof formulated together with one or more pharmaceutically acceptable carriers. In certain embodiments, the pharmaceutical compositions comprise a compound of formula (IA) or a salt thereof formulated together with one or more pharmaceutically acceptable carriers. In certain embodiments, the pharmaceutical compositions comprise a compound of formula (IB) or a salt thereof formulated together with one or more pharmaceutically acceptable carriers. In certain embodiments, the pharmaceutical compositions comprise a compound of formula (IC) or a salt thereof formulated together with one or more pharmaceutically acceptable carriers. In certain embodiments, the pharmaceutical compositions comprise a compound of formula (ID) or a salt thereof formulated together with one or more pharmaceutically acceptable carriers. In certain embodiments, the pharmaceutical compositions comprise a compound of formula (II) or a salt thereof formulated together with one or more pharmaceutically acceptable carriers.

The pharmaceutical compositions may be formulated for any route of administration. The pharmaceutical compositions can be administered to humans and other animals orally, nasally, rectally, parenterally, intracisternally, intravaginally, intraperitoneally, topically (as by powders, ointments or drops), or bucally. The term "parenterally", as used herein, refers to modes of administration which include intravenous, intramuscular, intraperitoneal, intrasternal, subcutaneous, intraarticular injection and infusion.

In certain embodiments, the pharmaceutical compositions are formulated for oral administration in solid or liquid form.

In certain embodiments, the pharmaceutical composition is a solid dosage form for oral administration. Solid dosage forms for oral administration include capsules, tablets, pills, powders, and granules. In certain embodiments, the pharmaceutical composition includes, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. In certain embodiments, the pharmaceutical composition is tableted or encapsulated for convenient administration. In certain embodiments, such capsules or tablets contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

In certain embodiments, the pharmaceutical composition is a liquid dosage form for oral administration. Liquid dosage forms for oral administration include, for example, pharmaceutically acceptable emulsions (including both oil-in-water and water-in-oil emulsions), solutions (including both aqueous and non-aqueous solutions), suspensions (including both aqueous and non-aqueous suspensions), syrups, and elixirs. In certain embodiments, the liquid dosage forms contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. In addition, in certain embodiments, oral compositions, also include wetting, emulsifying, suspending, flavoring (e.g., sweetening), and/or perfuming agents.

In certain embodiments, the pharmaceutical composition is for parenteral administration. In certain embodiments, formulations for parenteral administration are prepared from sterile powders or granules having one or more of the carriers or excipients mentioned for use in the formulations for oral administration. In certain embodiments, a compound or salt thereof is dissolved in water, polyethylene glycol, propylene glycol, ethanol, corn oil, cottonseed oil, peanut oil, sesame oil, benzyl alcohol, sodium chloride, and/or various buffers. In certain embodiments, the pH is adjusted, if necessary, with a suitable acid, base, or buffer.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

In certain embodiments, the pharmaceutical composition is for rectal or vaginal administration. Compositions for rectal or vaginal administration are preferably suppositories that can be prepared by, for example, mixing a compound or salt thereof with a suitable nonirritating carrier or excipient that is solid at ordinary room temperatures, but liquid at body temperature. Suitable carriers or excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other carriers and modes of administration known in the pharmaceutical art also may be used.

In certain embodiments, the compounds are used in the form of pharmaceutically acceptable salts or esters, or amides derived from inorganic or organic acids. In certain embodiments, pharmaceutically acceptable salts are those salts that are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the field. The salts can be prepared in situ during the final isolation and purification of the present compounds or separately by, for example, reacting a free base function with a suitable organic acid.

Representative pharmaceutically acceptable salts include, but are not limited to, acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

In certain embodiments, pharmaceutically acceptable acid addition salts of the compounds of Formula (I), (IA), (IB), (IC), (ID), or (II) are prepared from an inorganic or organic acid. Examples of acids which can be employed to form pharmaceutically acceptable acid addition salts include inorganic acids such as hydrochloric acid, hydrobromic acid, sulphuric acid and phosphoric acid and organic acids such as acetic acid, oxalic acid, maleic acid, succinic acid, tartaric acid, and citric acid. In certain embodiments, a weak acid, including, but not limited to, tartaric acid, lactic acid, acetic acid, propionic acid, citric acid, malic acid, and the like, can be employed to form pharmaceutically acceptable acid addition salt.

In certain embodiments, pharmaceutically acceptable base addition salts of the compounds of Formula (I), (IA), (IB), (IC), (ID), or (II) include, for example, metallic salts and organic salts. In certain embodiments, pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

In certain embodiments, at least 50% of the composition comprises a compound of Formula (I), (IA), (IB), (IC), (ID), (II), or a salt thereof. In certain embodiments, at least 60% of the composition comprises a compound of Formula (I), (IA), (IB), (IC), (ID), (II), or a salt thereof. In certain embodiments, at least 70% of the composition comprises a compound of Formula (I), (IA), (IB), (IC), (ID), (II), or a salt thereof. In certain embodiments, at least 80% of the composition comprises a compound of Formula (I), (IA), (IB), (IC), (ID), (II), or a salt thereof. In certain embodiments, at least 90% of the composition comprises a compound of Formula (I), (IA), (IB), (IC), (ID), (II), or salt thereof. In certain embodiments, at least 95% of the composition comprises a compound of Formula (I), (IA), (IB), (IC), (ID), (II), or a salt thereof.

In one aspect, the present disclosure includes a pharmaceutical composition comprising a compound or a pharmaceutically acceptable salt describered herein and a pharmaceutically acceptable excipient.

F. Additional Formulation, Administration, and Dosing Considerations

The practice of the present disclosure will employ, unless otherwise indicated, conventional techniques of preparing pharmaceutical formulations as well as drug delivery and dosing techniques which are well known in the art.

Generally speaking, the methods and compositions of the present disclosure provides treatments suitable for populations of cells (e.g., tissues, organs, structures, and the like) in a subject (e.g., animal or human), in order to confer a medicinal or therapeutic benefit to that population, by the administration of an effective dose of the one or more of compound described herein. In some cases, the plasma/blood/serum/urine or otherwise provided concentrations of the administered compounds is less than or greater than about 100 µM, 10 µM, 1 µM, 500 nM, 100 nM, 10 nM, or even 1 nM (i.e., from about 0.1 nM to about 1 nM), however, the physician will be able to determine effective dosing concentrations, patterns, and administration routes upon consideration to the subject's age, sex, weight, health status, and other relevant physical, biochemical, genetic, factors, conditions, and the like.

In some embodiments, the concentration of one or more of the compounds provided in the pharmaceutical compositions of the present disclosure is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In yet some other embodiments, the concentration of one or more of the compounds of the present disclosure is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In still some other embodiments, the concentration of one or more of the compounds of the present disclosure is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds of the present disclosure is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some other embodiments, the amount of one or more of the compounds of the present disclosure is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds of the present disclosure is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

Other embodiments provide, amounts of one or more of the compounds of the present disclosure in the range of 0.0001-10 g, 0.0005-9 g, 0.001-8 g, 0.005-7 g, 0.01-6 g, 0.05-5 g, 0.1-4 g, 0.5-4 g, or 1-3 g.

More particularly, one or more compositions of the present disclosure may be administered in any suitable amount(s), and in the order disclosed herein. In some embodiments, a first composition (first agent) is administered to a subject within a range of about 0.1 mg/kg-50 mg/kg per day, such as about, less than about, or more than about, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, or 50 mg/kg per day. In some embodiments, a composition is administered to a subject within a range of about 0.1 mg/kg-400 mg/kg per week, such as about, less than about, or more than about 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 100 mg/kg, 150 mg/kg, 200 mg/kg, 250 mg/kg, 300 mg/kg, 350 mg/kg, or 400 mg/kg per week. In some embodiments, a first agent is administered to a subject within a range of about 0.1 mg/kg-1500 mg/kg per month, such as about, less than about, or more than about 50 mg/kg, 100 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, or 1000 mg/kg per month. In some embodiments, a first agent is administered to a subject within a range of about 0.1 mg/m$^2$-200 mg/m$^2$ per week, such as about, less than about, or more than about 5 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 100 mg/m m$^2$, 125 mg/m$^2$, 150 mg/m$^2$, 175 mg/m$^2$, or 200 mg/m$^2$ per week. The target dose may be administered in a single dose. Alternatively, the target dose may be administered in about or more than about 1, 2, 3, 4, 5, 6, 7, 8, 9, 10, 11, 12, 13, 14, 15, 16, 17, 18, 19, 20, 25, 30, or more doses. For example, a dose of about 20 mg/kg per week may be delivered weekly at a dose of about 20 mg/kg, or may be delivered at a dose of about 6.67 mg/kg administered on each of three days over the course of the week, which days may or may not be consecutive. The administration schedule may be repeated according to any prescribed regimen, including any administration schedule described herein. In some embodiments, a first agent is administered to a subject in the range of about 0.1 mg/m$^2$-500 mg/m m$^2$, such as about, less than about, or more than about 5 mg/m$^2$, 10 mg/m$^2$, 15 mg/m$^2$, 20 mg/m m$^2$, 25 mg/m$^2$, 30 mg/m$^2$, 35 mg/m m$^2$, 40 mg/m m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 100 mg/m$^2$, 130 mg/m$^2$, 135 mg/m$^2$, 155 mg/m$^2$, 175 mg/m$^2$, 200 mg/m$^2$, 225 mg/m$^2$, 250 mg/m$^2$, 300 mg/m$^2$, 350 mg/m$^2$, 400 mg/m$^2$, 420 mg/m m$^2$, 450 mg/m$^2$, or 500 mg/m m$^2$.

The compositions disclosed herein may be administered in one dose or multiple dosages. Methods of determining the most effective means and dosage of administration are well known to those of skill in the art and will vary with the composition used for therapy, the purpose of the therapy, the target cell or tissue being treated, and the subject being treated. Single or multiple administrations (e.g., about or more than about 1, 2, 3, 4, 5, 6, 7, 8, 9, 10, 11, 12, 13, 14, 15, 16, 17, 18, 19, 20, 25, 30, or more doses) can be carried out with the dose level and pattern being selected by the treating physician. It is known in the art that due to inter-subject variability in compound pharmacokinetics, individualization of dosing regimen is necessary for optimal therapy. Dosing for composition of the invention may be found by routine experimentation in light of the instant disclosure and one's skill in the art.

A first agent composition of the invention may be mixed with one or more other drug substance(s) (e.g., a second agent, a third agents, etc.) in a fixed pharmaceutical composition or it may be administered separately, before, simultaneously with or after the one or more other drug substance(s).

Administration of any of the compounds disclosed herein may be achieved by means standard in the art, and may include the use of a single compound or a mixture of two or more compounds, their enantiomers or diastereomers, or pharmaceutically acceptable salts, and other pharmaceutical preparations thereof.

Administration of the compounds disclosed herein can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g., transdermal application), rectal administration, via local delivery by catheter or stent or through inhalation. Compounds can also be administered intraadiposally or intrathecally. An effective amount of an inhibitor of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. Sequential administration of a first composition and/or any additional therapeutic agent can be effected by any appropriate route as noted above and including, but not limited to, oral routes, intravenous routes, intramuscular routes, and direct absorption through mucous membrane tissues. The therapeutic agents can be administered by the same route or by different routes. For example, a first composition (therapeutic agent) of the combination selected may be administered by intravenous injection while the other therapeutic agents of the combination may be administered orally. Alternatively, for example, all therapeutic agents may be administered orally or all therapeutic agents may be administered by intravenous injection. Methods of administering the compounds of the invention may be by metered dose or by one or more controlled release devices.

Additionally, it is to be noted that, similar to the approaches described in the fields of medicinal and pharmaceutical chemistry, a suitable pharmaceutical preparation may also include, optionally, in addition to one or more compounds disclosed herein, other agents, including, but not limited to, excipients, diluents, extenders, stabilizers, colors, flavors, formulating agents (e.g., talc, minerals, and other press-able powders), encapsulating agents (e.g., enteric coatings), antioxidants, preservatives, sterile aqueous solutions, buffers, sugars, and the like, as are generally known and accepted.

Additionally, subject pharmaceutical compositions may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and an inhibitor according to the invention as an active ingredient. In addition, it may include other medicinal or pharmaceutical agents, carriers, adjuvants, etc.

Generally speaking, the compounds disclosed herein may be prepared by means standard in the art. A number of standard text are known in the art regarding preparation and formulation considerations. (See e.g., Remington's Pharmaceutical Sciences).

In other embodiments, one or more additional small molecule drug and/or biological agents may be preferentially combined with the one or more compounds disclosed herein to achieve a beneficial, or even synergistic, outcome in the subject.

The present compounds are suitable, for example, in treating subjects suffering from trauma, chronic degenerative diseases or acute disease such as induced by an ischemic attack. Specific examples include Alzheimer's disease, Parkinson's disease, stroke, ischemia, heart attack or angioplasty, or brain or spinal cord trauma, hypoglycemia, anoxia, burns or surgeries that result in the loss of nutrient flow to the tissues. Other diseases that may be treatable with compounds of the current invention include, but are not limited to: heart disease, including, but not limited to, restenosis, atherosclerosis, myocardial infarction, ophthalmologic diseases, including, but not limited to, macular degeneration, lens or retinal degeneration, formation of cataracts and glaucoma, alcoholism, alcohol withdrawal, drug-induced seizures vascular occlusion, epilepsy, cerebral vascular hemorrhage, hemorrhage; environmental excitotoxins, dementias, drug-induced brain damage and other systemic or acute degenerative diseases characterized by necrotic or apoptotic cell death. To-date, there are no known cures and few therapies that slow the progression of many diseases.

Certain embodiments of the present disclosure may further be applied to the procedure of tissue transplantation, prior, during or after removal or reperfusion of cells, tissues or organs or during storage of the cells, tissues or organs and is applicable to any of the cells in the body.

In some embodiments, the subject is a human in need of treatment for cancer, or a precancerous condition or lesion. Subjects that can be treated with a compound or pharmaceutically acceptable salt, ester, prodrug, solvate, hydrate or derivative thereof, according to the methods of this disclosure include, for example, subjects that have been diagnosed as having renal cell carcinoma, unresectable hepatocellular carcinoma, or thyroid carcinoma, breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheloid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma. malignant meningioma, malignant mesothelioma, and malignant mixed Mullerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer, and the like.

Detection, monitoring, and rating of various cancers in a human are further described in Cancer Facts and Figures 2001, American Cancer Society, New York, N.Y., and International Patent Application WO 01/24684. Accordingly, a physician can use standard tests to determine the efficacy of the various embodiments of the inventive compositions and methods in treating cancer. However, in addition to tumor size and spread, the physician also may consider quality of life and survival of the subject in evaluating efficacy of treatment.

Certain compounds disclosed herein are also useful as co-therapeutic compounds for use in combination with other drug substances, for example, but not limited to, agents such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. Suitable antihistamine drug substances include cetirizine hydrochloride, acetaminophen, clemastine fumarate, promethazine, loratidine, desloratadine, diphenhydramine and fexofenadine hydrochloride, activastine, astemizole, azelastine, ebastine, epinastine, mizolastine and tefenadine, and the like. Other useful combinations of compounds of the invention with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as antagonists SC-351 125, SCH-55700 and SCH-D, antagonists such as TAK-770, and CCR-5 antagonists. The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs) (e.g., acetylsalicylic acid, ibuprofen, naproxen, indomethacin, nabumetone, tolmetin, and the like). Corticosteroids are used to reduce inflammation and suppress activity of the immune system.

The activity of the compounds disclosed herein may be determined by means standard in the art.

The compounds, compositions, and methods described herein will be better understood by reference to the following examples, which are included as an illustration of and not a limitation upon the scope of the invention.

G. Exemplary Embodiments

In one aspect, the present disclosure provides a steroid composition according to a method for the present disclosure. In certain embodiments, the steroid is an ent-steroid. In some such embodiments, the ent-steroid has a structure corresponding to Formula (II). In some such embodiments, the ent-steroid is Compound 39.

In another aspect, the present disclosure provides a method for making ent-steroids according to the present disclosure.

In yet another aspect, the present disclosure provides a steroid composition according to a method for the present disclosure. In certain emodiments, the steroid is a nat-steroid. In some such emodiments, the nat-steroid is Compound 205b.

It will be readily apparent to those skilled in the art that other suitable modifications and adaptations of the compositions and methods of the invention described herein are obvious and may be made using suitable equivalents without departing from the scope of the invention or the embodiments disclosed herein.

Having now described the present invention in detail, the same will be more clearly understood by reference to the following examples, which are included for purposes of illustration only and are not intended to limit the invention.

H. EXAMPLES

General Materials and Methods

1. Reagents and Solvents.

All reactions were conducted in flame-dried glassware under a nitrogen atmosphere with dry solvents, unless otherwise noted. All reagents and starting materials were purchased from commercial sources and used as supplied, unless otherwise indicated.

Anhydrous diethyl ether ($Et_2O$), dimethylformamide (DMF), tetrahydrofuran (THF), toluene (PhMe), methylene chloride ($CH_2Cl_2$) were obtained by the Glass Contour Solvent Purification System. Anhydrous methanol (MeOH) was purchased in a Sure-Seal™ bottle from Sigma-Aldrich. Solutions of n-BuLi (2.5 M in hexanes) were purchased from Sigma-Aldrich and titrated against N-benzylbenzamide in accordance with the procedure reported by Burchat, A. F.; Chong, J. M.; Nielsen, N. *J. Organomet. Chem.* 1997, 542, 281-283.

For flash column chromatography, HPLC grade solvents were used without further purification.

2. Reaction Set-Up and Purification

Reaction mixtures were magnetically stirred and their progress was monitored by thin layer chromatography (TLC) on EMD TLC silica gel 60 $F_{254}$ glass-backed plates. Compounds were visualized by UV-light (254 nm) or an aqueous solution of phosphomolybdic acid, ceric sulfate, and sulfuric acid (EMD Millipore, Billerica, MA, USA).

Purification of crude isolates was achieved by flash column chromatography on a BIOTAGE ISOLERA ONE Automated Liquid Chromatography System using silica gel cartridges (Biotage, Charlotte, NC, USA) or performed using a forced flow of the indicated solvent system on SORBENT TECHNOLOGIES silica gel 60 Å (40-63 µm particle size). Concentration of reaction product solutions and chromatography fractions was accomplished by rotary evaporation at 30-35° C. under the appropriate pressure, followed by concentration at room temperature on a vacuum pump (approx. 0-1 mbar). Yields refer to chromatographically purified and spectroscopically pure compounds, unless otherwise indicated.

3. Compound Characterization $^1H$ NMR data were recorded on Bruker Avance III 500 and 600 MHz spectrometer (TBI probe). $^{13}C$ NMR data were recorded at 125 MHz and 150 MHz on Bruker Avance III 500 and 600 MHz spectrometer (TBI probe). Infrared spectra were recorded on a JASCO FT/IRM4100 Fourier Transform Infrared Spectrometer. Optical rotations were measured with a JASCO DIP-370 and JASCO P-2000 polarimeter. HRMS (ESI or EI) analyses were performed at the Mass Spectrometry Laboratory of University of Illinois at Urbana-Champaign. All compounds purified by chromatography were sufficiently pure for use in further experiments, unless indicated otherwise.

Optical rotations (α) were obtained on a JASCO-P-2000 polarimeter equipped with tungsten-halogen lamp (WI) and interface filter set to 589 nm, using a sample cell with a pathlength of 100 nm. Specific rotations are reported as: $[\alpha]_{589}^{T(°C.)}$ (c, solvent) and are based on the equation $[\alpha]_{589}^{T(°C.)} = (100 \cdot \alpha)/(l \cdot c)$, where the concentration (c) is reported as g/100 ml and the pathlength (l) in decimeters.

Example 1

General Synthetic Procedures, Preparation of Reaction Intermediates (R)-epichlorohydrin 5 and (S)-epichlorohydrin ent-5 were purchased from Chem Impex. Alkyne 7, alkyne 19, alkyne 22, and anhydrous methanol (MeOH) were purchased from Sigma-Aldrich, St. Louis, MO, USA. Chloroform ($CHCl_3$) and bromoform ($CHBr_3$) were purchased from Alfa Aesar, Tewksbury, MA, USA. Titanium isopropoxide ($Ti(Oi-Pr)_4$), and nitromethane ($MeNO_2$) were purchased from Acros Organics (Pittsburgh, PA, USA), and titanium isopropoxide was distilled before use.

The hydrindane products of Ti-mediated annulation (alkene isomers) were used in subsequent steps as mixtures (the steroidal end products of the synthesis sequence were easily separated from byproducts generated from the minor "endo" diene isomer). For characterization of the major isomers formed from Ti-mediated annulation, a small amount of each mixture (<50 mg) was purified by HPLC to obtain analytical samples. (See, the trans-fused hydrindanes: 8, ent-8, 14, 17, 20, 23, 26, 29, 32, and S16).

Abbreviations: KOt-Bu: potassium tert-butoxide; TEBAC: benzyltriethylammonium chloride; MeNO$_2$: nitromethane, i-PrOH: isopropanol; MeOH: methanol.

Where yields are given, the data refers to chromatographically and spectroscopically ($^1$H NMR) homogeneous materials, unless otherwise stated.

1A. Epoxide S2 and Chlorohydrin S1

This Example describes the production of intermediates epoxide S2 and chlorohydrin S1 used in subsequent reactions.

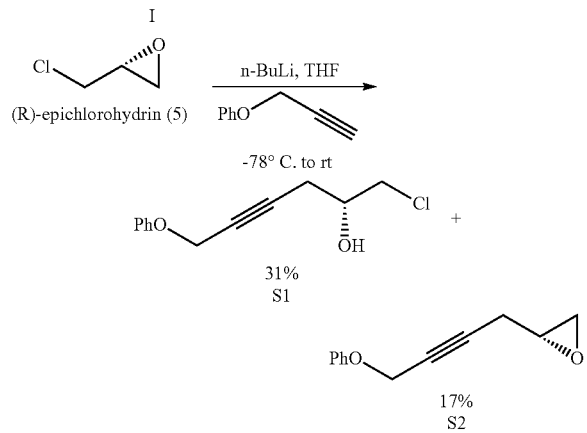

To a stirring solution of phenyl propargyl ether (0.50 g, 3.8 mmol, 1.0 equiv) in 5 mL THF at −78° C. under N$_2$ atmosphere was added n-BuLi (2.5 M in hexanes, 1.5 mL, 3.8 mmol, 1.0 equiv) dropwise. The resulting solution was stirred for 1 h at −78° C., and (R)-epichlorohydrin 5 (0.35 g, 3.8 mmol, 1.0 equiv) was added dropwise. The resulting mixture was slowly warmed to rt and stirred overnight (approx. 12 h), then 20 mL sat. NH$_4$Cl (aq) was added. The organic layer was separated, and the aqueous layer was extracted with ethyl acetate (30 mL×3). The combined organic layers were dried over anhydrous MgSO$_4$, filtered through a coarse fritted glass funnel, and the filtrate was concentrated in vacuo. Purification of the crude product by flash column chromatography afforded 0.12 g of epoxide S2 as a yellow film (17%) and 0.26 g chlorohydrin S1 as a yellow oil (31%).

1B. Enyne 6

This Example describes the production of intermediate enyne 6 used in subsequent reactions.

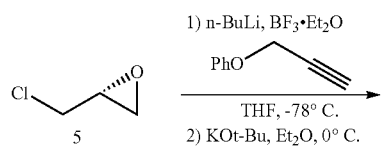

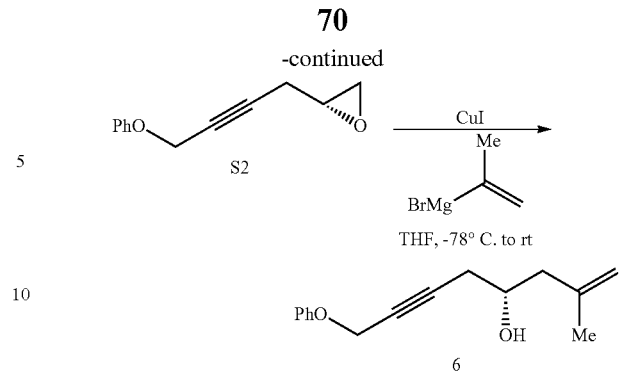

To a stirring solution of phenyl propargyl ether (18.2 g, 138 mmol, 1.5 equiv) in 500 mL THF at −78° C. under N$_2$ atmosphere was added n-BuLi (2.5 M in hexanes, 50.0 mL, 130 mmol, 1.4 equiv) dropwise. The resulting solution was stirred for 15 min at −78° C., and then BF$_3$·Et$_2$O (21.3 g, 150 mmol, 1.7 equiv) and (R)-epichlorohydrin 5 (8.3 g, 89 mmol, 1.0 equiv) were added dropwise. The resulting mixture was stirred for an additional 1 h at −78° C., warmed to 0° C., and then 100 mL sat. NH$_4$Cl (aq) was added. The organic layer was separated, and the aqueous layer was extracted with Et$_2$O (200 mL×3). The combined organic layers were dried over anhydrous MgSO$_4$, filtered through a coarse fritted glass funnel, and the filtrate was concentrated in vacuo. The crude oil was dissolved in hexanes, and then passed through a pad of silica gel using 85% hexanes: 15% ethyl acetate as the eluent to afford 10.4 g of the crude product (yellow oil), that was used in the next step without further purification.

To a stirring solution of the above crude product (10.4 g) in 1.1 L Et$_2$O under N$_2$ atmosphere at rt was added KOt-Bu (4.6 g, 41 mmol). The resulting yellow suspension was stirred until the reaction was judged to be complete by TLC analysis. 500 mL sat. NaHCO$_3$ (aq) was added to the reaction mixture, and the organic layer was separated. The aqueous layer was extracted with Et$_2$O (200 mL×3). The combined organic layers were dried over anhydrous Na$_2$SO$_4$, filtered through a coarse fritted glass funnel, and the filtrate was concentrated in vacuo to afford 8.3 g of the crude epoxide S2 (yellow oil), that was used in the next step without further purification.

To a stirring solution of 60% weight of the above epoxide S2 (5.0 g) in 75 mL THF under N$_2$ atmosphere at −78° C. was added CuI (1.0 g, 5.3 mmol) followed by isopropenyl magnesium bromide (0.50 M in THF, 74 mL, 37 mmol). The resulting yellow suspension was stirred for 1 h at −78° C., warmed to rt, and then stirred until the reaction was judged to be complete by TLC analysis. The reaction was quenched by adding 100 mL sat. NH$_4$Cl (aq) to the reaction mixture. The organic layer was separated, and the aqueous layer was extracted with ethyl acetate (100 mL×3). The combined organic layers were dried over anhydrous Na$_2$SO$_4$, filtered through a fritted glass funnel, and the filtrate was concentrated in vacuo. Purification of the crude product by SiO$_2$ flash column chromatography using 20% ethyl acetate: 80% hexanes as the eluent afforded 4.8 g of the compound enyne 6 as a pale yellow oil (39% over 3 steps).

1C. Epoxide 42

This Example describes the production of intermediate epoxide 42 used in subsequent reactions.

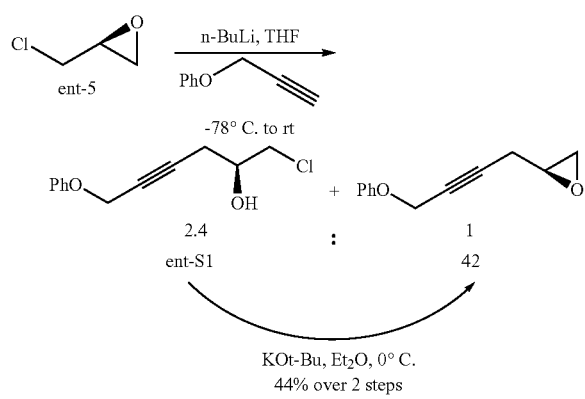

Briefly, n-BuLi (2.5 M in hexanes, 0.15 L, 0.38 mol, 1.0 equiv) was added dropwise to a stirring solution of phenyl propargyl ether (50.0 g, 0.38 mol, 1.0 equiv) in 500 mL THF at −78° C. under N₂ atmosphere. The resulting solution was stirred for 0.5 h at −78° C., and (S)-epichlorohydrin ent-5 (42.0 g, 0.46 mol, 1.2 equiv) was added dropwise. The resulting mixture was slowly warmed to rt and stirred overnight (approx. 12 h), then 300 mL sat. NH₄Cl (aq) was added. The organic layer was separated, and the aqueous layer was extracted with ethyl acetate (300 mL×3). The combined organic layers were dried over anhydrous MgSO₄, filtered through a coarse fritted glass funnel, and the filtrate was concentrated in vacuo to afford 35 g of the crude product. The crude product containing ent-S1 and epoxide 42 (ent-S1:42=2.4:1 based on the crude product analysis by ¹H NMR) was used in the next step without further purification.

To a stirring solution of 80% weight of the above crude product (28 g) in 2.5 L Et₂O under N₂ atmosphere at rt was added KOt-Bu (9.3 g, 0.083 mol). The resulting yellow suspension was stirred until the reaction was judged to be complete by TLC analysis. 500 ml sat. NaHCO₃ (aq) was added to the reaction mixture, and the organic layer was separated. The combined organic layers were dried over anhydrous MgSO₄, filtered through a coarse fritted glass funnel, and the filtrate was concentrated in vacuo. Purification of the crude product by SiO₂ flash column chromatography using 20% ethyl acetate: 80% hexanes as the eluent afforded 24.9 g of the compound epoxide 42 as a pale yellow oil (44% over 2 steps).

1D. S3

This Example describes the production of intermediate S3 used in subsequent reactions.

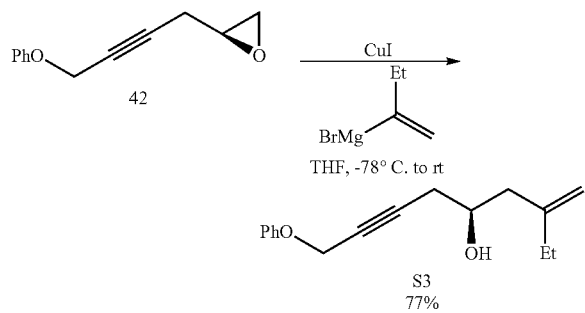

To a stirring suspension of Mg turnings (0.40 g, 17 mmol, 1.3 equiv) in 20 mL THF under N₂ atmosphere at rt was added 1,2-dibromoethane (0.29 g, 1.53 mmol, 0.12 equiv) dropwise. The resulting mixture was heated with a heat gun for approximately 1 min. Once the reaction was initiated, 2-bromobut-1-ene (2.1 g, 15.3 mmol, 1.2 equiv) was added dropwise while maintaining gentle reflux. After the addition, the resulting yellow suspension was further refluxed for an additional 1 h and cooled to rt. The resulting Grignard solution was transferred by syringe to a stirring suspension of epoxide 42 (2.4 g, 13 mmol, 1.0 equiv) and CuI (0.48 g, 2.5 mmol, 0.19 equiv) in 50 mL THF under N₂ atmosphere at −78° C. The resulting yellow suspension was stirred for 1 h at −78° C., warmed to rt, and then stirred until the reaction was judged to be complete by TLC analysis. The reaction was quenched by adding 100 mL of sat. NH₄Cl (aq) to the reaction mixture. The organic layer was separated, and the aqueous layer was extracted with ethyl acetate (100 mL×3). The combined organic layers were dried over anhydrous MgSO₄, filtered through a coarse fritted glass funnel, and the filtrate was concentrated in vacuo. Purification of the crude product by SiO₂ flash column chromatography using 20% ethyl acetate: 80% hexanes as the eluent afforded 2.4 g of the title compound S3 as a yellow oil (77%).

1E. S4

This Example describes the production of intermediate S4 used in subsequent reactions.

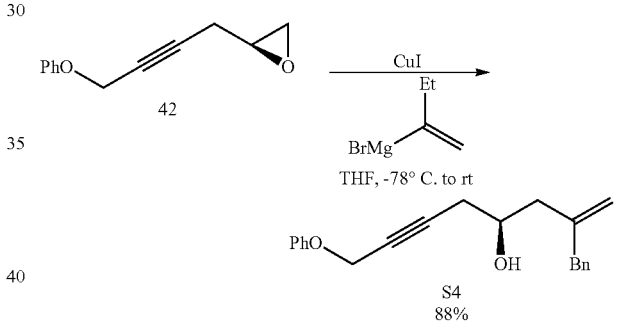

To a stirring suspension of Mg turnings (0.27 g, 11.2 mmol, 1.3 equiv) in 15 mL THF under N₂ atmosphere at rt was added 1,2-dibromoethane (0.20 g, 1.1 mmol) dropwise. The resulting mixture was heated with a heat gun for approximately 1 min. Once the reaction was initiated, (2-bromoallyl)benzene (2.0 g, 10.2 mmol) was added dropwise while maintaining gentle reflux. After the addition, the resulting yellow suspension was further refluxed for an additional 1 h and cooled to rt. The resulting Grignard solution was transferred using syringe to a stirring suspension of epoxide 42 (1.6 g, 8.5 mmol) and CuI (0.32 g, 1.7 mmol, 0.20 equiv) in 20 mL THF under N₂ atmosphere at −78° C. The resulting yellow suspension was stirred for 1 h at −78° C., warmed to rt, and then stirred until the reaction was judged to be complete by TLC analysis. The reaction was quenched by adding 80 mL of sat. NH₄Cl (aq) to the reaction mixture. The organic layer was separated, and the aqueous layer was extracted with ethyl acetate (80 mL×3). The combined organic layers were dried over anhydrous Na₂SO₄, filtered through a coarse fritted glass funnel, and the filtrate was concentrated in vacuo. Purification of the crude product by SiO₂ flash column chromatography using 20% ethyl acetate: 80% hexanes as the eluent afforded 2.3 g of compound S4 as a yellow oil (88%).

1F. Enyne (ent-6)

This Example describes the production of intermediate enyne (ent-6) used in subsequent reactions.

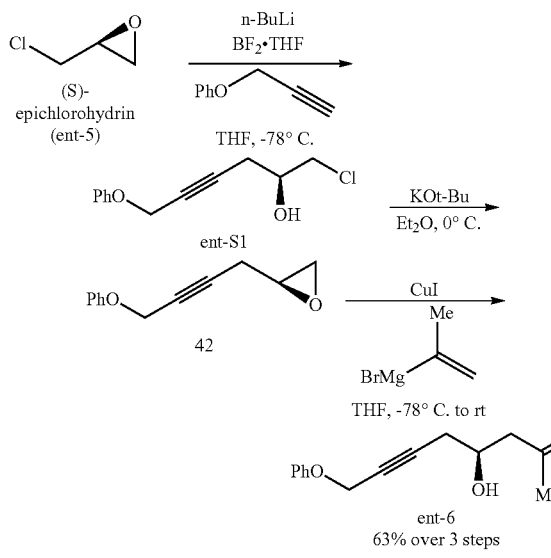

To a stirring solution of phenyl propargyl ether (16 g, 0.12 mol, 2.0 equiv) in 200 mL THF at −78° C. under $N_2$ atmosphere was added n-BuLi (2.5 M in hexanes, 41 mL, 0.10 mol, 1.7 equiv) dropwise. The resulting solution was stirred for 15 min at −78° C., and then $BF_3$·THF (15 g, 0.12 mol, 2.0 equiv) and (S)-epichlorohydrin ent-5 (5.7 g, 61 mmol, 1.0 equiv) were sequentially added dropwise. The resulting mixture was stirred for an additional 1 h at −78° C., warmed to 0° C., and then 100 mL brine was added. The organic layer was separated, and the aqueous layer was extracted with $Et_2O$ (200 mL×3). The combined organic layers were dried over anhydrous $Na_2SO_4$, filtered through a coarse fritted glass funnel, and the filtrate was concentrated in vacuo. The crude oil was dissolved in hexanes, and then eluted through a pad of silica gel using 15% ethyl acetate: 85% hexanes as the eluent to afford 12 g of the crude ent-S1 (yellow oil), that was used in the next step without further purification.

To a stirring solution of the above crude product (12 g) in 1.1 L $Et_2O$ under $N_2$ atmosphere at rt was added KOt-Bu (5.8 g, 51.6 mmol). The resulting yellow suspension was stirred until the reaction was judged to be complete by TLC analysis. 500 mL sat. $NaHCO_3$ (aq) was added to the reaction mixture, and the organic layer was separated. The aqueous layer was extracted with $Et_2O$ (500 mL×3). The combined organic layers were dried over anhydrous $Na_2SO_4$, filtered through a coarse fritted glass funnel, and the filtrate was concentrated in vacuo to afford 9.7 g of the crude epoxide 42 (yellow oil), that was used in the next step without further purification.

To a stirring solution of the crude epoxide 42 (9.7 g) in 115 mL THF under $N_2$ atmosphere at −78° C. was added CuI (2.0 g, 10.3 mmol) followed by isopropenyl magnesium bromide (0.50 M in THF, 0.16 L, 77.0 mmol) dropwise. The resulting yellow suspension was stirred for 1 h at −78° C., warmed to rt, and then stirred until the reaction was judged to be complete by TLC analysis. The reaction was quenched by adding 100 mL of sat. $NH_4Cl$ (aq) to the reaction mixture. The organic layer was separated, and the aqueous layer was extracted with ethyl acetate (500 mL×3). The combined organic layers were dried over anhydrous $Na_2SO_4$, filtered through a coarse fritted glass funnel, and the filtrate was concentrated in vacuo. Purification of the crude product by $SiO_2$ flash column chromatography using 20% ethyl acetate: 80% hexanes as the eluent afforded 8.8 g of the compound ent-6 as a pale yellow oil (63% over 3 steps).

Example 2

Ti-Mediated Coupling Process for Steroid Compound Synthesis (First Series)

2A. Hydrindane 8 and Hydrindane 9

This Example describes the production of intermediates hydrindane 8 and hydrindane 9 used in subsequent reactions.

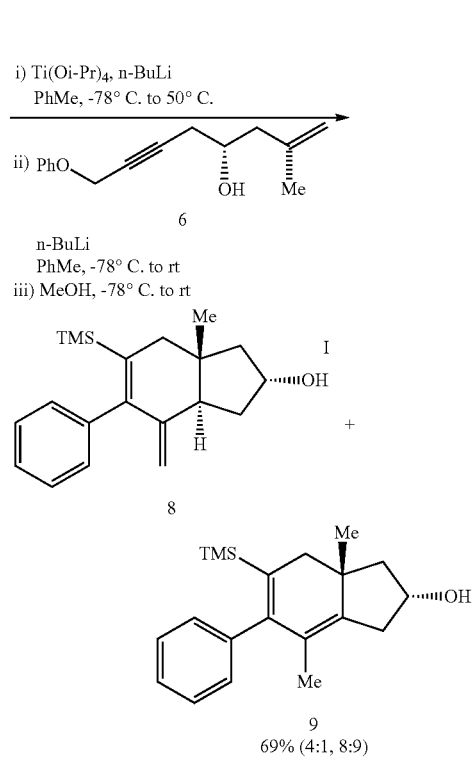

To a stirring solution of alkyne 7 (1.6 g, 9.0 mmol, 2.7 equiv) in 80 mL of dry toluene at rt under $N_2$ atmosphere was added Ti(Oi-Pr)$_4$ (2.6 g, 9.0 mmol 2.7 equiv). The resulting mixture was cooled to −78° C., and n-BuLi (2.4 M in hexanes, 7.6 mL, 18.2 mmol, 5.7 equiv) was added dropwise. The resulting black mixture was warmed first to rt, heated to 50° C., and stirred at 50° C. for 1 h (a reflux condenser was not used). In a separate flask under $N_2$ atmosphere, enyne 6 (0.77 g, 3.4 mmol, 1.0 equiv) was dissolved in 10 mL of dry toluene, cooled to −78° C., and treated with n-BuLi (2.4 M in hexanes, 1.4 mL, 3.4 mmol, 1.0 equiv) dropwise at −78° C. The resulting yellow solution was warmed to rt, and then transferred by cannula to the black Ti-alkyne complex at −78° C. The mixture was slowly warmed to rt overnight (approx. 17 h). After this period, 80 mL of dry MeOH in a separate flask was cooled to −78° C. under $N_2$ atmosphere, and the reaction mixture was transferred by cannula to the pre-cooled MeOH. Once the addition was complete, the reaction mixture was warmed to rt, and 100 mL of sat. NaHCO$_3$ (aq) was added. The reaction mixture was further diluted with 100 mL Et$_2$O. The organic layer was separated, and the aqueous layer was extracted with ethyl acetate (50 mL×3). The combined organic layers were dried over anhydrous MgSO$_4$, filtered through a coarse fritted glass funnel, and then the solvents were removed in vacuo. Purification of the crude product by flash column chromatography afforded 0.65 g of the compounds 8 and 9 as a yellow oil (69%, isolated as a 4:1 mixture of 8:9).

The subsequent procedures were used to convert 73 mg of the trans-fused hydrindane 8 to the steroidal product 12 with an overall 28% isolated yield. This yield is based on the amount of hydrindane 8 present in a 4:1 mixture with the unreactive "endo" diene isomer 9.

2B. Dibromocyclopropane 10

This Example describes the production of intermediates dibromocyclopropane 10 used in subsequent reactions.

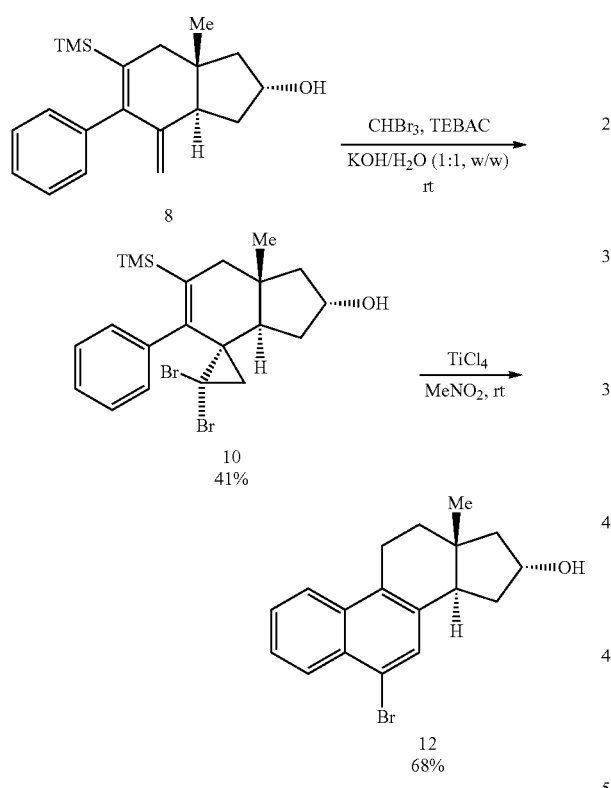

To a solution of TEBAC (12 mg, 0.052 mmol, 0.22 equiv), and 91 mg of 4:1 mixture of hydrindane 8 (73 mg, 0.23 mmol, 1.0 equiv) and its corresponding endo diene isomer (18 mg, 0.058 mmol) in 2.0 mL CHBr$_3$ at rt was added KOH (130 mg, 2.3 mmol, 10 equiv) in water (0.1 mL). The resulting mixture was stirred at 45° C. overnight (approx. 17 h). The reaction mixture was cooled to rt, then partitioned between 10 mL water and 20 mL ethyl acetate. The organic layer was separated, and the aqueous layer was extracted with ethyl acetate (20 mL×3). The combined organic layers were washed with water, brine, and dried over anhydrous MgSO$_4$. The resulting suspension was filtered through a coarse fritted glass funnel, and the filtrate was concentrated in vacuo. Purification of the crude product by flash column chromatography afforded 46 mg of the compound dibromocyclopropane 10 as a pale yellow film (41%).

2C. Steroid 12

This Example describes the production of steroid 12 from the intermediate vinylcyclopropane 10. To a solution of compound 10 (46 mg, 0.095 mmol, 1.0 equiv) in 1 mL nitromethane was added i-PrOH (57 mg, 0.95 mmol, 10 equiv) and TiCl$_4$ (45 mg, 0.24 mmol, 2.5 equiv). The resulting mixture was stirred at rt for 1 h under N$_2$ atmosphere and a second aliquot of i-PrOH (57 mg, 0.95 mmol, 10 equiv) and TiCl$_4$ (45 mg, 0.24 mmol, 2.5 equiv) was added. The mixture was stirred for another 1 h at rt under N$_2$ atmosphere, then partitioned between 10 mL sat. NaHCO$_3$ (aq) and 20 mL CH$_2$Cl$_2$. The organic layer was separated, and the aqueous layer was extracted with CH$_2$Cl$_2$ (20 mL×3). The combined organic layers were washed with brine and dried over anhydrous MgSO$_4$. The resulting suspension was filtered through a coarse fritted glass funnel, and the filtrate was concentrated in vacuo. Purification of the crude product by flash column chromatography afforded 21.3 mg of the title steroid compound 12 as a yellow amorphous solid (68%).

2D. Hydrindane (ent-8)

This Example describes the production of intermediate hydrindane (ent-8) used in subsequent reactions.

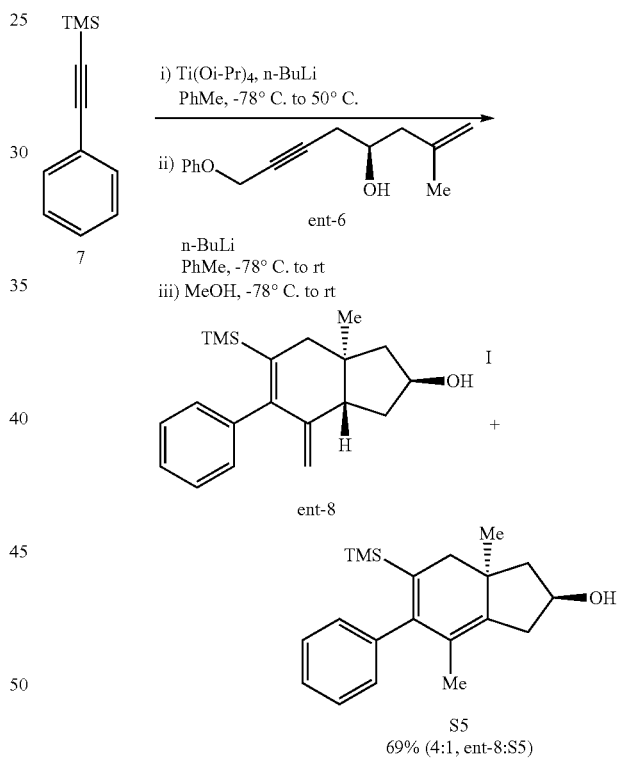

Briefly, to a stirred solution of alkyne 7 (1.1 g, 6.5 mmol, 3.0 equiv) in 40 mL of dry toluene at rt under N$_2$ atmosphere was added Ti(Oi-Pr)$_4$ (1.9 g, 6.5 mmol 3.0 equiv). The resulting mixture was cooled to −78° C., and n-BuLi (2.5 M in hexanes, 5.3 ml, 13 mmol, 6.0 equiv) was added dropwise. The resulting black Ti-alkyne complex was warmed first to rt, heated to 50° C. and stirred at 50° C. for 1 h (a reflux condenser was not used). In a separate flask under N$_2$ atmosphere, enyne ent-6 (0.50 g, 2.2 mmol, 1.0 equiv) was dissolved in 13 mL of dry toluene, cooled to −78° C., and then n-BuLi (2.5 M in hexanes, 0.80 mL, 2.0 mmol, 1.0 equiv) was added dropwise. The resulting yellow solution was warmed to rt, and then transferred by cannula to the black Ti-alkyne complex at −78° C. The mixture was slowly warmed to rt overnight (approx. 17 h). After this period, 50 mL of dry MeOH in a separate flask was cooled to −78° C. under N₂ atmosphere, and the reaction mixture was transferred by cannula to the pre-cooled MeOH. Once the addition was complete, the reaction mixture was warmed to rt, and 30 mL of sat. NaHCO₃ (aq) was added. The organic layer was separated using 100 mL Et₂O, and the aqueous layer was extracted with Et₂O (50 mL×2). The combined organic layers were dried over anhydrous Na₂SO₄, filtered through a coarse fritted glass funnel, and then the filtrate was concentrated in vacuo. Purification of the crude product by flash column chromatography afforded 0.47 g of the compounds ent-8 and S5 as a yellow oil (69%, isolated as a 4:1 mixture of ent-8: S5).

2E. Steroid (ent-12)

This Example describes the production of steroid ent-12 used in subsequent reactions.

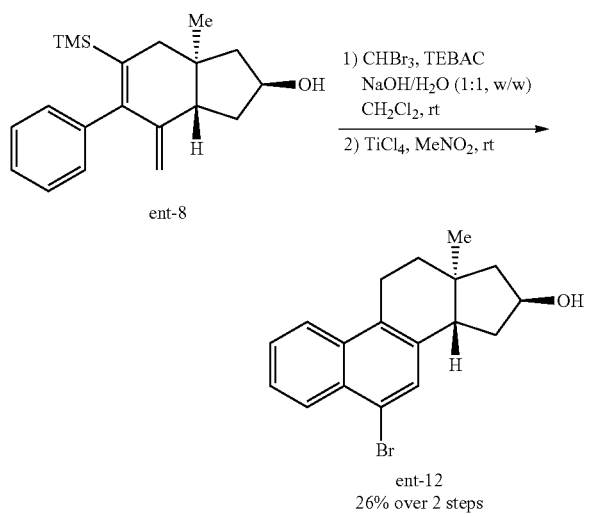

The following two-step procedure was used to convert 88 mg of the trans-fused hydrindane ent-8 to the steroidal product ent-12 with an overall 24% isolated yield. This yield is based on the amount of hydrindane ent-8 present in a 4:1 mixture with the unreactive "endo" diene isomer S5.

To a solution of TEBAC (16 mg, 0.070 mmol, 0.25 equiv), CHBr₃ (0.30 mL, 3.4 mmol, 12 equiv), and 0.11 g of a 4:1 mixture of hydrindane ent-8 (88 mg, 0.28 mmol, 1.0 equiv) and its corresponding endo diene isomer S5 (22 mg, 0.070 mmol) in 2 mL CH₂Cl₂ at rt was added NaOH (0.16 g, 3.9 mmol, 14 equiv) in water (0.16 mL). The resulting mixture was stirred at 45° C. overnight (approx. 17 h). The reaction mixture was cooled to rt, then partitioned between 10 mL DI water and 20 mL ethyl acetate. The organic layer was separated and the aqueous layer was extracted with ethyl acetate (20 mL×3). The combined organic layers were dried over anhydrous MgSO₄, filtered through a coarse fritted glass funnel and the filtrate was concentrated in vacuo to afford 60 mg of the crude product (tentatively assigned dibromo cyclopropane intermediate).

To a solution of the above crude product (60 mg) in 6 mL nitromethane was added TiCl₄ (55 mg, 0.29 mmol) dropwise at rt. The resulting mixture was stirred at rt for 1 h, then partitioned between 30 mL sat. NaHCO₃ (aq) and 30 mL CH₂Cl₂. The organic layer was separated and the aqueous layer was extracted with CH₂Cl₂ (30 mL×3). The combined organic layers were dried over anhydrous MgSO₄, filtered through a coarse fritted glass funnel, and the filtrate was concentrated in vacuo. Purification of the crude product by flash column chromatography afforded 22 mg of compound ent-12 as a yellow amorphous solid (24% over 2 steps).

2F. Hydrindane 14

This Example describes the production of hydrindane 14 used in subsequent reactions.

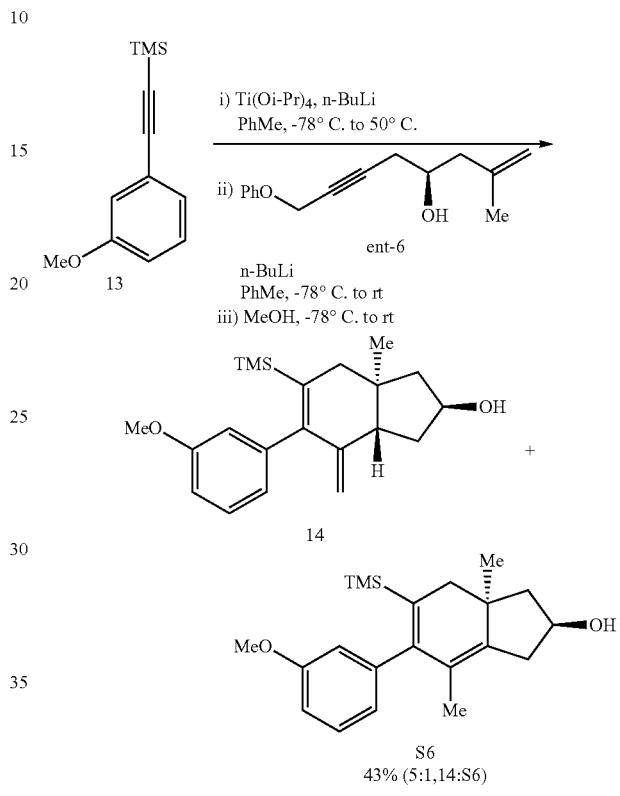

Briefly, to a stirred solution of alkyne 13 (2.7 g, 13 mmol, 3.0 equiv) in 80 mL of dry toluene at rt under N₂ atmosphere was added Ti(Oi-Pr)₄ (3.7 g, 13 mmol 3.0 equiv). The resulting mixture was cooled to −78° C., and n-BuLi (2.3 M in hexanes, 11 ml, 26 mmol, 6.0 equiv) was added dropwise. The resulting black Ti-alkyne complex was warmed first to rt, then heated to 50° C. and stirred at 50° C. for 1 h (a reflux condenser was not used). In a separate flask under N₂ atmosphere, enyne ent-6 (1.0 g, 4.3 mmol, 1.0 equiv) was dissolved in 25 mL of dry toluene, cooled to −78° C., and then n-BuLi (2.3 M in hexanes, 1.9 mL, 4.3 mmol, 1.0 equiv) was added dropwise. The resulting yellow solution was warmed to rt, and then transferred by cannula to the black Ti-alkyne complex at −78° C. The mixture was slowly warmed to rt overnight (approx. 17 h). After this period, 80 mL of dry MeOH in a separate flask was cooled to −78° C. under N₂ atmosphere, and the reaction mixture was transferred by cannula to the pre-cooled MeOH. Once the addition was complete, the reaction mixture was warmed to rt, and 60 mL of sat. NaHCO₃ (aq) was added. The reaction mixture was further diluted with 200 mL Et₂O. The organic layer was separated, and the aqueous layer was extracted with Et₂O (100 mL×2). The combined organic layers were dried over anhydrous Na₂SO₄, filtered through a coarse fritted glass funnel, and then the filtrate was concentrated in vacuo. Purification of the crude product by flash column chromatography afforded 0.64 g of the compounds hydrindane 14 and intermediate S6 as a yellow oil (43%, isolated as a 5:1 mixture of 14:S6).

2G. Steroid 15

This Example describes the production of steroid 15 used in subsequent reactions.

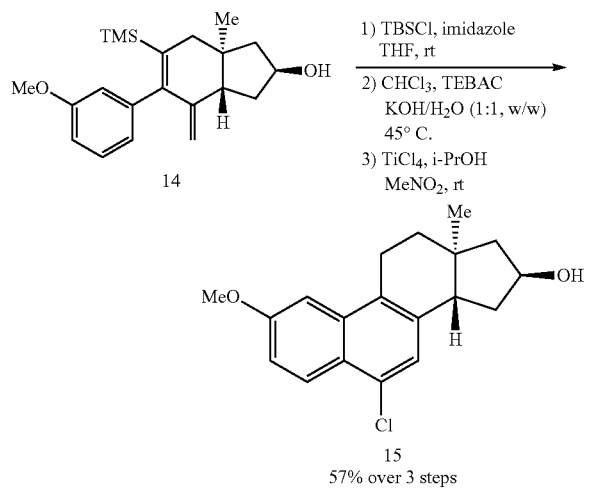

The following three-step procedure was used to convert 0.37 g of the trans-fused hydrindane 14 to the steroidal product 15 with an overall 59% isolated yield. This yield is based on the amount of hydrindane 14 present in a 5:1 mixture with the unreactive "endo" diene isomer S6.

To a solution of 0.44 g of a 5:1 mixture of hydrindane 14 (0.37 g, 1.1 mmol, 1.0 equiv) and its corresponding endo diene isomer S6 (70 mg, 0.2 mmol) in 10 mL THF was added TBSCl (0.94 g, 6.2 mmol, 5.6 equiv) and imidazole (0.52 g, 7.6 mmol, 6.9 equiv). The reaction mixture was stirred at rt under $N_2$ atmosphere overnight (approx. 17 h), then partitioned between 10 mL sat. $NaHCO_3$ (aq) and 10 mL ethyl acetate. The organic layer was separated, and the aqueous layer was extracted with ethyl acetate (10 mL×3). The combined organic layers were washed with brine and dried over anhydrous $MgSO_4$. The resulting suspension was filtered through a coarse fritted glass funnel, and the filtrate was concentrated in vacuo to afford 0.54 g of the crude product (yellow oil), that was used in the next step without further purification.

To a solution of the above crude product (0.54 g) and TEBAC (54 mg, 0.24 mmol) in 2.4 mL $CHCl_3$ at rt was added KOH (0.80 g, 14 mmol) in water (0.8 mL). The reaction mixture was stirred at 45° C. overnight (approx. 17 h). The reaction mixture was cooled to rt, then partitioned between 20 mL water and 50 mL $CH_2Cl_2$. The organic layer was separated, and the aqueous layer was extracted with $CH_2Cl_2$ (100 mL×3). The combined organic layers were washed with brine and dried over anhydrous $MgSO_4$. The resulting suspension was filtered through a coarse fritted glass funnel, and the filtrate was concentrated in vacuo to afford 0.62 g of the crude product (brown film), that was used in the next step without further purification.

To a solution of the above crude product (0.62 g) in 23 mL nitromethane was added i-PrOH (1.2 g, 20 mmol) and $TiCl_4$ (0.31 g, 1.6 mmol). The resulting mixture was stirred at rt for 1 h under $N_2$ atmosphere and a second aliquot of i-PrOH (1.2 g, 20 mmol) and $TiCl_4$ (0.31 g, 1.6 mmol) was added. The mixture was stirred for another 1 h at rt under $N_2$ atmosphere, then partitioned between 50 mL sat. $NaHCO_3$ (aq) and 100 mL $CH_2Cl_2$. The organic layer was separated, and the aqueous layer was extracted with $CH_2Cl_2$ (100 mL×3). The combined organic layers were washed with brine and dried over anhydrous $MgSO_4$. The resulting suspension was filtered through a coarse fritted glass funnel, and the filtrate was concentrated in vacuo. Purification of the crude product by flash column chromatography afforded 0.20 g of the compound steroid 15 as a yellow film (57% over 3 steps).

2H. Hydrindane 17

This Example describes the production of hydrindane 17 used in subsequent reactions.

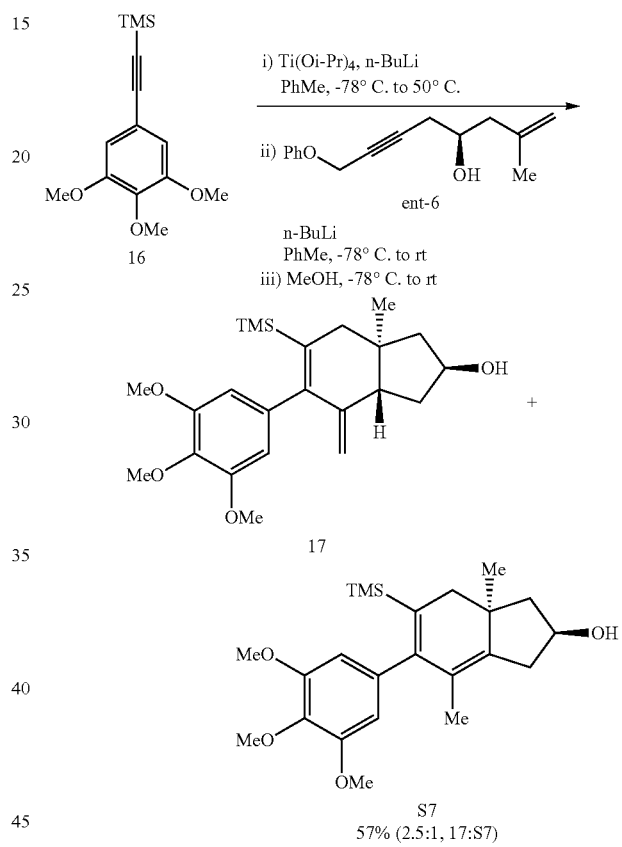

To a stirring solution of alkyne 16 (0.34 g, 1.3 mmol, 3.0 equiv) in 8 mL of dry toluene at rt under $N_2$ atmosphere was added Ti(Oi-Pr)$_4$ (0.37 g, 1.3 mmol 3.0 equiv). The resulting mixture was cooled to −78° C., and n-BuLi (2.3 M in hexanes, 1.1 ml, 2.6 mmol, 6.0 equiv) was added dropwise. The resulting black Ti-alkyne complex was warmed first to rt, then heated to 50° C. and stirred at 50° C. for 1 h (a reflux condenser was not used). In a separate flask, under $N_2$ atmosphere, enyne ent-6 (0.10 g, 0.43 mmol, 1.0 equiv) was dissolved in 2.5 mL of dry toluene, cooled to −78° C., and then n-BuLi (2.3 M in hexanes, 0.20 mL, 0.46 mmol, 1.1 equiv) was added dropwise. The resulting yellow solution was warmed to rt, and then transferred by cannula to the black Ti-alkyne complex at −78° C. The mixture was slowly warmed to rt overnight (approx. 17 h). After this period, 8 mL of dry MeOH in a separate flask was cooled to −78° C. under $N_2$ atmosphere, and the reaction mixture was transferred by cannula to the pre-cooled MeOH. Once the addition was complete, the reaction mixture was warmed to rt, and 60 mL of sat. $NaHCO_3$ (aq) was added. The reaction mixture was further diluted with 20 mL Et$_2$O. The organic layer was separated, and the aqueous layer was extracted with Et$_2$O (50 mL×2). The combined organic layers were dried over anhydrous Na$_2$SO$_4$, filtered through a coarse fritted glass funnel, and then the filtrate was concentrated in vacuo. Purification of the crude product by flash column chromatography afforded 0.10 g of the hydrindane 17 and intermediate S7 as a yellow film (57%, isolated as 2.5:1 mixture of 17:S7).

21. Steroid 18

This Example describes the production of steroid 18 used in subsequent reactions.

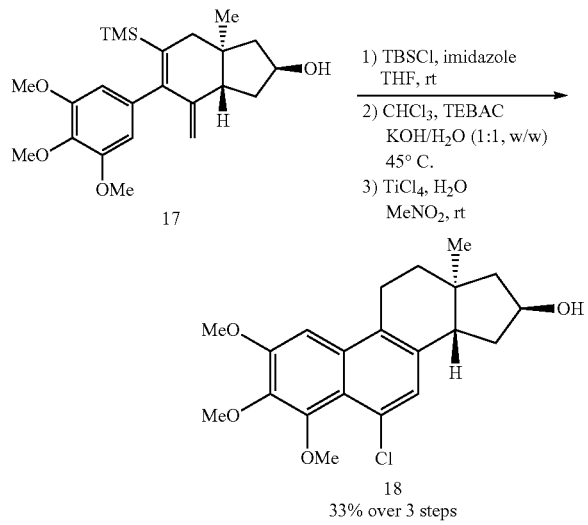

The following three-step procedure was used to convert 0.22 g of the trans-fused hydrindane 17 to the steroidal product 18 with an overall 33% isolated yield. This yield is based on the amount of hydrindane 17 present in a 2.5:1 mixture with the unreactive "endo" diene isomer S7.

To a solution of 0.31 g of 2.5:1 mixture of hydrindane 17 (0.22 g, 0.55 mmol, 1.0 equiv) and its corresponding endo diene isomer S7 (89 mg, 0.22 mmol) in 5 mL THF was added TBSCl (0.58 g, 3.8 mmol, 7.0 equiv) and imidazole (0.31 g, 4.6 mmol, 8.3 equiv). The reaction mixture was stirred at rt under N$_2$ atmosphere overnight (approx. 17 h). The reaction was partitioned between 10 mL sat. NaHCO$_3$ (aq) and 20 mL ethyl acetate. The organic layer was separated, and the aqueous layer was extracted with ethyl acetate (20 mL×3). The combined organic layers were washed with brine and dried over anhydrous MgSO$_4$. The resulting suspension was filtered through a coarse fritted glass funnel, and the filtrate was concentrated in vacuo to afford 0.36 g of the crude product (yellow oil), that was used in the next step without further purification.

To a solution of the above crude product (0.36 g) and TEBAC (35 mg, 0.15 mmol) in 1.2 mL CHCl$_3$ at rt was added KOH (0.50 g, 8.9 mmol) in water (0.50 mL). The reaction mixture was stirred at 45° C. overnight (approx. 17 h). The reaction mixture was cooled to rt, then partitioned between 20 mL DI H$_2$O and 50 mL CH$_2$Cl$_2$. The organic layer was separated, and the aqueous layer was extracted with CH$_2$Cl$_2$ (100 mL×3). The combined organic layers were washed with brine and dried over anhydrous MgSO$_4$. The resulting suspension was filtered through a coarse fritted glass funnel, and the filtrate was concentrated in vacuo to afford 0.38 g of the crude product (brown oil), that was used in the next step without further purification.

To a solution of the above crude product (0.38 g) in 15 mL nitromethane was added DI H$_2$O (0.28 g, 16 mmol) and TiCl$_4$ (2.1 g, 11 mmol). The resulting mixture was stirred at rt until the reaction was judged to be complete by TLC analysis, then partitioned between 50 mL sat. NaHCO$_3$ (aq) and 100 mL CH$_2$Cl$_2$. The organic layer was separated, and the aqueous layer was extracted with CH$_2$Cl$_2$ (100 mL×3). The combined organic layers were washed with brine and dried over anhydrous MgSO$_4$. The resulting suspension was filtered through a coarse fritted glass funnel, and the filtrate was concentrated in vacuo. Purification of the crude product by flash column chromatography afforded 68 mg of compound steroid 18 as a yellow film (isolated as a single isomer, 33% over 3 steps, regioselectivity could not be determined from the crude $^1$H NMR analysis).

2J. Hydrindane 20

This Example describes the production of hydrindane 20 used in subsequent reactions.

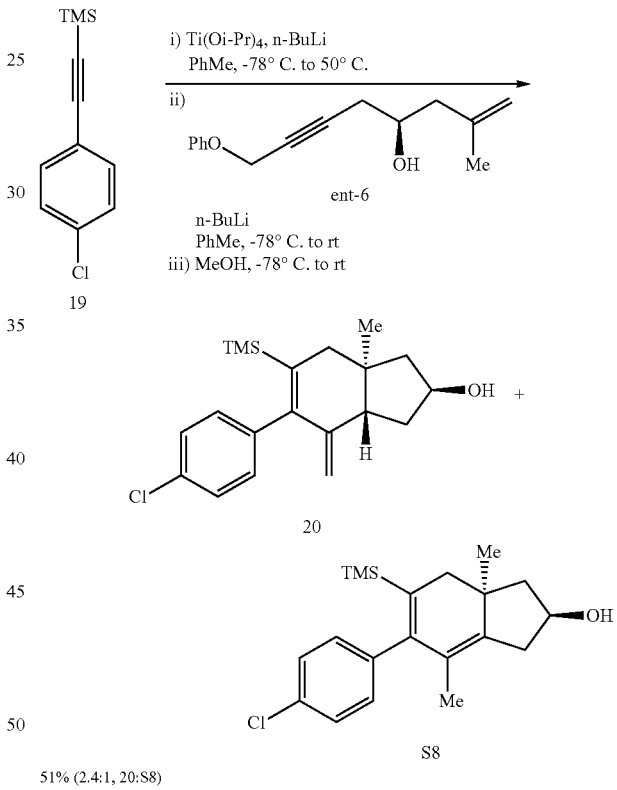

To a stirring solution of alkyne 19 (0.54 g, 2.6 mmol, 3.0 equiv) in 16 mL of dry toluene at rt under N$_2$ atmosphere was added Ti(Oi-Pr)$_4$ (0.74 g, 2.6 mmol 3.0 equiv). The resulting mixture was cooled to −78° C., and n-BuLi (2.4 M in hexanes, 2.2 ml, 5.2 mmol, 6.0 equiv) was added dropwise. The resulting black Ti-alkyne complex was warmed first to rt, then heated to 50° C. and stirred at 50° C. for 1 h (a reflux condenser was not used). In a separate flask, under N$_2$ atmosphere, enyne ent-6 (0.20 g, 0.86 mmol, 1.0 equiv) was dissolved in 5.4 mL of dry toluene, cooled to −78° C., and then n-BuLi (2.4 M in hexanes, 0.37 mL, 0.89 mmol, 1.0 equiv) was added dropwise. The resulting yellow solution was warmed to rt, and then transferred by cannula to the black Ti-alkyne complex at −78° C. The mixture was slowly warmed to rt overnight (approx. 17 h). After this period, 16 mL of dry MeOH in a separate flask was cooled to −78° C. under $N_2$ atmosphere, and the reaction mixture was transferred by cannula to the pre-cooled MeOH. Once the addition was complete, the reaction mixture was warmed to rt, and 12 mL of sat. $NaHCO_3$ (aq) was added. The reaction mixture was further diluted with 40 mL $Et_2O$. The organic layer was separated, and the aqueous layer was extracted with $Et_2O$ (20 ml×2). The combined organic layers were dried over anhydrous $Na_2SO_4$, filtered through a coarse fritted glass funnel, and the filtrate was concentrated in vacuo. Purification of the crude product by flash column chromatography afforded 0.15 g of the compounds hydrindane 20 and intermediate S8 as a yellow film (51%, isolated as a 2.4:1 mixture of 20:S8).

2K. Steroid 21a and Steroid 21b

This Example describes the production of steroid 21a and steroid 21b used in subsequent reactions.

were washed with water, brine, and dried over anhydrous $MgSO_4$. The resulting suspension was filtered through a coarse fritted glass funnel, and the filtrate was concentrated in vacuo. Purification of the crude product by flash column chromatography afforded 50.0 mg of the product (tentatively assigned as a dibromo cyclopropane intermediate).

To a solution of the above product in 6 mL nitromethane was added $TiCl_4$ (55 mg, 0.29 mmol, 1.0 equiv) dropwise at rt. The resulting mixture was stirred at rt for 1 h, then partitioned between 30 mL sat. $NaHCO_3$ (aq) and 30 mL $CH_2Cl_2$. The organic layer was separated and aqueous layer was extracted with $CH_2Cl_2$ (30 mL×3). The combined organic layers were dried over anhydrous $MgSO_4$, filtered through a coarse fritted glass funnel, and the filtrate was concentrated in vacuo to afford 25 mg of the crude product (obtained as a 1.6:1 mixture of the two regioisomers 21a and 21b).

2L. Hydrindane 23

This Example describes the production of hydrindane 23 used in subsequent reactions.

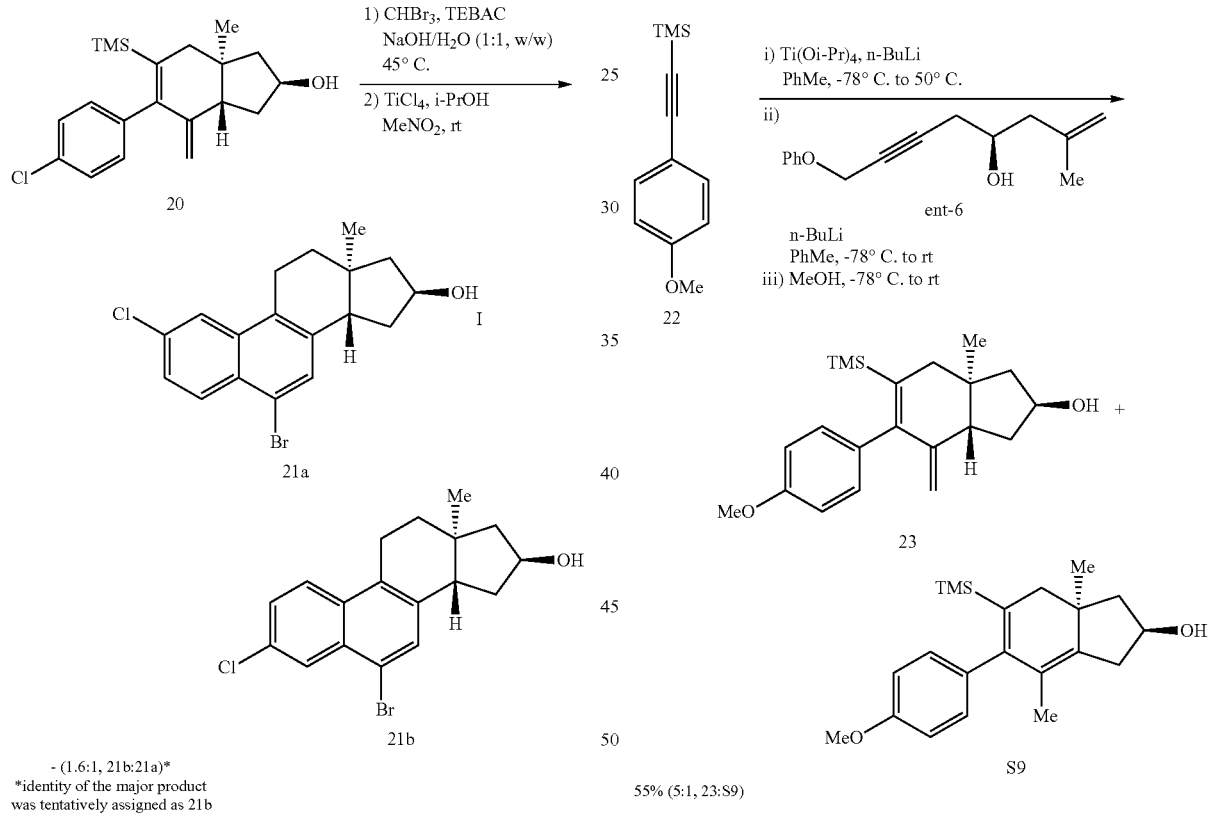

The following two-step procedure was used to convert 0.15 g of the trans-fused hydrindane 20 to the steroidal products 21a and 21b.

To a solution of TEBAC (27 mg, 0.12 mmol, 0.27 equiv), $CHBr_3$ (0.53 mL, 6.1 mmol, 14equiv), and 0.21 g of 2.4:1 mixture of hydrindane 20 (0.15 g, 0.43 mmol, 1.0 equiv) and its corresponding endo diene isomer S8 (60 mg, 0.17 mmol) in 2.0 mL $CH_2Cl_2$ at rt was added NaOH (0.49 g, 12 mmol, 28 equiv) in water (0.49 mL). The resulting mixture was stirred at rt overnight (approx. 17 h), then partitioned between 10 mL water and 20 mL ethyl acetate. The organic layer was separated and the aqueous layer was extracted with ethyl acetate (20 ml×3). The combined organic layers To a stirring solution of alkyne 22 (2.7 g, 13 mmol, 3.0 equiv) in 89 mL of dry toluene at rt under $N_2$ atmosphere was added $Ti(Oi-Pr)_4$ (3.7 g, 13 mmol 3.0 equiv). The resulting mixture was cooled to −78° C., and n-BuLi (2.5 M in hexanes, 10.5 ml, 26 mmol, 6.0 equiv) was added dropwise. The resulting black Ti-alkyne complex was warmed first to rt, then heated to 50° C. and stirred at 50° C. for 1 h (a reflux condenser was not used). In a separate flask, under $N_2$ atmosphere, enyne ent-6 (1.1 g, 4.8 mmol, 1.0 equiv) was dissolved in 30 mL of dry toluene, cooled to −78° C., and then n-BuLi (2.5 M in hexanes, 1.9 mL, 4.8 mmol, 1.0 equiv) was added dropwise. The resulting yellow reaction mixture was warmed to rt, and then transferred by cannula to the black Ti-alkyne complex at −78° C. The mixture was slowly warmed to rt overnight (approx. 17 h). After this period, 80 mL of dry MeOH in a separate flask was cooled to −78° C. under $N_2$ atmosphere, and the reaction mixture was transferred by cannula to the pre-cooled MeOH. Once the addition was complete, the reaction mixture was warmed to rt, and 100 mL of DI $H_2O$ was added. The solvents were removed in vacuo, and the remaining aqueous mixture was extracted with ethyl acetate (100 mL×3). The combined organic layers were dried over anhydrous $Na_2SO_4$, filtered through a coarse fritted glass funnel, and then the filtrate was concentrated in vacuo. Purification of the crude product by flash column chromatography afforded 0.94 g of the compounds hydrindane 23 and S9 as a yellow amorphous solid (55%, isolated as a 5:1 mixture of 23:S9).

2M. Steroid 24

This Example describes the production of steroid 24 used in subsequent reactions.

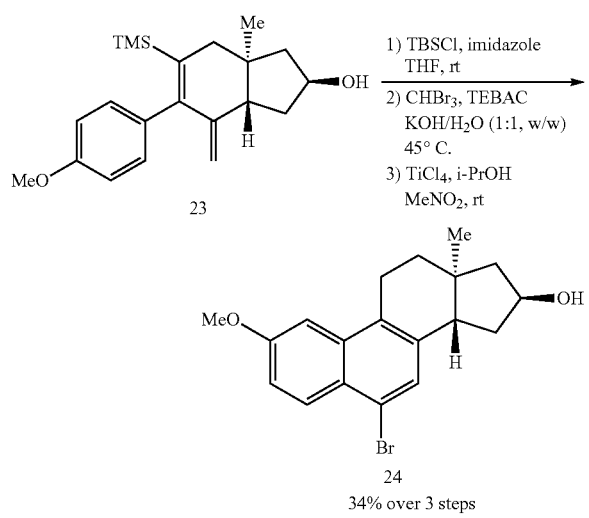

The following three-step procedure was used to convert 92 mg of the trans-fused hydrindane 23 to the steroidal product 24 with an overall 34% isolated yield. This yield is based on the amount of hydrindane 23 present in a 5:1 mixture with the unreactive "endo" diene isomer S9.

To a solution of 0.11 g of 5:1 mixture of hydrindane 23 (92 mg, 0.27 mmol, 1.0 equiv) and its corresponding endo diene isomer S9 (18 mg, 0.052 mmol) in 3 mL THF was added TBSCl (0.24 g, 1.6 mmol, 5.9 equiv) and imidazole (0.13 g, 1.9 mmol, 7.1 equiv). The reaction mixture was stirred at rt under $N_2$ atmosphere overnight (approx. 17 h). The reaction was partitioned between 10 mL sat. $NaHCO_3$ (aq) and 50 mL ethyl acetate. The organic layer was separated, and the aqueous layer was extracted with ethyl acetate (50 mL×3). The combined organic layers were washed with brine and dried over anhydrous $MgSO_4$. The resulting suspension was filtered through a coarse fritted glass funnel, and the filtrate was concentrated in vacuo to afford 0.17 g of the crude product (yellow oil), which was used in the next step without further purification.

To a solution of the above crude product (0.17 g) and TEBAC (35 mg, 0.15 mmol) in 0.6 mL $CHBr_3$ at rt was added KOH (0.25 g, 4.5 mmol) in water (0.25 mL). The reaction mixture was stirred at 45° C. overnight (approx. 17 h). The reaction mixture was cooled to rt, then partitioned between 20 mL water and 50 mL $CH_2Cl_2$. The organic layer was separated, and the aqueous layer was extracted with $CH_2Cl_2$ (100 mL×3). The combined organic layers were washed with brine and dried over anhydrous $MgSO_4$. The resulting suspension was filtered through a coarse fritted glass funnel, and the filtrate was concentrated in vacuo to afford 0.21 g of the crude produc (brown oil), which was used in the next step without further purification.

To a solution of the above crude product (0.21 g) in 6 mL nitromethane was added i-PrOH (0.18 g, 30.0 mmol) and $TiCl_4$ (0.14 g, 0.75 mmol). The resulting mixture was stirred until the reaction was judged to be complete by TLC analysis, then partitioned between 50 mL sat. $NaHCO_3$ (aq) and 50 mL $CH_2Cl_2$. The organic layer was separated, and the aqueous layer was extracted with $CH_2Cl_2$ (50 mL×3). The combined organic layers were washed with brine and dried over anhydrous $MgSO_4$. The resulting suspension was filtered through a coarse fritted glass funnel, and the filtrate was concentrated in vacuo. Purification of the crude product by flash column chromatography afforded 33 mg of the compound steroid 24 as a brown film (34% over 3 steps).

2N. Alkyne 25

This Example describes the production of alkyne 25 used in subsequent reactions.

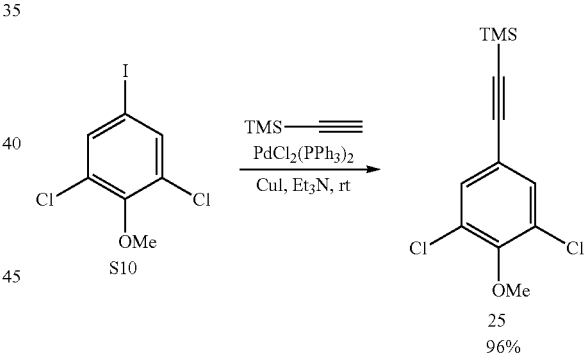

To a stirring solution of aryl iodide S10 (10.0 g, 33 mmol, 1.0 equiv), $PdCl_2(PPh_3)_2$ (0.46 g, 0.66 mmol, 2 mol %), and CuI (0.25 g, 1.3 mmol, 4 mol %) in 82 mL triethylamine under $N_2$ atmosphere at rt was added TMS-acetylene (3.89 g, 40.0 mmol, 1.2 equiv) dropwise. The resulting yellow suspension was stirred overnight under $N_2$ atmosphere at rt (approx. 17 h). The reaction mixture was filtered through a pad of celite, and the filtrate was concentrated in vacuo. The crude oil was dissolved in hexanes, and then passed through a pad of silica using 95% hexanes: 5% ethyl acetate as the eluent. The resulting solution was dried over anhydrous $Na_2SO_4$, filtered through a coarse fritted glass funnel, and the filtrate was concentrated in vacuo to afford 8.7 g of the compound alkyne 25 as a yellow amorphous solid (96%).

20. Hydrindane 26

This Example describes the production of hydrindane 26 used in subsequent reactions.

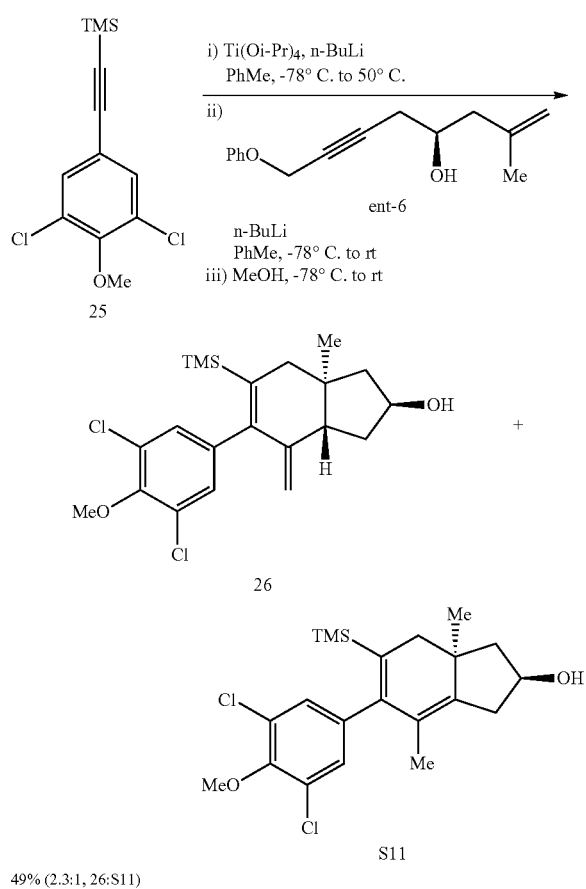

49% (2.3:1, 26:S11)

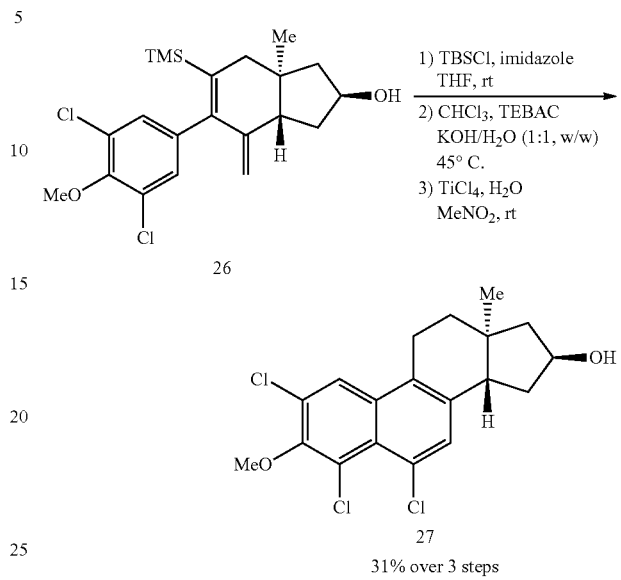

26

27

31% over 3 steps

To a stirring solution of alkyne 25 (3.6 g, 13 mmol, 3.0 equiv) in 80 mL of dry toluene at rt under $N_2$ atmosphere was added Ti(Oi-Pr)$_4$ (3.7 g, 13 mmol 3.0 equiv). The resulting mixture was cooled to −78° C., and n-BuLi (2.3 M in hexanes, 11 ml, 26 mmol, 6.0 equiv) was added dropwise. The resulting black Ti-alkyne complex was warmed first to rt, then heated to 50° C. and stirred at 50° C. for 1 h (a reflux condenser was not used). In a separate flask, under $N_2$ atmosphere, enyne ent-6 (1.0 g, 4.3 mmol, 1.0 equiv) was dissolved in 20 mL of dry toluene, cooled to −78° C., and then n-BuLi (2.3 M in hexanes, 1.9 mL, 4.3 mmol, 1.0 equiv) was added dropwise. The resulting yellow solution was warmed to rt, and then transferred by cannula to the black Ti-alkyne complex at −78° C. The mixture was slowly warmed to rt overnight (approx. 17 h). After this period, 80 mL of dry MeOH in a separate flask was cooled to −78° C. under $N_2$ atmosphere, and the reaction mixture was transferred by cannula to the pre-cooled MeOH. Once the addition was complete, the reaction mixture was warmed to rt, and 70 mL of sat. NaHCO$_3$ (aq) was added. The reaction mixture was further diluted with 100 mL Et$_2$O. The organic layer was separated, and the aqueous layer was extracted with Et$_2$O (100 ml×2). The combined organic layers were dried over anhydrous Na$_2$SO$_4$, filtered through a coarse fritted glass funnel, and the filtrate was concentrated in vacuo. Purification of the crude product by flash column chromatography afforded 0.87 g of compound hydrindane 26 and S11 as a yellow oil (49%, isolated as a 2.3:1 mixture of 26:S11).

2P. Steroid 27

This Example describes the production of steroid 27 used in subsequent reactions.

The following three-step procedure was used to convert 0.16 g of the trans-fused hydrindane 26 to the steroidal product 27 with an overall 31% isolated yield. This yield is based on the amount of hydrindane 26 present in a 2.3:1 mixture with the unreactive "endo" diene isomer S11.

To a solution of 0.23 g of 2.3:1 mixture of hydrindane 26 (0.16 g, 0.39 mmol, 1.0 equiv) and its corresponding endo diene isomer S11 (70.0 mg, 0.17 mmol) in 5 mL THF was added TBSCl (0.42 g, 2.8 mmol, 7.2 equiv) and imidazole (0.23 g, 3.4 mmol, 8.7 equiv). The reaction mixture was stirred at rt under $N_2$ atmosphere overnight (approx. 17 h). The reaction was partitioned between 10 mL sat. NaHCO$_3$ (aq) and 20 mL ethyl acetate. The organic layer was separated, and the aqueous layer was extracted with ethyl acetate (20 mL×3). The combined organic layers were washed with brine and dried over anhydrous MgSO$_4$. The resulting suspension was filtered through a coarse fritted glass funnel, and the filtrate was concentrated in vacuo to afford 0.25 g of the crude product (yellow oil) that was used in the next step without further purification.

To a solution of the above crude product (0.25 g) and TEBAC (25 mg, 0.11 mmol) in 1.0 mL CHCl$_3$ at rt was added KOH (0.38 g, 6.8 mmol) in water (0.38 mL). The reaction mixture was stirred at 45° C. overnight (approx. 17 h). The reaction mixture was cooled to rt, then partitioned between 20 mL DI water and 50 mL CH$_2$Cl$_2$. The organic layer was separated, and the aqueous layer was extracted with CH$_2$Cl$_2$ (100 mL×3). The combined organic layers were washed with brine and dried over anhydrous MgSO$_4$. The resulting suspension was filtered through a coarse fritted glass funnel, and the filtrate was concentrated in vacuo to afford 0.28 g of the crude product (brown film) that was used in the next step without further purification.

To a solution of the above crude product (0.28 g) in 11 mL nitromethane was added DI H$_2$O (0.20 g, 11 mmol) and TiCl$_4$ (2.1 g, 11 mmol). The resulting mixture was stirred at rt until the reaction was judged to be complete by TLC analysis, then partitioned between 50 mL sat. NaHCO$_3$ (aq) and 100 mL CH$_2$Cl$_2$. The organic layer was separated, and the aqueous layer was extracted with CH$_2$Cl$_2$ (100 mL×3).

The combined organic layers were washed with brine and dried over anhydrous MgSO$_4$. The resulting suspension was filtered through a coarse fritted glass funnel, and the filtrate was concentrated in vacuo. Purification of the crude product by flash column chromatography afforded 46 mg of the compound steroid 27 as a yellow film (isolated as a single regioisomer. 31% over 3 steps, regioselectivity could not be determined from the crude $^1$H NMR analysis).

2Q. Alkyne 28

This Example describes the production of alkyne 28 used in subsequent reactions.

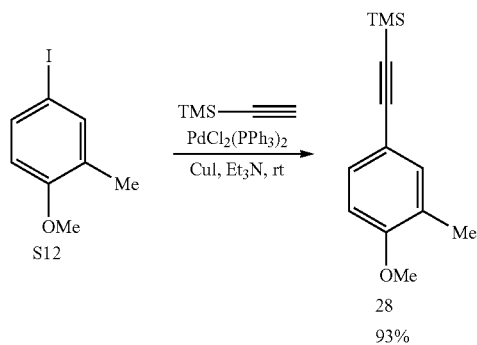

To a stirring solution of aryl iodide S12 (5.0 g, 20 mmol, 1.0 equiv), PdCl$_2$(PPh$_3$)$_2$ (0.28 g, 0.40 mmol, 2 mol %), and CuI (0.15 g, 0.79 mmol, 4 mol %) in 50 mL triethylamine under N$_2$ atmosphere at rt was added TMS-acetylene (2.4 g, 24 mmol, 1.2 equiv) dropwise. The resulting yellow suspension was stirred overnight (approx. 17 h) under N$_2$ atmosphere at rt. The reaction mixture was filtered through a pad of celite, and the filtrate was concentrated in vacuo. The crude oil was dissolved in hexanes, and then passed through a pad of silica using 95% hexanes: 5% ethylacetate as the eluent. The resulting solution was dried over anhydrous Na$_2$SO$_4$, filtered through a coarse fritted glass funnel, and the filtrate was concentrated in vacuo to afford 4.1 g of compound alkyne 28 as a yellow solid (93%).

2R. Hydrindane 29

This Example describes the production of hydrindane 29 used in subsequent reactions.

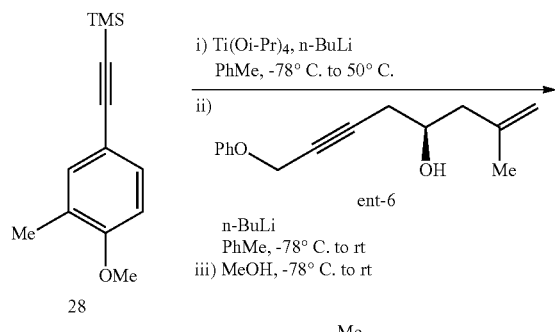

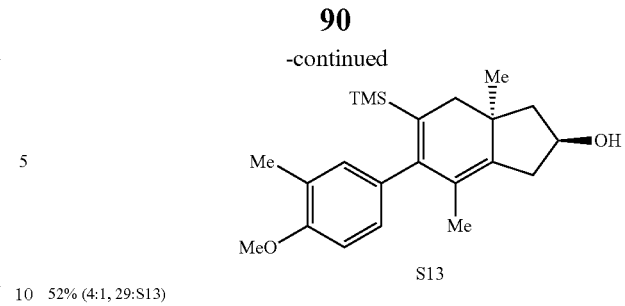

52% (4:1, 29:S13)

To a stirring solution of alkyne 28 (1.1 g, 5.0 mmol, 3.1 equiv) in 30 mL of dry toluene at rt under N$_2$ atmosphere was added Ti(Oi-Pr)$_4$ (1.3 g, 4.7 mmol 2.9 equiv). The resulting mixture was cooled to −78° C., and n-BuLi (2.4 M in hexanes, 4.1 mL, 9.7 mmol, 6.0 equiv) was added dropwise. The resulting black Ti-alkyne complex was warmed first to rt, then heated to 50° C. and stirred at 50° C. for 1 h (a reflux condenser was not used). In a separate flask, under N$_2$ atmosphere, enyne ent-6 (0.37 g, 1.6 mmol, 1.0 equiv) was dissolved in 10 mL of dry toluene, cooled to −78° C., and then n-BuLi (2.4 M in hexanes, 0.68 mL, 1.6 mmol, 1.0 equiv) was added dropwise. The resulting yellow reaction mixture was warmed to rt, and then transferred by cannula to the black Ti-alkyne complex at −78° C. The mixture was slowly warmed to rt overnight (approx. 17 h). After this period, 30 mL of dry MeOH in a separate flask was cooled to −78° C. under N$_2$ atmosphere, and the reaction mixture was transferred by cannula to the pre-cooled MeOH. Once the addition was complete, the reaction mixture was warmed to rt, and 30 mL of sat. NaHCO$_3$ (aq) was added. The reaction mixture was further diluted with 50 mL Et$_2$O. The organic layer was separated, and the aqueous layer was extracted with Et$_2$O (100 mL×2). The combined organic layers were dried over anhydrous Na$_2$SO$_4$, filtered through a coarse fritted glass funnel, and then the filtrate was concentrated in vacuo. Purification of the crude product by flash column chromatography afforded 0.87 g of the compound hydrindane 29 and S13 as a yellow oil (52%, isolated as a 4:1 mixture of 29:S13).

2S. Steroid 30

This Example describes the production of steroid 30 used in subsequent reactions.

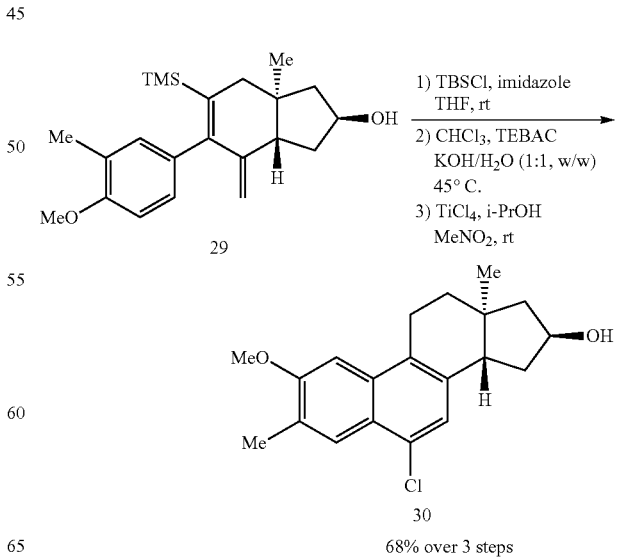

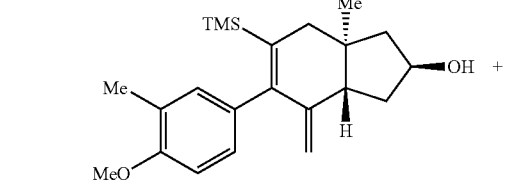

The following three-step procedure was used to convert 0.10 g of the trans-fused hydrindane 29 to the steroidal product 30 with an overall 68% isolated yield. This yield is based on the amount of hydrindane 29 present in a 4:1 mixture with the unreactive "endo" diene isomer S13.

To a solution of 0.13 g of 4:1 mixture of hydrindane 29 (0.10 g, 0.28 mmol, 1.0 equiv) and its corresponding endo diene isomer S13 (26.0 mg, 0.073 mmol) in 5 mL THF was added TBSCl (0.27 g, 1.8 mmol, 6.4 equiv) and imidazole (0.14 g, 2.1 mmol, 7.3 equiv). The reaction mixture was stirred at rt under N₂ atmosphere overnight (approx. 17 h), then partitioned between 50 mL sat. NaHCO₃ (aq) and 50 mL hexanes. The organic layer was separated, and the aqueous layer was extracted with hexanes (20 mL×3). The combined organic layers were dried over anhydrous MgSO₄, filtered through a coarse fritted glass funnel, and the filtrate was concentrated in vacuo to afford 0.16 g of the crude product (yellow oil), that was used in the next step without further purification.

To a solution of the above crude product (0.16 g) and TEBAC (16 mg, 0.070 mmol) in 0.7 mL CHCl₃ at rt was added KOH (0.24 g, 4.3 mmol) in water (0.24 mL). The reaction mixture was stirred at 45° C. overnight (approx. 17 h). The reaction mixture was cooled to rt, then partitioned between 10 mL DI water and 50 mL CH₂Cl₂. The organic layer was separated, and the aqueous layer was extracted with CH₂Cl₂ (50 mL×2). The combined organic layers were dried over anhydrous MgSO₄, filtered through a coarse fritted glass funnel, and the filtrate was concentrated in vacuo to afford 0.18 g of the crude product (brown film), that was used in the next step without further purification.

To a solution of the above crude product (0.18 g) in 7 mL nitromethane was added i-PrOH (0.20 g, 3.3 mmol) and TiCl₄ (0.16 g, 0.84 mmol). The resulting mixture was stirred at rt until the reaction was judged to be complete by TLC analysis, then partitioned between 10 mL sat. NaHCO₃ (aq) and 50 mL CH₂Cl₂. The organic layer was separated, and the aqueous layer was extracted with CH₂Cl₂ (50 mL×2). The combined organic layers were dried over anhydrous MgSO₄, filtered through a coarse fritted glass funnel, and the filtrate was concentrated in vacuo. Purification of the crude product by flash column chromatography afforded 66 mg of the compound steroid 30 as a yellow film (68% over 3 steps).

2T. Hydrindane 32

This Example describes the production of hydrindane 32 used in subsequent reactions.

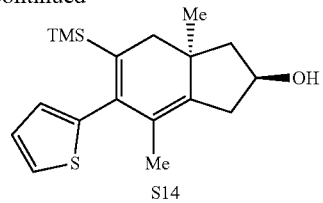

49% (5:1, 32:S14)

To a stirring solution of alkyne 31 (2.4 g, 13 mmol, 3.0 equiv) in 80 mL of dry toluene at rt under N₂ atmosphere was added Ti(Oi-Pr)₄ (3.7 g, 13 mmol 3.0 equiv). The resulting mixture was cooled to −78° C., and n-BuLi (2.4 M in hexanes, 11 mL, 26 mmol, 6.0 equiv) was added dropwise. The resulting black Ti-alkyne complex was warmed first to rt, then heated to 50° C. and stirred at 50° C. for 1 h (a reflux condenser was not used). In a separate flask, under N₂ atmosphere, enyne ent-6 (1.0 g, 4.3 mmol, 1.0 equiv) was dissolved in 20 mL of dry toluene, cooled to −78° C., and then n-BuLi (2.4 M in hexanes, 1.8 mL, 4.3 mmol, 1.0 equiv) was added dropwise. The resulting yellow solution was warmed to rt, and then transferred by cannula to the black Ti-alkyne complex at −78° C. The mixture was slowly warmed to rt overnight (approx. 17 h). After this period, 80 mL of dry MeOH in a separate flask was cooled to −78° C. under N₂ atmosphere, and the reaction mixture was transferred by cannula to the pre-cooled MeOH. Once the addition was complete, the reaction mixture was warmed to rt, and 70 mL of sat. NaHCO₃ (aq) was added. The reaction mixture was further diluted with 100 mL Et₂O. The organic layer was separated, and the aqueous layer was extracted with Et₂O (100 mL×2). The combined organic layers were dried over anhydrous Na₂SO₄, filtered through a coarse fritted glass funnel, and then the filtrate was concentrated in vacuo. Purification of the crude product by flash column chromatography afforded 0.69 g of compounds hydrindane 32 and S14 as a yellow oil (49%, isolated as a 5:1 mixture of 32:S14).

2U. Steroid 33

This Example describes the production of steroid 33 used in subsequent reactions.

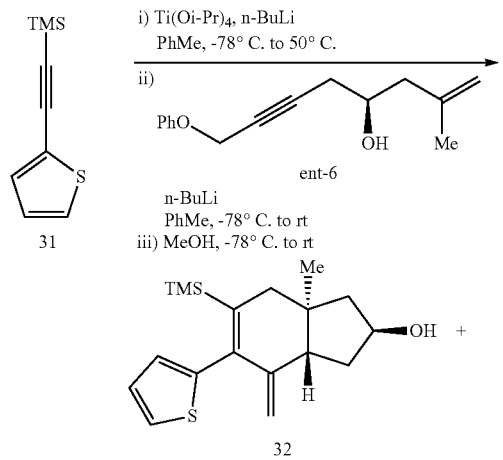

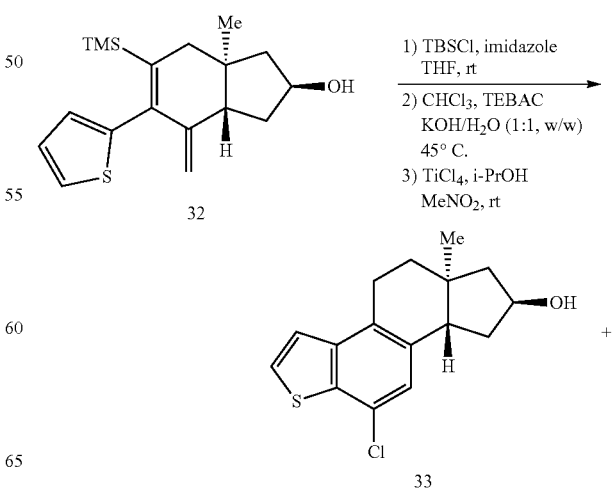

-continued

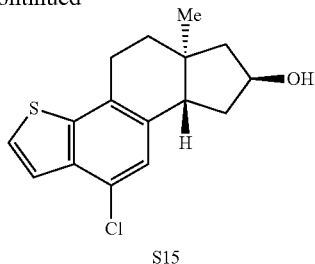

S15

46% (3:1, 33:S15)

The following three-step procedure was used to convert 0.31 g of the trans-fused hydrindane 32 to the steroidal product 33 and intermediate S15 with an overall 47% combined yield. This yield is based on the amount of hydrindane 32 present in a 3:1 mixture with the unreactive "endo" diene isomer S14.

To a solution of 0.37 g of 5:1 mixture of hydrindane 32 (0.31 g, 0.97 mmol, 1.0 equiv) and its corresponding endo diene isomer (60.0 mg, 0.19 mmol) in 10 mL THF was added TBSCl (0.83 g, 5.5 mmol, 5.7 equiv) and imidazole (0.47 g, 6.9 mmol, 7.1 equiv). The reaction mixture was stirred at rt under $N_2$ atmosphere overnight (approx. 17 h), then partitioned between 10 mL sat. $NaHCO_3$ (aq) and 20 mL ethyl acetate. The organic layer was separated, and the aqueous layer was extracted with ethyl acetate (20 mL×3). The combined organic layers were dried over anhydrous $MgSO_4$, filtered through a coarse fritted glass funnel, and the filtrate was concentrated in vacuo to afford 0.43 g of the crude product (yellow oil), that was used in the next step without further purification.

To a solution of the above crude product (0.43 g) and TEBAC (45 mg, 0.20 mmol) in 2.0 mL $CHCl_3$ at rt was added KOH (0.67 g, 12 mmol) in water (0.67 mL). The reaction mixture was stirred at 45° C. overnight (approx. 17 h). The reaction mixture was cooled to rt, then partitioned between 10 mL DI water and 50 mL $CH_2Cl_2$. The organic layer was separated, and the aqueous layer was extracted with $CH_2Cl_2$ (100 mL×3). The combined organic layers were dried over anhydrous $MgSO_4$, filtered through a coarse fritted glass funnel, and the filtrate was concentrated in vacuo to afford 0.54 g of the crude product (brown film), that was used in the next step without further purification.

To a solution of the above crude product (0.54 g) in 20 mL nitromethane was added i-PrOH (0.79 g, 13 mmol) and $TiCl_4$ (0.50 g, 2.6 mmol). The resulting mixture was stirred at rt for 1 h under $N_2$ atmosphere and a second aliquot of i-PrOH (0.79 g, 13 mmol) and $TiCl_4$ (0.50 g, 2.6 mmol) was added. The mixture was stirred for another 1 h at rt under $N_2$ atmosphere, then partitioned between 50 mL sat. $NaHCO_3$ (aq) and 100 mL $CH_2Cl_2$. The organic layer was separated, and the aqueous layer was extracted with $CH_2Cl_2$ (100 mL×3). The combined organic layers were washed with brine and dried over anhydrous $MgSO_4$. The resulting suspension was filtered through a coarse fritted glass funnel, and the filtrate was concentrated in vacuo. Purification of the crude product by flash column chromatography afforded 0.13 g of compounds steroid 33 and intermediate S15 as a yellow amorphous solid (46% as a 3:1 mixture of 33 and S15 over 3 steps). The analytical samples for 33 and S15 were obtained by HPLC purification using a small amount (<50 mg) of the mixture.

2V. Hydrindane S16

This Example describes the production of hydrindane S16 used in subsequent reactions.

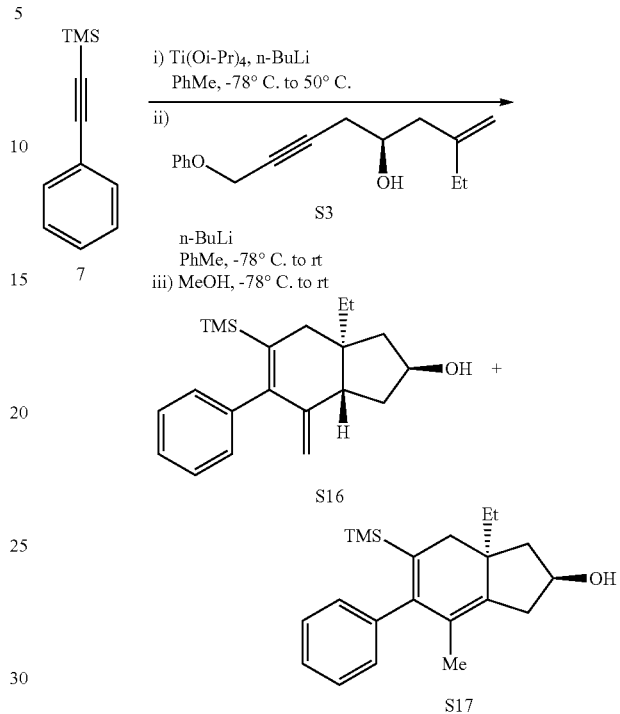

45% (1.4:1, S16:S17)

Briefly, to a stirred solution of alkyne 7 (0.71 g, 4.1 mmol, 2.7 equiv) in 40 mL of dry toluene at rt under $N_2$ atmosphere was added $Ti(Oi-Pr)_4$ (1.2 g, 4.1 mmol 2.7 equiv). The resulting mixture was cooled to −78° C., and n-BuLi (2.4 M in hexanes, 3.6 mL, 8.6 mmol, 5.7 equiv) was added dropwise. The resulting black Ti-alkyne complex was warmed first to rt, then heated to 50° C. and stirred at 50° C. for 1 h (a reflux condenser was not used). In a separate flask, under $N_2$ atmosphere, enyne S3 (368 mg, 1.5 mmol, 1.0 equiv) was dissolved in 5 mL of dry toluene, cooled to −78° C., and then n-BuLi (2.4 M in hexanes, 0.63 mL, 1.5 mmol, 1.0 equiv) was added dropwise. The resulting yellow solution was warmed to rt, and then transferred by cannula to the black Ti-alkyne complex at −78° C. The mixture was slowly warmed to rt overnight (approx. 17 h). After this period, 40 mL of dry MeOH in a separate flask was cooled to −78° C. under $N_2$ atmosphere, and the reaction mixture was transferred by cannula to the pre-cooled MeOH. Once the addition was complete, the reaction mixture was warmed to rt, and 30 mL of sat. $NaHCO_3$ (aq) was added. The reaction mixture was further diluted with 100 mL $Et_2O$. The organic layer was separated, and the aqueous layer was extracted with $Et_2O$ (50 mL×3). The combined organic layers were dried over anhydrous $Na_2SO_4$, filtered through a coarse fritted glass funnel, and then the filtrate was concentrated in vacuo. Purification of the crude product by flash column chromatography afforded 221 mg of compounds hydrindane S16 and S17 as a yellow oil (45%, isolated as a 1.4:1 mixture of S16:S17).

2W. Steroid 34

This Example describes the production of steroid 34 used in subsequent reactions.

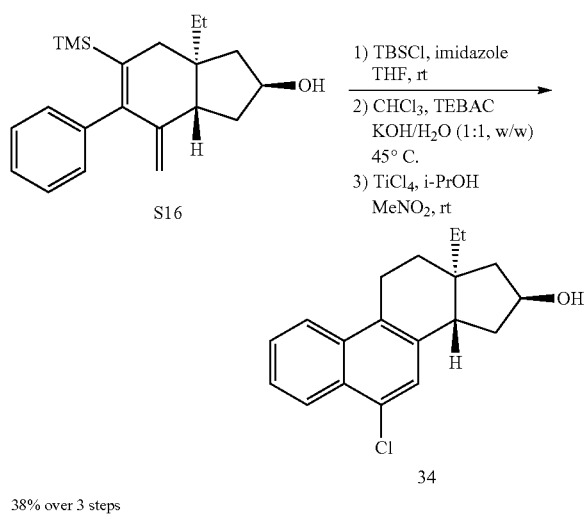

38% over 3 steps

The following three-step procedure was used to convert 112 mg of the trans-fused hydrindane S16 to the steroidal product 34 with an overall 38% isolated yield. This yield is based on the amount of hydrindane S16 present in a 1.4:1 mixture with the unreactive "endo" diene isomer S17.

To a solution of 0.19 g of 1.4:1 mixture of hydrindane S16 (0.11 g, 0.34 mmol, 1.0 equiv) and its corresponding endo diene isomer S17 (80.0 mg, 0.24 mmol) in 10 mL THF was added TBSCl (0.11 g, 0.71 mmol, 2.0 equiv) and imidazole (60.0 mg, 0.88 mmol, 2.6 equiv). The reaction mixture was stirred at rt under N₂ atmosphere overnight (approx. 17 h). The reaction was partitioned between 20 mL sat. NaHCO₃ (aq) and 20 mL ethyl acetate. The organic layer was separated, and the aqueous layer was extracted with ethyl acetate (10 mL×3). The combined organic layers were washed with brine and dried over anhydrous MgSO₄. The resulting suspension was filtered through a coarse fritted glass funnel, and the filtrate was concentrated in vacuo. The crude product was passed through a pad of silica gel using 99% hexanes: 1% ethyl acetate as the eluent, and the filtrate was concentrated in vacuo to afford 0.20 g of the crude product (yellow oil), that was used in the next step without further purification.

To a solution of 86% weight of the above crude product (0.17 g) and TEBAC (18 mg, 0.080 mmol) in 2 mL CHCl₃ at rt was added KOH (0.35 g, 6.3 mmol) in water (0.35 mL). The reaction mixture was stirred at 45° C. overnight (approx. 17 h). The reaction mixture was cooled to rt, then partitioned between 10 mL DI water and 20 mL CH₂Cl₂. The organic layer was separated, and the aqueous layer was extracted with CH₂Cl₂ (20 mL×3). The combined organic layers were washed with brine and dried over anhydrous MgSO₄. The resulting suspension was filtered through a coarse fritted glass funnel, and the filtrate was concentrated in vacuo to afford 0.21 g of the crude product (brown film), that was used in the next step without further purification.

To a solution of the above crude product (0.21 g) in 2 mL nitromethane was added i-PrOH (0.25 g, 4.1 mmol) and TiCl₄ (0.19 g, 1.0 mmol). The resulting mixture was stirred at rt for 1 h under N₂ atmosphere and a second aliquot of i-PrOH (0.25 g, 4.1 mmol) and TiCl₄ (0.19 g, 1.0 mmol) was added. The mixture was stirred for another 1 h at rt under N₂ atmosphere, then partitioned between 20 mL sat. NaHCO₃ (aq) and 50 mL CH₂Cl₂. The organic layer was separated, and the aqueous layer was extracted with CH₂Cl₂ (50 mL×3). The combined organic layers were washed with brine and dried over anhydrous MgSO₄. The resulting suspension was filtered through a coarse fritted glass funnel, and the filtrate was concentrated in vacuo. Purification of the crude product by flash column chromatography afforded 34 mg of the compound steroid 34 as a yellow film (38% over 3 steps).

2X. Hydrindane S18

This Example describes the production of hydrindane S18 used in subsequent reactions.

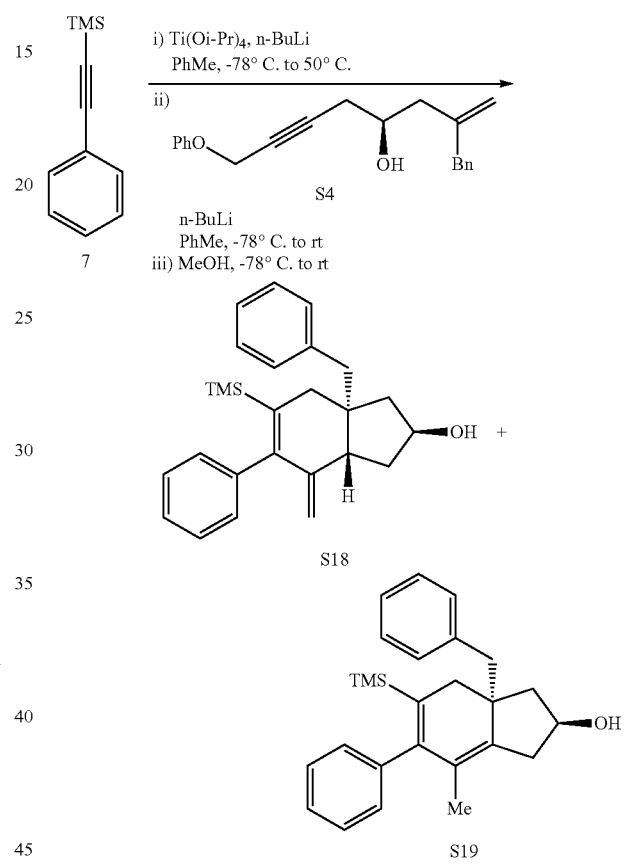

34% (1.1:1, S18:S19)

Briefly, to a stirred solution of alkyne 7 (1.5 g, 8.8 mmol, 2.7 equiv) in 80 mL of dry toluene at rt under N₂ atmosphere was added Ti(Oi-Pr)₄ (2.5 g, 8.8 mmol 2.7 equiv). The resulting mixture was cooled to −78° C., and n-BuLi (2.4 M in hexanes, 7.9 mL, 18.6 mmol, 5.7 equiv) was added dropwise. The resulting black Ti-alkyne complex was warmed first to rt, then heated to 50° C. and stirred at 50° C. for 1 h (a reflux condenser was not used). In a separate flask, under N₂ atmosphere, enyne S4 (1.0 g, 3.3 mmol, 1.0 equiv) was dissolved in 10 mL of dry toluene, cooled to −78° C., and then n-BuLi (2.4 M in hexanes, 1.4 mL, 3.3 mmol, 1.0 equiv) was added dropwise. The resulting yellow solution was warmed to rt, and then transferred by cannula to the black Ti-alkyne complex at −78° C. The mixture was slowly warmed to rt overnight (approx. 17 h). After this period, 80 mL of dry MeOH in a separate flask was cooled to −78° C. under N₂ atmosphere, and the reaction mixture was transferred by cannula to the pre-cooled MeOH. Once the addition was complete, the reaction mixture was warmed to rt, and 50 mL of sat. NaHCO$_3$ (aq) was added. The reaction mixture was further diluted with 100 mL Et$_2$O. The organic layer was separated, and the aqueous layer was extracted with Et$_2$O (50 mL×2). The combined organic layers were dried over anhydrous Na$_2$SO$_4$, filtered through a coarse fritted glass funnel, and then the filtrate was concentrated in vacuo. Purification of the crude product by flash column chromatography afforded 442 mg of compound hydrindane S18 (35%) as a yellow oil and 393 mg of hydrindane S19 (31%) as a yellow oil.

2Y. Steroid 35

This Example describes the production of steroid 35 used in subsequent reactions.

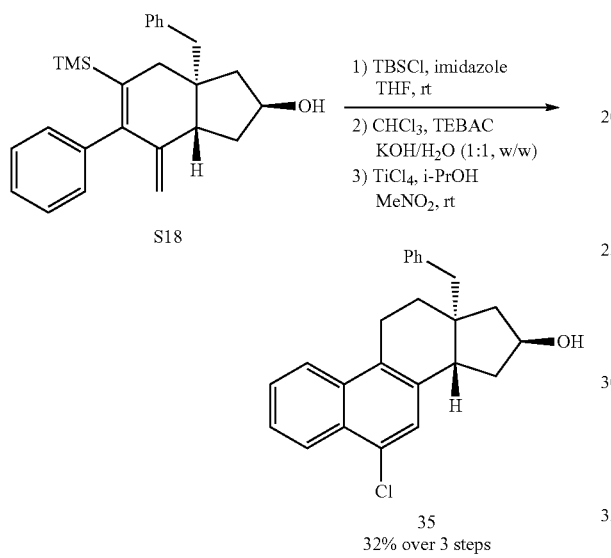

S18

35
32% over 3 steps

To a solution of hydrindane S18 (0.37 g, 0.95 mmol, 1.0 equiv) in 20 mL THF was added TBSCl (0.17 g, 1.1 mmol, 1.2 equiv) and imidazole (97 mg, 1.4 mmol, 1.5 equiv). The reaction mixture was stirred at rt under N$_2$ atmosphere overnight (approx. 17 h), then partitioned between 20 mL sat. NaHCO$_3$ (aq) and 20 mL ethyl acetate. The organic layer was separated, and the aqueous layer was extracted with ethyl acetate (20 mL×3). The combined organic layers were washed with brine and dried over anhydrous MgSO$_4$. The resulting suspension was filtered through a coarse fritted glass funnel, and the filtrate was concentrated in vacuo. The crude product was passed through a pad of silica gel using 99% hexanes:1% ethyl acetate as the eluent, and the filtrate was concentrated in vacuo to afford 465 mg of the crude product (yellow oil), that was used in the next step without further purification.

To a solution of 86% weight of the above crude product (465 mg) and TEBAC (41 mg, 0.18 mmol) in 1.8 mL CHCl$_3$ at rt was added KOH (0.73 g, 13 mmol) in water (0.7 mL). The reaction mixture was stirred at 45° C. overnight (approx. 17 h). The reaction mixture was cooled to rt, then partitioned between 10 mL DI water and 20 mL CH$_2$Cl$_2$. The organic layer was separated, and the aqueous layer was extracted with CH$_2$Cl$_2$ (20 mL×3). The combined organic layers were washed with brine and dried over anhydrous MgSO$_4$. The resulting suspension was filtered through a coarse fritted glass funnel, and the filtrate was concentrated in vacuo to afford 348 mg of the crude product (brown oil), that was used in the next step without further purification.

To a solution of 50% weight of the above crude product (170 mg) in 2 mL nitromethane was added i-PrOH (0.20 g, 3.4 mmol) and TiCl$_4$ (0.16 g, 0.85 mmol). The resulting mixture was stirred at rt for 1 h under N$_2$ atmosphere, and a second aliquot of i-PrOH (0.20 g, 3.4 mmol) and TiCl$_4$ (0.16 g, 0.85 mmol) was added. The mixture was stirred for another 1 h at rt under N$_2$ atmosphere, then partitioned between 20 mL sat. NaHCO$_3$ (aq) and 30 mL CH$_2$Cl$_2$. The organic layer was separated, and the aqueous layer was extracted with CH$_2$Cl$_2$ (20 mL×3). The combined organic layers were washed with brine and dried over anhydrous MgSO$_4$. The resulting suspension was filtered through a coarse fritted glass funnel, and the filtrate was concentrated in vacuo. Purification of the crude product by flash column chromatography afforded 55 mg of compound steroid 35 as a yellow film (32% over 3 steps).

2Z. Steroid 36

This Example describes the production of steroid 36 used in subsequent reactions.

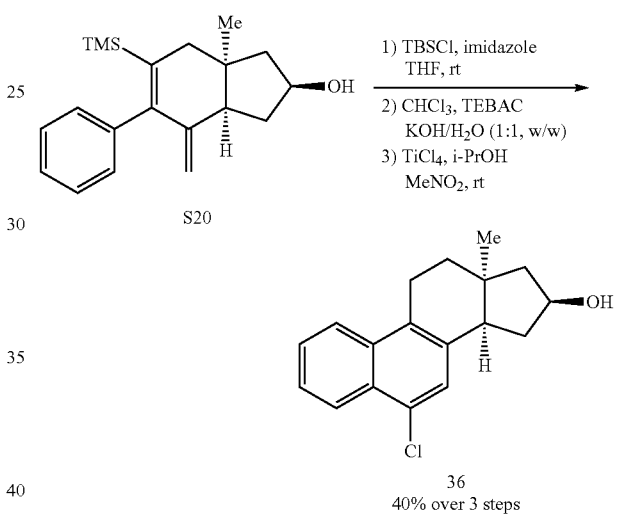

36
40% over 3 steps

To a solution of hydrindane S20 (31 mg, 0.10 mmol, 1.0 equiv) in 3 mL THF was added TBSCl (18 mg, 0.12 mmol, 1.2 equiv) and imidazole (10.0 mg, 0.15 mmol, 1.5 equiv). The reaction mixture was stirred at rt under N$_2$ atmosphere overnight (approx. 17 h), then partitioned between 3 mL sat. NaHCO$_3$ (aq) and 5 mL ethyl acetate. The organic layer was separated, and the aqueous layer was extracted with ethyl acetate (10 mL×3). The combined organic layers were washed with brine, dried over anhydrous MgSO$_4$, and filtered through a course fritted glass funnel. The filtrate was concentrated in vacuo, and the crude product was passed through a pad of silica gel using 98% hexanes:2% ethyl acetate as the eluent. The filtrate was concentrated in vacuo to afford 50 mg of the crude product (yellow oil), that was used in the next step without further purification.

To a solution of the above crude product (50 mg) and TEBAC (4.5 mg, 0.020 mmol) in 1.8 mL CHCl$_3$ at rt was added KOH (89 mg, 1.6 mmol) in water (0.1 mL). The reaction mixture was stirred at 45° C. overnight (approx. 17 h). The reaction mixture was cooled to rt, then partitioned between 5 mL water and 10 mL CH$_2$Cl$_2$. The organic layer was separated, and the aqueous layer was extracted with CH$_2$Cl$_2$ (10 mL×3). The combined organic layers were washed with brine and dried over anhydrous MgSO$_4$. The resulting suspension was filtered through a coarse fritted glass funnel, and the filtrate was concentrated in vacuo to afford 55 mg of the crude product (brown film), that was used in the next step without further purification.

To a solution of the above crude product (55 mg) in 2 mL nitromethane was added i-PrOH (60.0 mg, 1.0 mmol) and TiCl$_4$ (47 mg, 0.25 mmol). The resulting mixture was stirred at rt for 1 h under N$_2$ atmosphere, and a second aliquot of i-PrOH (60.0 mg, 1.0 mmol) and TiCl$_4$ (47 mg, 0.25 mmol) was added. The mixture was stirred for another 1 h at rt under N$_2$ atmosphere, then partitioned between 10 mL sat. NaHCO$_3$ (aq) and 15 mL CH$_2$Cl$_2$. The organic layer was separated, and the aqueous layer was extracted with CH$_2$Cl$_2$ (15 mL×3). The combined organic layers were washed with brine and dried over anhydrous MgSO$_4$. The resulting suspension was filtered through a coarse fritted glass funnel, and the filtrate was concentrated in vacuo. Purification of the crude product by flash column chromatography afforded 11.4 mg of compound steroid 36 as a yellow film (40% over 3 steps).

Example 3

Steroid Compound Synthesis (Second Series)

3A Steroid 201a

This Example describes the production of steroid 201a used in subsequent reactions.

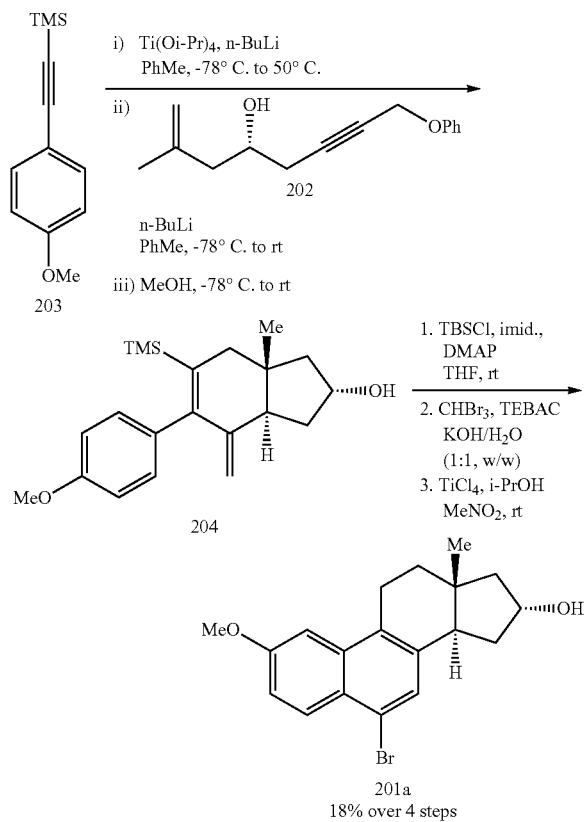

204

201a
18% over 4 steps

Synthesis of steroid 201a: This compound was prepared by following a procedure described herein. To a flask containing alkyne 203 (48 g, 234.47 mmol) in anhydrous toluene (1.6 L) under nitrogen atmosphere was added Ti(Oi-Pr)$_4$ (70 mL, 234.47 mmol). The flask was cooled to −78° C. and n-BuLi (2.6 M in hexanes, 200 mL, 494.99 mmol) was cannulated drop-wise into the flask. After the addition of n-BuLi, the flask was warmed to room temperature. Once it reaches room temperature, it was heated to 50° C. for an hour, and then cooled to room temperature. A separate flask containing a solution of enyne 202 (20 g, 86.84 mmol) in anhydrous toluene (250 mL) was prepared. This flask was cooled to −78° C., and then n-BuLi (2.6 M in hexanes, 35 mL, 86.84 mmol) was added and warmed to room temperature. This enyne mixture was then transferred into the first reaction flask at −78° C. The combined reaction mixture was stirred at room temperature for overnight (approximately 24 h). The next morning, the reaction mixture was transferred drop-wise into a flask containing anhydrous MeOH (1.6 L) at −78° C. under nitrogen. The resulting mixture was concentrated in vacuo to remove MeOH. After concentration, the mixture was carefully quenched with saturated aqueous NaHCO$_3$. The aqueous layer was separated from the organic layer and extracted with ethyl acetate (×3). The combined organic layers were dried over anhydrous MgSO$_4$, and the resulting mixture was vacuum filtered through a coarse fritted glass funnel. The filtrate was concentrated in vacuo to afford hydrindane 204 (14.21 g).

To a solution of hydrindane 204 (14.21 g, 41.48 mmol) in anhydrous THF (600 mL) were added TBSCl (13 g, 91.08 mmol), imidazole (6 g, 91.08 mmol) and DMAP (0.3 g, 2.33 mmol). The reaction mixture was stirred at room temperature under nitrogen atmosphere overnight (approximately 15 h) and quenched with saturated aqueous NaHCO$_3$. The aqueous layer was separated from the organic layer and extracted with ethyl acetate. The combined organic layers were dried over anhydrous MgSO$_4$, and the resulting mixture was vacuum filtered through a coarse fritted glass funnel. The filtrate was concentrated in vacuo to afford the crude product (16 g), which was used in the next step without further purification.

To a solution of the above product (16 g, 35.02 mmol) in CH$_3$Br (75 mL) were added TEBAC (2 g, 8.78 mmol) and a premixed solution of KOH (20 g, 356 mmol) in DI water (20 mL). The reaction mixture was stirred at 45° C. overnight (approximately 16 h) and quenched with DI water. The aqueous layer was separated from the organic layer and extracted with ethyl acetate (×3). The combined organic layers were washed with brine and dried over anhydrous MgSO$_4$. The resulting mixture was vacuum filtered through a coarse fritted glass funnel. The filtrate was concentrated in vacuo to afford the crude product (20 g), which was used in the next step without further purification.

To a solution of the crude product from the previous step (20 g, 31 mmol) in MeNO$_2$ (620 mL) was added TiCl$_4$ (8.5 mL, 77.5 mmol) and i-PrOH (23.5 mL, 310 mmol). After the reaction mixture was stirred at room temperature for an hour, a second portion of TiCl$_4$ (8.5 mL, 77.5 mmol) and i-PrOH (23.5 mL, 310 mmol) was added. The reaction mixture was stirred at room temperature for an hour and quenched with saturated aqueous NaHCO$_3$. The aqueous layer was separated from the organic layer and extracted with DCM (×3). The combined organic layers were dried over anhydrous MgSO$_4$, and the resulting mixture was vacuum filtered through a coarse fritted glass funnel. The filtrate was concentrated in vacuo to afford the crude product, which was purified by flash column chromatography on silica gel with 90:10 to 70:30 hexanes-ethyl acetate gradient elution to afford steroid 201a (5.76 g, 18% over 4 steps) as a yellow solid.

Analytical data for 201a:
TLC (SiO$_2$) R$_f$=0.26 (hexanes:ethylacetate-60:40); [α]$_{589}^T$=+33.915 (c 0.0055, CHCl$_3$); $^1$H NMR (600 NMR, CDCl$_3$) δ 8.12 (d, J=9.1 Hz, 1H), 7.34 (s, 1H), 7.24-7.08 (m, 2H), 4.69 (m, 1H), 3.93 (s, 3H), 3.24-3.11 (m, 2H), 3.07 (m, 1H), 2.30 (dd, J=12.5, 7.3 Hz, 1H), 2.24-2.15 (m, 2H), 2.15-2.07 (m, 1H), 1.89 (td, J=11.8, 7.8 Hz, 1H), 1.74 (br s, 1H), 1.42 (dd, J=12.5, 5.7 Hz, 1H), 0.65 (s, 3H); $^{13}$C NMR (150 MHz, CDCl$_3$) δ 158.14, 137.95, 134.52, 129.43, 129.41, 126.57, 125.75, 120.46, 118.06, 102.27, 72.12, 55.35, 50.55, 47.77, 41.41, 37.22, 35.83, 24.65, 17.75; IR (thin film, cm$^{-1}$) 3360, 2998, 2937, 2854, 2831, 1713, 1623, 1590, 1509, 1448, 1430, 1416, 1376, 1359, 1347, 1315, 1158, 1118, 1088, 1060; HRMS (ESI-TOF) m/z: [M+H] Calculated for C$_{19}$H$_{22}$O$_2$Br 361.0803; Found 361.0786.

3B. Steroid 201b

This Example describes the production of steroid 201b.

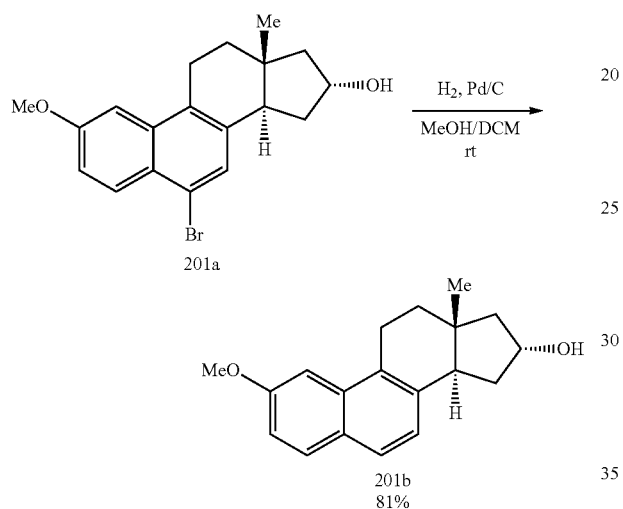

Synthesis of steroid 201b: To a stirring mixture of steroid 201a (30 mg, 0.083 mmol) in 0.6 mL MeOH and 0.15 mL DCM under nitrogen atmosphere was added 10% Pd/C (8.8 mg, 0.0083 mmol) at room temperature. A balloon was used to introduce an atmosphere of hydrogen gas into the flask (allowing first for exchange of the nitrogen atmosphere), and the reaction was stirred under a slightly positive pressure of hydrogen for approximately 8 h. The mixture was filtered through a cotton pipet and rinsed with DCM. The resulting solution was concentrated in vacuo to afford the crude product, which was purified by flash column chromatography on silica gel with 60:40 hexanes-ethyl acetate to afford steroid 201b (19 mg, 81%) as a white solid.

Analytical data for 201b:

TLC (SiO$_2$) R$_f$=0.16 (hexanes:ethyl acetate-75:25); [α]$_{589}^T$=+40.652 (c 0.0089, CHCl$_3$); $^1$H NMR (600 NMR, CDCl$_3$) δ 7.72 (d, J=8.9 Hz, 1H), 7.60 (d, J=8.3 Hz, 1H), 7.19 (d, J=2.5 Hz, 1H), 7.15-7.05 (m, 2H), 4.76-4.65 (m, 1H), 3.94 (s, 3H), 3.28-3.19 (m, 2H), 3.19-3.10 (m, 1H), 2.32 (dd, J=12.4, 7.3 Hz, 1H), 2.27-2.17 (m, 2H), 2.18-2.09 (m, 1H), 1.93 (td, J=11.8, 7.8 Hz, 1H), 1.48-1.39 (m, 1H), 0.67 (s, 3H); $^{13}$C NMR (150 MHz, CDCl$_3$) δ 157.69, 136.85, 133.03, 130.12, 129.27, 127.45, 125.79, 122.70, 116.93, 101.90, 72.32, 55.26, 50.75, 48.01, 41.47, 37.33, 36.04, 24.63, 17.76; IR (thin film, cm$^{-1}$) 3343, 2998, 2937, 2858, 1623, 1596, 1518, 1512, 1456,; HRMS (ESI-TOF) m/z: [M+H] Calculated for C$_{19}$H$_{23}$O$_2$ 283.1698; Found 283.1688.

3C. Steroid 201c

This Example describes the production of steroid 201c.

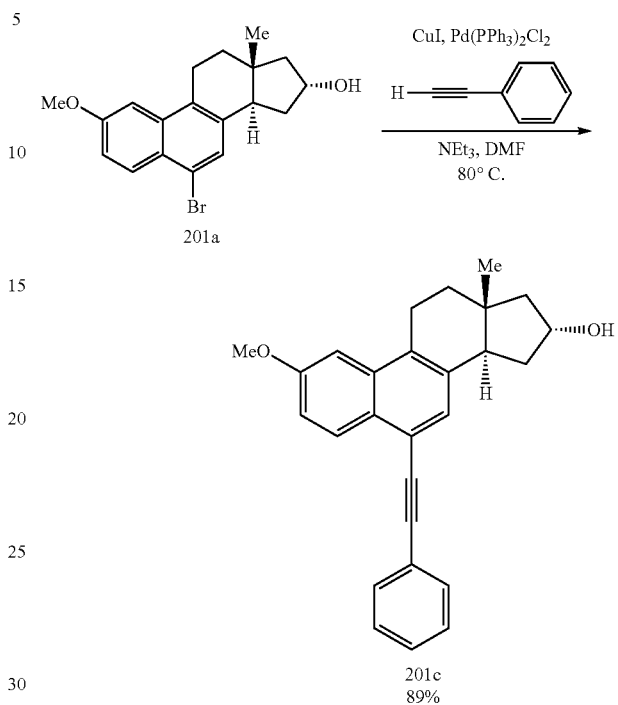

Synthesis of steroid 201c: To a Schlenk tube containing 201a (20 mg, 0.0553 mmol), Pd(PPh$_3$)$_2$Cl$_2$ (1.94 mg, 0.0027 mmol) and CuI (1.05 mg, 0.00553 mmol) under nitrogen atmosphere at room temperature was added anhydrous triethylamine (15 μL, 0.1107 mmol) and anhydrous DMF (2 mL) followed by phenylacetylene (12 μL, 0.1107 mmol). The reaction mixture was stirred at 80° C. overnight (approximately 15 h). The resulting mixture was concentrated in vacuo, and DMF was removed by dissolving the mixture in diethyl ether and extracting with water. The organic layer was then concentrated in vacuo to afford the crude product, which was purified by flash column chromatography on silica gel with 60:40 hexanes-ethyl acetate to afford steroid 201c (19 mg, 89%) as a light yellow solid.

Analytical data for 201c:

TLC (SiO$_2$) R$_f$=0.26 (hexanes:ethyl acetate-60:40); [α]$_{589}^T$=+30.332 (c 0.385, CHCl$_3$); $^1$H NMR (600 NMR, CDCl$_3$) δ 8.35 (d, J=9.1 Hz, 1H), 7.64 (d, J=6.8 Hz, 2H), 7.37 (m, 4H), 7.21 (d, J=8.4 Hz, 2H), 4.72 (p, J=5.8 Hz, 1H), 3.95 (s, 3H), 3.20 (m, 3H), 2.32 (dd, J=12.4, 7.3 Hz, 1H), 2.28-2.20 (m, 2H), 2.15 (dd, J=12.5, 7.6 Hz, 1H), 1.94 (td, J=11.6, 8.3 Hz, 1H), 1.60 (s, 1H), 1.45 (dd, J=12.4, 5.7 Hz, 1H), 0.67 (s, 3H); $^{13}$C NMR (150 MHz, CDCl$_3$) δ 158.02, 136.67, 133.08, 131.61, 130.92, 128.48, 128.40, 128.20, 127.22, 127.16, 123.58, 118.51, 117.61, 102.29, 93.44, 88.15, 72.26, 55.30, 50.64, 47.80, 41.42, 37.31, 35.93, 24.85, 17.77; IR (thin film, cm$^{-1}$) 3423, 2955, 2924, 2857, 1556, 1540, 1519, 1506, 1487, 1336, 1267, 1227, 1059, 1047, 1029; HRMS (ESI-TOF) m/z: [M+H] Calculated for C$_{27}$H$_{27}$O$_2$ 383.2011; Found 383.1995.

3D. Steroid 205a

This Example describes the production of steroid 205a used in subsequent reactions.

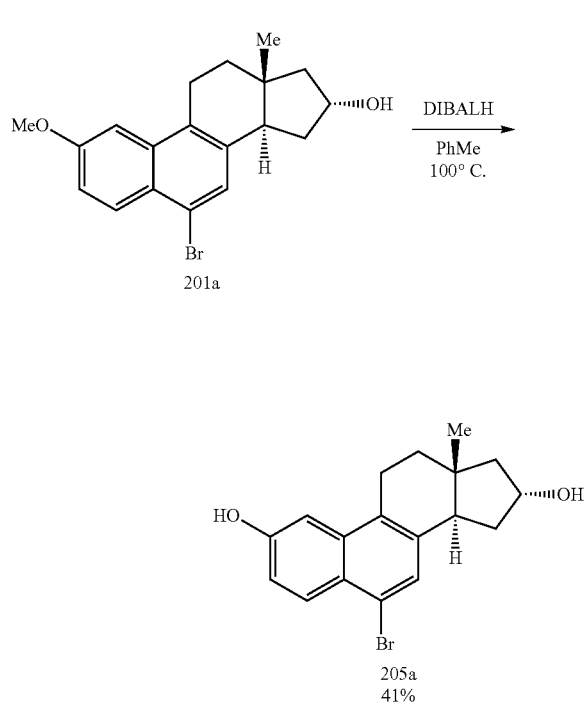

Synthesis of steroid 205a: To a solution of 201a (400 mg, 1.107 mmol) in anhydrous toluene (11 mL) at room temperature was added DIBALH (1.0 M in toluene, 11.07 mL, 11.07 mmol). The reaction mixture was refluxed at 100° C. overnight (approximately 15 h). After the resulting solution was cooled to room temperature, it was quenched by the careful addition of Rochelle's salt and stirred for about 30 mins. The aqueous layer was then separated from the organic layer and extracted with ethyl acetate (×3). The combined organic layers were dried over anhydrous $Na_2SO_4$, and the resulting mixture was vacuum filtered through a coarse fritted glass funnel. The filtrate was concentrated in vacuo to afford the crude product, which was purified by flash column chromatography on silica gel with 70:30 to 50:50 hexanes-ethyl acetate gradient elution to afford 205a (157 mg, 41%) as a white solid.

Analytical data for 205a:

TLC ($SiO_2$) $R_f$=0.21 (hexanes:ethyl acetate-60:40); $[\alpha]_{589}^T$=+31.8231 (c 0.605, $CH_3OH$); $^1H$ NMR (600 NMR, $CD_3OD$) δ 7.93 (d, J=9.1 Hz, 1H), 7.16 (s, 1H), 7.13 (d, J=2.3 Hz, 1H), 7.00 (dd, J=9.1, 2.3 Hz, 1H), 4.50 (m, 1H), 3.06-2.97 (m, 2H), 2.93 (m, 1H), 2.14 (dd, J=12.4, 7.3 Hz, 1H), 2.08-1.96 (m, 3H), 1.76 (td, J=11.7, 8.0 Hz, 1H), 1.30 (dd, J=12.3, 5.9 Hz, 1H), 0.54 (s, 3H); $^{13}C$ NMR (150 MHZ, $CD_3OD$) δ 155.98, 137.59, 134.91, 128.83, 128.76, 125.38, 124.90, 119.92, 117.65, 105.00, 71.05, 49.76, 48.03, 47.89, 47.75, 47.61, 47.46, 47.40, 47.32, 47.18, 40.91, 36.33, 35.61, 24.10, 16.45; IR (thin film, $cm^{-1}$) 3398, 2927, 2859, 1585, 1565, 1552, 1528, 1511, 1481, 1426; HRMS (ESI-TOF) m/z: [M+H] Calculated for $C_{18}H_{20}O_2Br$ 347.0647; Found 347.0657.

3E. Steroid 205b

This Example describes the production of steroid 205b.

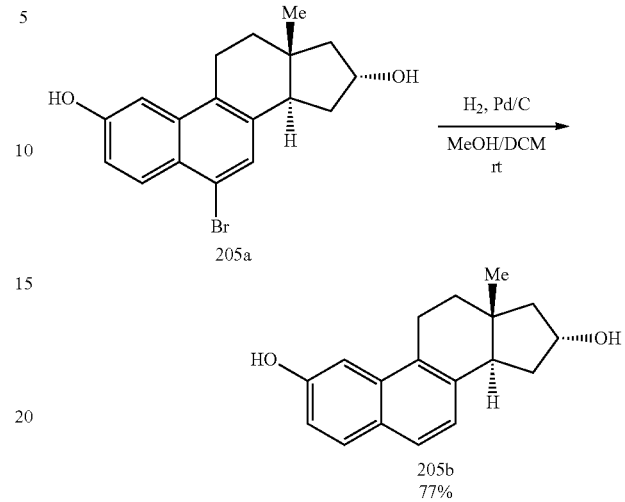

Synthesis of steroid 205b: To a stirring mixture of steroid 205a (30 mg, 0.086 mmol) in 0.6 mL MeOH and 0.15 mL DCM under nitrogen atmosphere was added 10% Pd/C (8.8 mg, 0.0086 mmol) at room temperature. A balloon was used to introduce an atmosphere of hydrogen gas into the flask (allowing first for exchange of the nitrogen atmosphere), and the reaction was stirred under a slightly positive pressure of hydrogen for approximately 8 h. The mixture was filtered through a cotton pipet and rinsed with DCM. The resulting solution was concentrated in vacuo to afford the crude product, which was purified by flash column chromatography on silica gel with 70:30 to 60:40 hexanes-ethyl acetate gradient elution to afford steroid 205b (19 mg, 77%) as a white solid.

Analytical data for 205b:

TLC ($SiO_2$) $R_f$=0.20 (hexanes:ethyl acetate-60:40); $[\alpha]_{589}^T$=+51.374 (c 0.890, $CH_3OH$); $^1H$ NMR (600 NMR, $CD_3OD$) δ 7.55 (d, J=8.8 Hz, 1H), 7.43 (d, J=8.3 Hz, 1H), 7.11 (d, J=2.2 Hz, 1H), 6.90 (dd, J=8.6, 2.8 Hz, 2H), 4.51 (q, J=7.3, 6.7 Hz, 1H), 3.10-3.01 (m, 2H), 2.98 (dt, J=17.9, 9.0 Hz, 1H), 2.14 (dd, J=12.3, 7.3 Hz, 1H), 2.12-2.03 (m, 2H), 2.01 (dd, J=12.7, 7.1 Hz, 1H), 1.79 (td, J=11.7, 8.1 Hz, 1H), 1.31 (dt, J=11.2, 5.6 Hz, 1H), 0.55 (s, 3H); $^{13}C$ NMR (150 MHz, $CD_3OD$) δ 155.03, 136.37, 133.44, 129.72, 128.18, 127.05, 125.53, 121.50, 116.26, 104.47, 71.21, 49.92, 48.04, 47.90, 47.75, 47.69, 47.63, 47.61, 47.47, 47.33, 47.19, 40.95, 36.50, 35.89, 24.06, 16.51; IR (thin film, $cm^{-1}$) 3421, 2948, 2937, 2921, 2983, 2854, 1623, 1516, 1436, 1375, 1364, 1335, 835; HRMS (ESI-TOF) m/z: [M+H] Calculated for $C_{18}H_{21}O_2$ 269.1542; Found 269.1534.

3F Steroid 205c

This Example describes the production of steroid 205c.

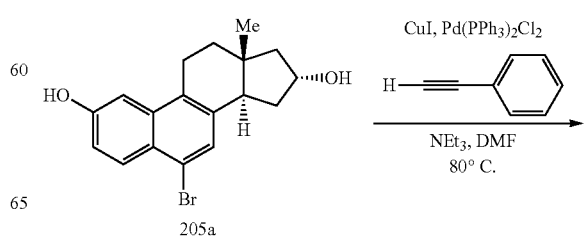

-continued

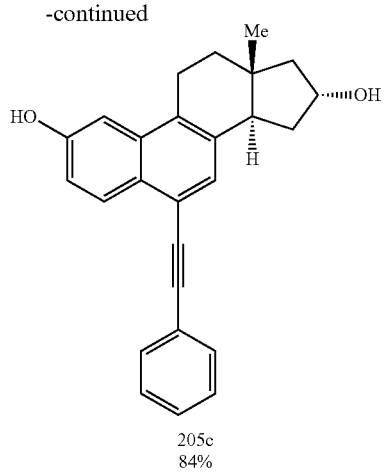

205c
84%

Synthesis of steroid 205c: To a Schlenk tube containing 205a (20 mg, 0.058 mmol), Pd(PPh$_3$)$_2$Cl$_2$ (2.03 mg, 0.0029 mmol) and CuI (1.1 mg, 0.0058 mmol) under nitrogen atmosphere at room temperature was added anhydrous triethylamine (16 μL, 0.1152 mmol) and anhydrous DMF (2 mL) followed by phenylacetylene (12 μL, 0.1152 mmol). The reaction mixture was stirred at 80° C. overnight (approximately 15 h). The resulting mixture was concentrated in vacuo, and DMF was removed by dissolving the mixture in diethyl ether and extracting it with water. The organic layer was then concentrated in vacuo to afford the crude product, which was purified by flash column chromatography on silica gel with 60:40 hexanes-ethyl acetate to afford steroid 5c (18 mg, 84%) as a yellow solid.

Analytical data for 205c:
TLC (SiO$_2$) R$_f$=0.20 (hexanes:ethyl acetate-60:40); [α]$_{589}^T$=+26.178 (c 0.105, CHCl$_3$); $^1$H NMR (600 NMR, CDCl$_3$) δ 8.34 (d, J=8.9 Hz, 1H), 7.73-7.53 (m, 2H), 7.49-7.31 (m, 4H), 7.28 (d, J=2.5 Hz, 1H), 7.14 (dd, J=8.9, 2.5 Hz, 1H), 5.15 (br s, 1H), 4.78-4.67 (m, 1H), 3.20 (dd, J=18.0, 7.9 Hz, 2H), 3.12 (m, 1H), 2.32 (dd, J=12.4, 7.3 Hz, 1H), 2.28-2.17 (m, 2H), 2.13 (dd, J=12.7, 7.5 Hz, 1H), 1.92 (td, J=11.7, 7.7 Hz, 1H), 1.44 (dd, J=12.5, 5.7 Hz, 1H), 0.66 (s, 3H); $^{13}$C NMR (150 MHz, CDCl$_3$) δ 153.86, 136.79, 131.61, 130.68, 128.95, 128.41, 128.23, 127.27, 127.18, 123.54, 118.62, 116.94, 105.97, 93.50, 88.05, 77.10, 76.89, 72.28, 50.61, 47.76, 41.43, 37.24, 35.88, 29.71, 24.72, 17.76; IR (thin film, cm$^{-1}$) 3421, 3237, 2973, 2916, 2852, 1717, 1698, 1682, 1658, 1647, 1635, 1619, 1558, 1223; HRMS (ESI-TOF) m/z: [M+H] Calculated for C$_{26}$H$_{25}$O$_2$ 369.1855; Found 369.1837.

3G. Steroid 206a

This Example describes the production of steroid 206a used in subsequent reactions.

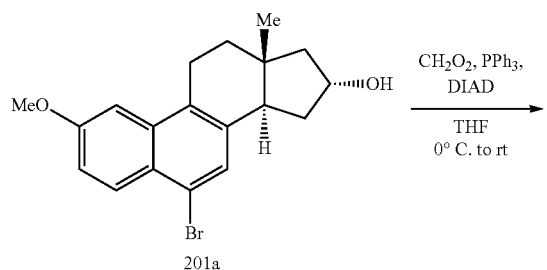

-continued

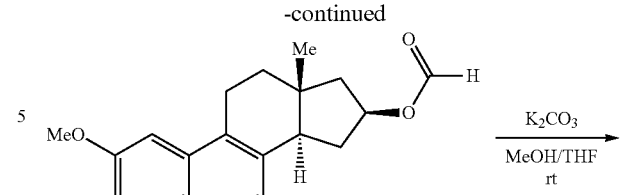

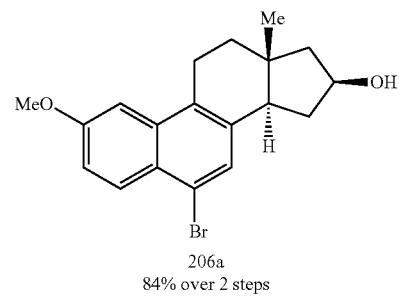

206a
84% over 2 steps

Synthesis of steroid 206a: To a solution of steroid 201a (800 mg, 2.21 mmol) in THF (6 mL) was subsequently added formic acid (0.167 mL, 4.43 mmol), PPh$_3$ (1.162 g, 4.43 mmol) and DIAD (0.872 mL, 4.43 mmol) (dropwise) at 0° C. The reaction mixture was stirred for about 10 mins at 0° C., and then warmed to room temperature. It was continued to stir at room temperature for about an hour. The resulting solution was concentrated in vacuo to afford the crude intermediate, which was purified by flash column chromatography on silica gel with 90:10 to 70:30 hexanes-ethyl acetate gradient elution to afford the intermediate as a yellow oil.

To a solution of the intermediate (720 mg, 1.85 mmol) in THF (2 mL) and MeOH (3 mL) was added K$_2$CO$_3$ (513 mg, 3.71 mmol) at room temperature. The reaction mixture was stirred for 2 h and K$_2$CO$_3$ was removed by filtering through a cotton pipet. The resulting solution was then concentrated in vacuo to afford the crude product, which was purified by flash column chromatography on silica gel with 80:20 to 60:40 hexanes-ethyl acetate gradient elution to afford steroid 206a (673 mg, 84% over 2 steps) as a white solid.

Analytical data for 206a:
TLC (SiO$_2$) R$_f$=0.32 (hexanes:ethyl acetate-60:40); [α]$_{589}^T$=+37.071 (c 0.560, CHCl$_3$); $^1$H NMR (600 NMR, CDCl$_3$) δ 8.16-8.10 (m, 1H), 7.36 (s, 1H), 7.21-7.16 (m, 2H), 4.68 (qd, J=6.5, 5.7, 2.8 Hz, 1H), 3.94 (s, 3H), 3.21-3.05 (m, 2H), 2.81-2.69 (m, 2H), 2.13 (ddd, J=12.7, 6.6, 2.4 Hz, 1H), 1.88-1.71 (m, 4H), 0.91 (s, 3H); $^{13}$C NMR (150 MHZ, CDCl$_3$) δ 158.17, 137.63, 134.59, 129.46, 129.45, 126.49, 125.79, 120.49, 118.08, 102.26, 72.42, 55.36, 49.90, 49.36, 40.01, 37.02, 35.99, 24.57, 18.05; IR (thin film, cm$^{-1}$) 3410, 2946, 2920, 2858, 2848, 1623, 1464, 1451, 1428, 1373, 1343, 1272, 1227, 1032; HRMS (ESI-TOF) m/z: [M+H] Calculated for C$_{19}$H$_{22}$O$_2$Br 361.0803; Found 361.0818.

3H. Steroid 206b

This Example describes the production of steroid 206b.

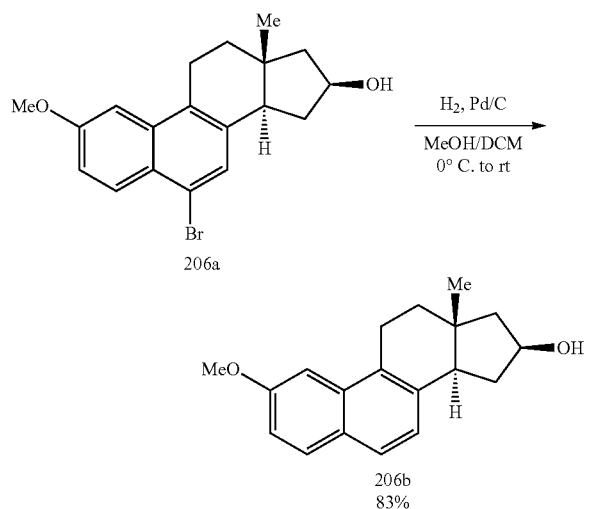

Synthesis of steroid 206b: To a stirring mixture of steroid 206a (17 mg, 0.055 mmol) in 2 mL of anhydrous toluene under nitrogen atmosphere was added t-BuLi (1.58 M in toluene, 87 µL, 0.138 mmol) dropwise at 0° C. The reaction mixture was stirred for an hour at 0° C. and warmed to room temperature. It was continued to stir at room temperature for an hour until it was quenched with DI water. The aqueous layer was separated from the organic layer and extracted with ethyl acetate. The combined organic layers were dried over anhydrous $Na_2SO_4$, and the resulting mixture was vacuum filtered through a coarse fritted glass funnel. The filtrate was concentrated in vacuo to afford the crude product, which was purified by flash column chromatography on silica gel with 80:20 to 60:40 hexanes-ethyl acetate gradient elution to afford 206b (13 mg, 83%) as a white solid.

Analytical data for 206b:

TLC ($SiO_2$) $R_f$=0.33 (hexanes:ethyl acetate-60:40); $[\alpha]_{589}^T$=(c xxx, $CHCl_3$) In progress; $^1$H NMR (600 NMR, $CDCl_3$) δ 7.72 (d, J=8.8 Hz, 1H), 7.61 (d, J=8.3 Hz, 1H), 7.20 (d, J=2.5 Hz, 1H), 7.15-7.03 (m, 2H), 4.75-4.63 (m, 1H), 3.94 (s, 3H), 3.26-3.11 (m, 2H), 2.89-2.74 (m, 2H), 2.14 (m, 1H), 1.92-1.82 (m, 1H), 1.83-1.70 (m, 3H), 0.96-0.88 (m, 3H)); $^{13}$C NMR (150 MHz, $CDCl_3$) δ 157.70, 136.52, 133.08, 130.12, 129.31, 127.46, 125.79, 122.57, 116.95, 101.87, 72.61, 55.26, 50.10, 49.62, 40.03, 37.14, 37.03, 36.21, 24.53, 18.12; IR (thin film, $cm^{-1}$) 3295, 3050, 3002, 2955, 2941, 2917, 2892, 2871, 2838, 2824, 1621, 1430, 1415, 1335, 1307, 1153, 1134, 1029, 835, 754, 720, 701; HRMS (ESI-TOF) m/z: [M+H] Calculated for $C_{19}H_{23}O_2$ 283.1698; Found 283.1688.

3I. Steroid 206c

This Example describes the production of steroid 206c.

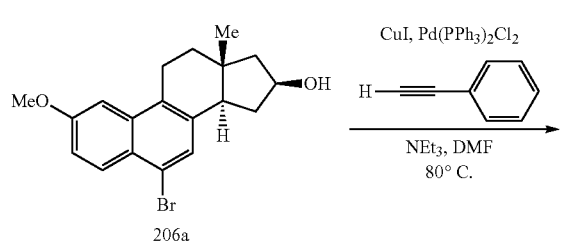

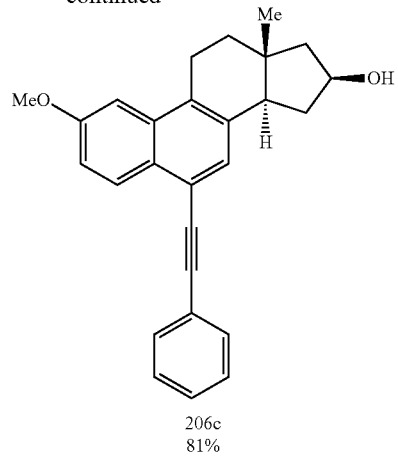

Synthesis of steroid 206c: To a Schlenk tube containing 206a (20 mg, 0.0553 mmol), $Pd(PPh_3)_2Cl_2$ (1.94 mg, 0.0027 mmol) and CuI (1.05 mg, 0.00553 mmol) under nitrogen atmosphere at room temperature was added anhydrous triethylamine (15 µL, 0.1107 mmol) and anhydrous DMF (2 mL) followed by phenylacetylene (12 µL, 0.1107 mmol). The reaction mixture was stirred at 80° C. overnight (approximately 15 h). The resulting mixture was concentrated in vacuo, and DMF was removed by dissolving the mixture in diethyl ether and extracting with water. The organic layer was then concentrated in vacuo to afford the crude product, which was purified by flash column chromatography on silica gel with 70:30 to 60:40 hexanes-ethyl acetate to afford steroid 206c (15.3 mg, 81%) as a yellow solid.

Analytical data for 206c:

TLC ($SiO_2$) $R_f$=0.30 (hexanes:ethyl acetate-60:40); $[\alpha]_{589}^T$=+15.556 (c 0.295, $CHCl_3$); $^1$H NMR (600 NMR, $CDCl_3$) δ 8.35 (d, J=9.2 Hz, 1H), 7.64 (dd, J=8.1, 1.4 Hz, 2H), 7.50-7.27 (m, 4H), 7.21 (d, J=8.6 Hz, 2H), 4.69 (t, J=7.6 Hz, 1H), 3.95 (s, 3H), 3.22 (m, 2H), 2.91-2.71 (m, 2H), 2.15 (ddd, J=12.6, 6.6, 2.0 Hz, 1H), 1.95-1.81 (m, 2H), 1.81-1.69 (m, 2H), 1.65 br (s, 1H), 0.92 (s, 3H); $^{13}$C NMR (150 MHz, $CDCl_3$) δ 158.02, 136.34, 133.12, 131.61, 130.96, 128.48, 128.40, 128.20, 127.23, 127.06, 123.59, 118.51, 117.62, 102.27, 93.44, 88.16, 72.55, 55.30, 50.00, 49.41, 39.98, 37.12, 36.10, 24.75, 18.10; IR (thin film, $cm^{-1}$) 3477, 3059, 2979, 2952, 2935, 2904, 2853, 1770, 1759, 1747, 1718, 1685, 1663, 1636, 1618, 1581, 1455, 1429, 1418, 1373, 1337, 1301, 1268, 1048, 1027, 821, 762, 690; HRMS (ESI-TOF) m/z: [M+H] Calculated for $C_{27}H_{27}O_2$ 383.2011; Found 383.2023.

3J. Steroid 207a

This Example describes the production of steroid 207a used in subsequent reactions.

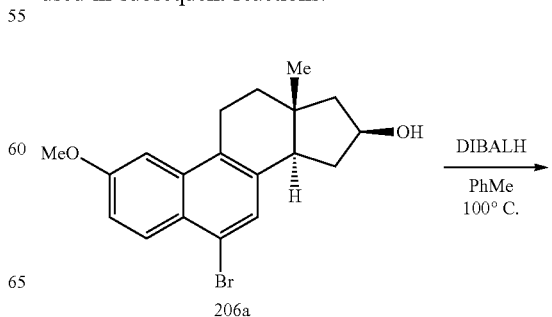

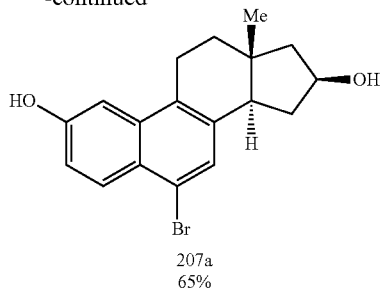

207a
65%

Synthesis of steroid 207a: To a solution of steroid 206a (80 mg, 0.221 mmol) in anhydrous toluene (2.2 mL) was added DIBALH (1.0 M in toluene, 2.2 mL, 2.21 mmol). The reaction mixture was refluxed at 100° C. overnight (approximately 15 h). After the resulting solution was cooled to room temperature, it was quenched by the careful addition of Rochelle's salt and stirred for about 30 mins. The aqueous layer was then separated from the organic layer and extracted with ethyl acetate (×3). The combined organic layers were dried over anhydrous $Na_2SO_4$, and the resulting mixture was vacuum filtered through a coarse fritted glass funnel. The filtrate was concentrated in vacuo to afford the crude product, which was purified by flash column chromatography on silica gel with 70:30 to 50:50 hexanes-ethyl acetate gradient elution to afford 207a (50 mg, 65%) as a white solid.

Analytical data for 207a:
TLC ($SiO_2$) $R_f$=0.22 (hexanes:ethyl acetate-60:40); $[\alpha]_{589}^T$=−885.25 (c 0.105, $(CD_3)_2SO$); $^1H$ NMR (600 NMR, $CDCl_3$) δ 10.00 (s, 1H), 7.95 (d, J=9.0 Hz, 1H), 7.23 (s, 1H), 7.19 (d, J=2.2 Hz, 1H), 7.15 (dd, J=9.1, 2.3 Hz, 1H), 4.75 (s, 1H), 4.41 (t, J=7.2 Hz, 1H), 2.96 (m, 2H), 2.68-2.54 (m, 2H), 2.03-1.91 (m, 1H), 1.64 (m, 2H), 1.56 (d, J=12.7 Hz, 1H), 1.51 (m, 1H), 0.77 (s, 3H); $^{13}C$ NMR (150 MHz, $CDCl_3$) δ 156.69, 138.14, 135.16, 129.28, 129.15, 125.76, 124.46, 120.04, 119.08, 105.76, 70.54, 49.87, 48.84, 36.96, 35.85, 24.42, 18.21; IR (thin film, $cm^{-1}$) 3388, 2953, 2926, 2858, 1728, 1698, 1659, 1623, 1587, 1465, 1430, 1369, 1161, 1132, 1024, 984, 888, 860, 833, 814; HRMS (ESI-TOF) m/z: Sample was sent out, but the mass did not match.

3K. Steroid 207b
This Example describes the production of steroid 207b.

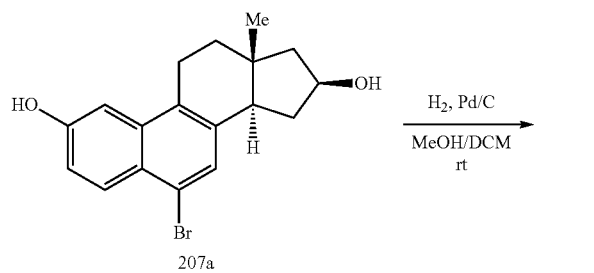

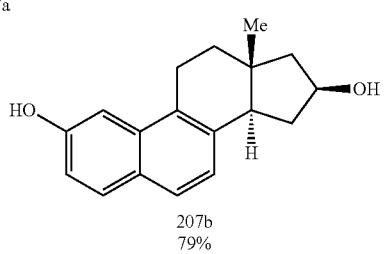

207b
79%

Synthesis of steroid 207b: To a stirring mixture of steroid 207a (20 mg, 0.0576 mmol) in 1 mL MeOH and 0.25 mL DCM under nitrogen atmosphere was added 10% Pd/C (6.1 mg, 0.0058 mmol) at room temperature. A balloon was used to introduce an atmosphere of hydrogen gas into the flask (allowing first for exchange of the nitrogen atmosphere), and the reaction was stirred under a slightly positive pressure of hydrogen for approximately 8 h. The mixture was filtered through a cotton pipet and rinsed with DCM. The resulting solution was concentrated in vacuo to afford the crude product, which was purified by flash column chromatography on silica gel with 65:35 hexanes-ethyl acetate to afford steroid 207b (12.2 mg, 79%) as a white solid.

Analytical data for 207b:
TLC ($SiO_2$) $R_f$=0.23 (hexanes:ethyl acetate-60:40); $[\alpha]_{589}^T$=+36.368 (c 0.310, $CD_3OD$); $^1H$ NMR (600 NMR, $CD_3OD$) δ 7.56 (d, J=8.8 Hz, 1H), 7.45 (d, J=8.3 Hz, 1H), 7.12 (d, J=2.2 Hz, 1H), 6.99-6.82 (m, 2H), 4.50 (q, J=6.6, 6.0 Hz, 1H), 3.02 (m, 2H), 2.74-2.57 (m, 2H), 2.00 (ddd, J=12.5, 6.3, 2.4 Hz, 1H), 1.72 (dd, J=13.2, 8.6 Hz, 1H), 1.69-1.58 (m, 3H), 0.78 (s, 3H); $^{13}C$ NMR (150 MHz, $CD_3OD$) δ 155.03, 136.11, 133.48, 129.71, 128.23, 127.05, 125.48, 121.42, 116.25, 104.42, 71.46, 49.06, 49.01, 39.63, 36.31, 36.06, 23.97, 16.97; IR (thin film, $cm^{-1}$) 3404, 3040, 2950, 2915, 2870, 2855, 1656, 1638, 1623, 1434, 1367, 1329, 1135, 1027, 835; HRMS (ESI-TOF) m/z: [M+H] Calculated for $C_{18}H_{21}O_2$ 269.1542; Found 269.1553.

3L. Steroid 207c
This Example describes the production of steroid 207c.

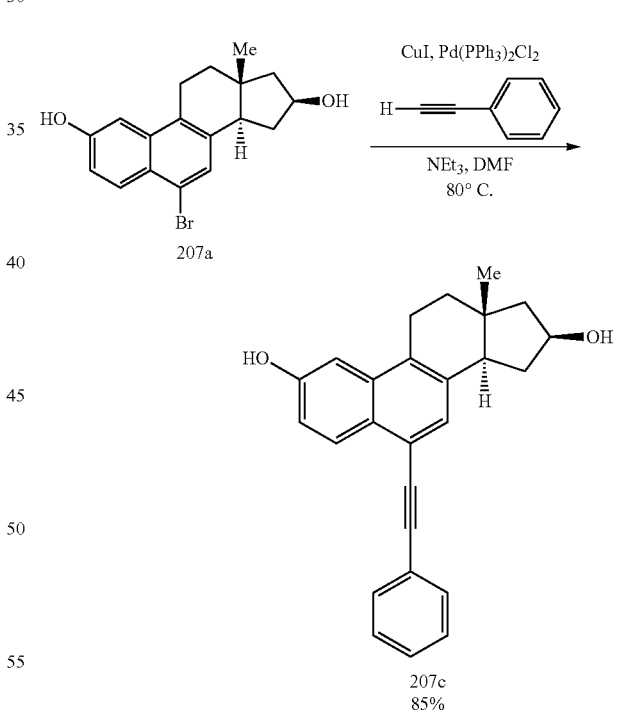

207c
85%

Synthesis of steroid 207c: To a Schlenk tube containing 207a (20 mg, 0.058 mmol), $Pd(PPh_3)_2Cl_2$ (2.03 mg, 0.0029 mmol) and CuI (1.1 mg, 0.0058 mmol) under nitrogen atmosphere at room temperature was added anhydrous triethylamine (16 μL, 0.1152 mmol) and anhydrous DMF (2 mL) followed by phenylacetylene (12 μL, 0.1152 mmol). The reaction mixture was stirred at 80° C. overnight (approximately 15 h). The resulting mixture was concentrated in vacuo, and DMF was removed by dissolving the mixture in diethyl ether and extracting with water. The organic layer was then concentrated in vacuo to afford the crude product, which was purified by flash column chromatography on silica gel with 65:35 hexanes-ethyl acetate to afford steroid 207c (18.3 mg, 85%) as a yellow solid.

Analytical data for 207c:
TLC (SiO$_2$) R$_f$=0.24 (hexanes:ethyl acetate-60:40); [α]$_{589}^T$=(c 0.145, (CH$_3$)$_3$CO); $^1$H NMR (600 NMR, (CD$_3$)$_2$SO) δ 9.88 (d, J=1.5 Hz, 1H), 8.19 (d, J=8.9 Hz, 1H), 7.67 (d, J=7.3 Hz, 2H), 7.54-7.35 (m, 3H), 7.25 (s, 1H), 7.22 (s, 1H), 7.16 (dd, J=8.9, 2.4 Hz, 1H), 4.76 (dd, J=4.0, 1.9 Hz, 1H), 4.53-4.40 (m, 1H), 3.15-2.97 (m, 2H), 2.75-2.63 (m, 2H), 2.03 (dd, J=12.4, 7.4 Hz, 1H), 1.77-1.65 (m, 2H), 1.65-1.51 (m, 2H), 0.80 (s, 3H); $^{13}$C NMR (150 MHz, CDCl$_3$) δ; IR (thin film, cm$^{-1}$) 3415, 3226, 1669, 1641, 1623; HRMS (ESI-TOF) m/z: [M+H] Calculated for C$_{26}$H$_{25}$O$_2$ 369.1855; Found 369.1837.

3M. Steroid 208a

This Example describes the production of steroid 208a.

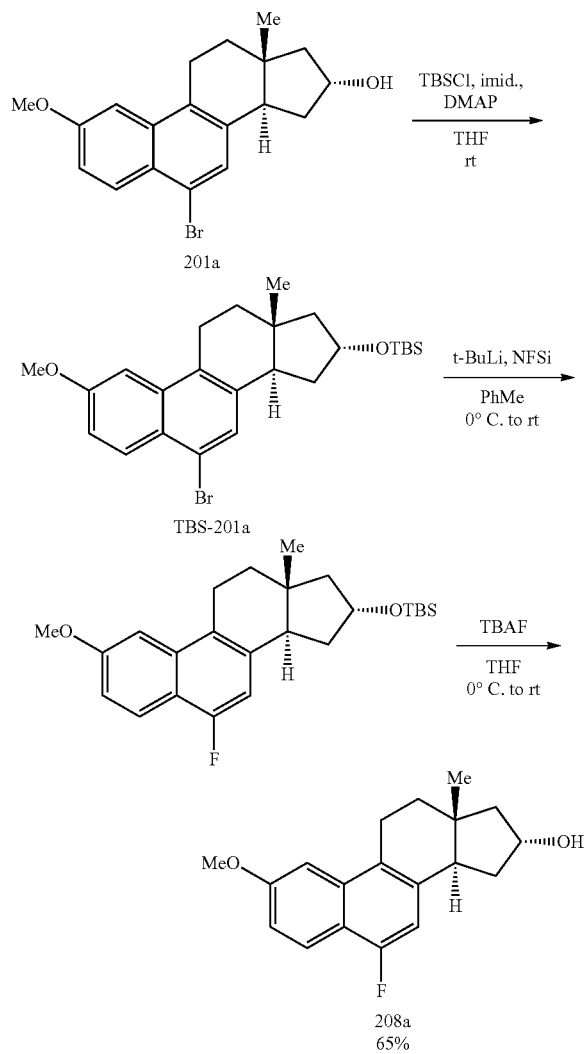

Synthesis of steroid 208a: See Zajc, B. J. Org. Chem. 1999, 64, 1902-1907. To a stirring solution of TBS-protected 201a (50 mg, 0.105 mmol) in anhydrous toluene (2.3 mL) at 0° C. was added t-BuLi (1.58 M in toluene, 0.12 mL, 0.21 mmol). After the reaction mixture was stirred for about an hour at 0° C., NFSi (66 mg, 0.21 mmol) in toluene (1.3 mL) was added to the flask. The ice bath was removed after the addition of NFSi, and the resulting mixture was stirred for 2 hours at room temperature. The reaction mixture was quenched with saturated aqueous NH$_4$Cl, and the aqueous layer was separated from the organic layer and extracted with ethyl acetate (×3). The combined organic layers were dried over anhydrous Na$_2$SO$_4$, and the resulting mixture was vacuum filtered through a coarse fritted glass funnel. The filtrate was concentrated in vacuo to afford the crude product.

To a solution of the above product (17 mg, 0.041 mmol) in anhydrous THF (2 mL) was added TBAF (13 µL, 0.045 mmol) at 0° C. The mixture was stirred for an hour at 0° C., warmed up to room temperature and stirred at room temperature for 2 h. It was quenched with saturated aqueous NH$_4$Cl, and the aqueous layer was separated from the organic layer and extracted with diethyl ether (×3). The combined organic layers were dried over anhydrous Na$_2$SO$_4$, and the resulting mixture was vacuum filtered through a coarse fritted glass funnel. The filtrate was concentrated in vacuo to afford the crude product, which was purified by flash column chromatography on silica gel with 70:30 to 50:50 hexanes-ethyl acetate gradient elution to afford 208a (8 mg, 65%) as a white solid.

Analytical data for 208a:
TLC (SiO$_2$) R$_f$=0.28 (hexanes:ethyl acetate-65:35); [α]$_{589}^T$=(c xxx, CHCl$_3$) In progress; $^1$H NMR (600 NMR, CDCl$_3$) δ 7.99 (d, J=8.9 Hz, 1H), 7.18-7.09 (m, 2H), 6.74 (d, J=11.1 Hz, 1H), 4.78-4.63 (m, 1H), 3.93 (s, 3H), 3.26-3.02 (m, 3H), 2.31 (dd, J=12.5, 7.3 Hz, 1H), 2.20-2.09 (m, 3H), 1.91 (td, J=11.8, 7.8 Hz, 1H), 1.47-1.40 (m, 1H), 0.66 (s, 3H); $^{13}$C NMR (150 MHz, CDCl$_3$) δ In progress; IR (thin film, cm$^{-1}$) In progress; HRMS (ESI-TOF) m/z: [M+H] Calculated for C$_{19}$H$_{22}$O$_2$F 301.1604; Found 301.1615.

3N. Steroid 208b

This Example describes the production of steroid 208b.

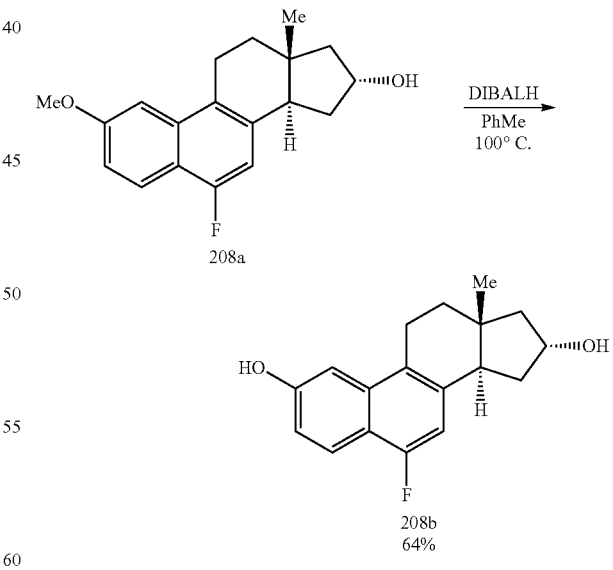

Synthesis of steroid 208b: To a solution of 208a (30 mg, 0.0998 mmol) in anhydrous toluene (1 mL) at room temperature was added DIBALH (1.0 M in toluene, 0.998 mL, 0.998 mmol). The reaction mixture was refluxed at 100° C. overnight (approximately 15 h). After the resulting solution was cooled to room temperature, it was quenched by the careful addition of Rochelle's salt and stirred for about 30 mins. The aqueous layer was then separated from the organic layer and extracted with ethyl acetate (×3). The combined organic layers were dried over anhydrous $Na_2SO_4$, and the resulting mixture was vacuum filtered through a coarse fritted glass funnel. The filtrate was concentrated in vacuo to afford the crude product, which was purified by flash column chromatography on silica gel with 70:30 to 50:50 hexanes-ethyl acetate gradient elution to afford 208b (18 mg, 64%) as a yellow oil.

Analytical data for 208b:
TLC ($SiO_2$) $R_f$=0.21 (hexanes:ethyl acetate-60:40); $[\alpha]_{589}^T$=(c xxx, $CD_3OD$) In progress; $^1H$ NMR (600 NMR, $CDCl_3$) δ 7.79 (d, J=8.9 Hz, 1H), 7.10 (t, J=2.1 Hz, 1H) 6.97 (dd, J=9.0, 2.3 Hz, 1H), 6.57 (d, J=11.4 Hz, 1H), 4.56-4.44 (m, 1H), 3.09-2.85 (m, 3H), 2.13 (dd, J=12.4, 7.3 Hz, 1H), 2.08-1.94 (m, 3H), 1.76 (td, J=11.8, 7.9 Hz, 1H), 1.31 (dd, J=12.4, 5.8 Hz, 1H), 0.54 (s, 3H); $^{13}C$ NMR (150 MHz, $CDCl_3$) δ In progress; IR (thin film, $cm^{-1}$) In progress; HRMS (ESI-TOF) m/z: [M+H] Calculated for $C_{18}H_{20}O_2F$ 287.1447; Found 287.1447.

3O. Steroid 208c

This Example describes the production of steroid 208c.

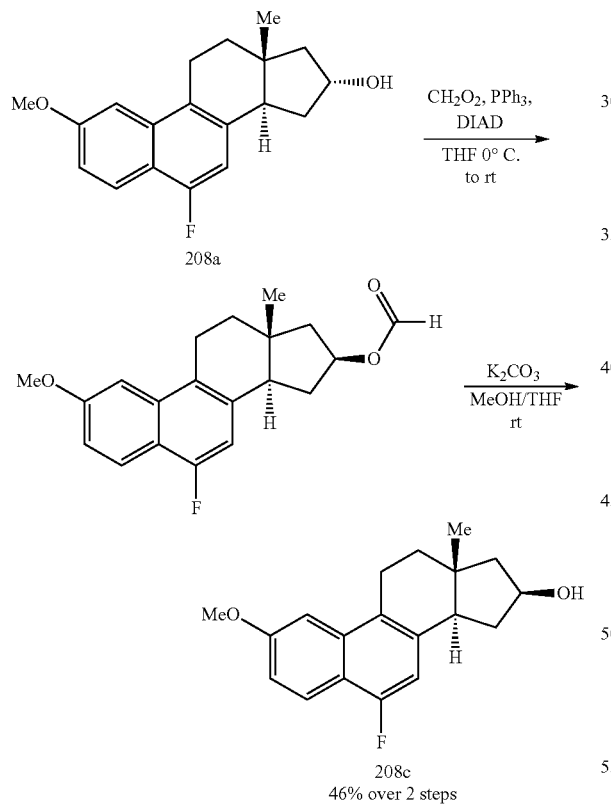

208c
46% over 2 steps

Synthesis of steroid 208c: To a solution of steroid 208a (117 mg, 0.3895 mmol) in THF (4 mL) was subsequently added formic acid (29 μL, 0.779 mmol), $PPh_3$ (204 mg, 0.779 mmol) and DIAD (0.15 mL, 0.779 mmol) (dropwise) at 0° C. The reaction mixture was stirred for about 10 mins at 0° C., and then warmed to room temperature. It was continued to stir at room temperature for about an hour. The resulting solution was concentrated in vacuo to afford the crude intermediate, which was purified by flash column chromatography on silica gel with 95:5 to 90:10 hexanes-ethyl acetate gradient elution to afford the intermediate as a yellow oil.

To a solution of the intermediate (100 mg, 0.305 mmol) in THF (2 mL) and MeOH (3 mL) was added $K_2CO_3$ (84 mg, 0.609 mmol) at room temperature. The reaction mixture was stirred for 2 h and $K_2CO_3$ was removed by filtering through a cotton pipet. The resulting solution was then concentrated in vacuo to afford the crude product, which was purified by flash column chromatography on silica gel with 80:20 to 60:40 hexanes-ethyl acetate gradient elution to afford steroid 208c (53.5 mg, 46% over 2 steps) as a white solid.

Analytical data for 208c:
TLC ($SiO_2$) $R_f$=0.25 (hexanes:ethyl acetate-60:40); $[\alpha]_{589}^T$=(c xxx, $CHCl_3$) In progress; $^1H$ NMR (600 NMR, $CDCl_3$) δ 7.99 (d, J=9.0 Hz, 1H), 7.18-7.12 (m, 2H), 6.76 (d, J=11.2 Hz, 1H), 4.68 (q, J=7.4 Hz, 1H), 3.94 (s, 3H), 3.26-3.05 (m, 2H), 2.84-2.77 (m, 1H), 2.74 (dt, J=12.1, 7.3 Hz, 1H), 2.13 (ddd, J=12.7, 6.8, 2.3 Hz, 1H), 1.86 (dd, J=13.5, 8.3 Hz, 1H), 1.82-1.69 (m, 3H), 0.91 (s, 3H); $^{13}C$ NMR (150 MHz, $CDCl_3$) δ In progress; IR (thin film, $cm^{-1}$) In progress; HRMS (ESI-TOF) m/z: [M+H] Calculated for $C_{19}H_{22}O_2F$ 301.1604; Found 301.1606.

3P. Steroid 209

This Example describes the production of steroid 209 used in subsequent reactions.

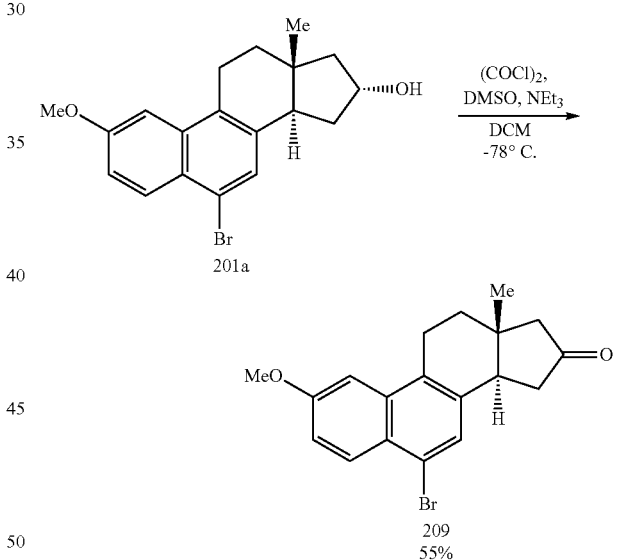

209
55%

Synthesis of steroid 209: To a stirring solution of DMSO (0.45 mL) and DCM (20 mL) at −78° C. was added oxalyl chloride (0.27 mL, 2.17 mmol). The solution was stirred for about 5 mins, and steroid 201a (954 mg, 2.64 mmol) in DCM (20 mL) was added. The reaction mixture was stirred at −78° C. for 2 hr and quenched with saturated aqueous $NaHCO_3$. The aqueous layer was separated from the organic layer and extracted with ethyl acetate (×3). The combined organic layers were dried over anhydrous $MgSO_4$, and the resulting mixture was vacuum filtered through a coarse fritted glass funnel. The filtrate was concentrated in vacuo to afford the crude product, which was purified by flash column chromatography on silica gel with 80:20 hexanes-ethyl acetate to afford steroid 209 (524 mg, 55%) as a yellow solid.

Analytical data for 209:

$^1$H NMR (600 NMR, CDCl$_3$) δ 8.16 (d, J=9.1 Hz, 1H), 7.27 (s, 1H), 7.25-7.18 (m, 2H), 3.96 (s, 3H), 3.38 (dd, J=13.6, 7.7 Hz, 1H), 3.28-3.14 (m, 2H), 2.78 (dd, J=17.7, 7.8 Hz, 1H), 2.49-2.41 (m, 1H), 2.39 (d, J=16.7 Hz, 1H), 2.28 (ddd, J=12.8, 7.3, 1.7 Hz, 1H), 2.23 (d, J=16.9 Hz, 1H), 2.05 (td, J=11.5, 8.3 Hz, 1H), 0.82 (s, 3H)

3Q. Steroid 210

This Example describes the production of steroid 210 used in subsequent reactions.

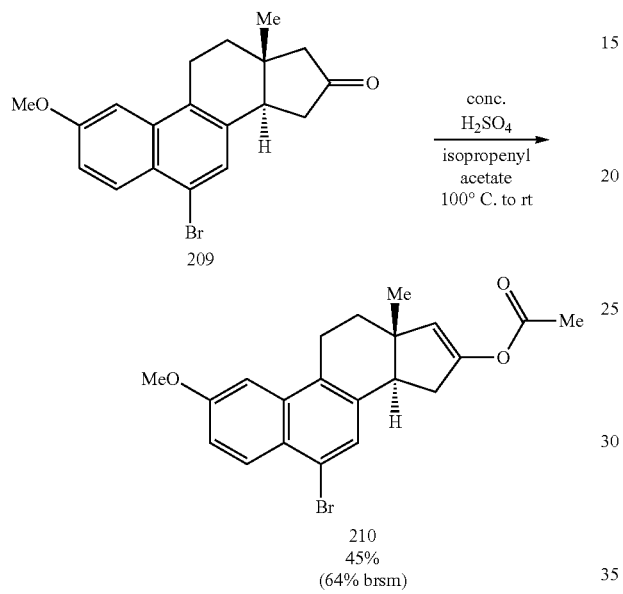

Synthesis of steroid 210: A catalyst solution containing conc. H$_2$SO$_4$ (0.1 mL) and isopropenyl acetate (5 mL) was prepared and stored under nitrogen. To a solution of 209 (524 mg, 1.508 mmol) in isopropenyl acetate (13 mL) at room temperature was added 0.26 mL of the catalyst solution. The resulting mixture was stirred for 2.5 hr at 100° C., and then cooled to room temperature, at which point another portion of the catalyst solution (0.26 mL) was added. The reaction mixture was then stirred for 2.5 hr at 100° C. and quenched with saturated aqueous NaHCO$_3$. The aqueous layer was separated from the organic layer and extracted with ethyl acetate (×3). The combined organic layers were dried over anhydrous Na$_2$SO$_4$, and the resulting mixture was vacuum filtered through a coarse fritted glass funnel. The filtrate was concentrated in vacuo to afford the crude product, which was purified by flash column chromatography on silica gel with 85:15 hexanes-ethyl acetate to afford steroid 210 (275 mg, 45%, (64% brsm)) as a white solid.

Analytical data for 210:

$^1$H NMR (600 NMR, CDCl$_3$) δ 8.15 (d, J=9.1 Hz, 1H), 7.34 (s, 1H), 7.22-7.13 (m, 2H), 5.72 (s, 1H), 3.94 (s, 3H), 3.40 (dd, J=11.7, 7.2 Hz, 1H), 3.25-3.16 (m, 1H), 3.12 (dd, J=17.9, 8.6 Hz, 1H), 2.88-2.78 (m, 1H), 2.70 (dd, J=14.2, 7.1 Hz, 1H), 2.19 (s, 3H), 2.16-2.10 (m, 1H), 2.11-2.02 (m, 1H), 0.76 (s, 3H)

3R. Steroid 211

This Example describes the production of steroid 211 used in subsequent reactions.

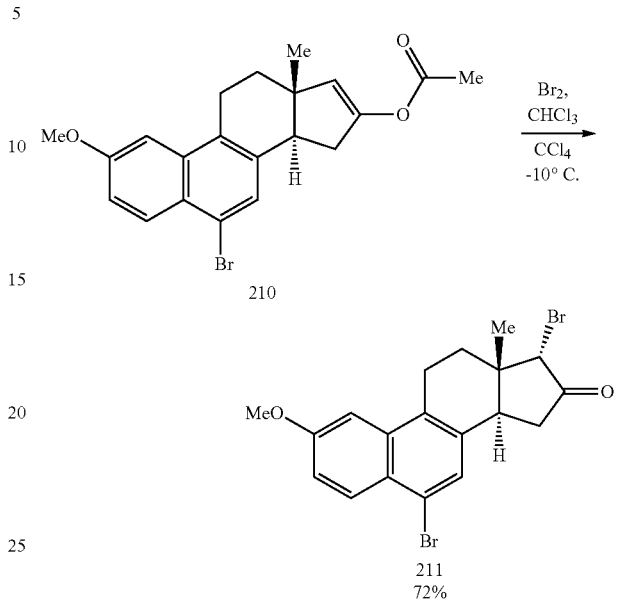

Synthesis of steroid 211: To a solution of 210 (274 mg, 0.683 mmol) in CCl$_4$ (13 mL) was added a solution of Br$_2$ (0.11 mL, 0.683 mmol) in CHCl$_3$ (2.28 mL) at −10° C. The reaction mixture was stirred for 20 mins at −10° C. and quenched with saturated aqueous Na$_2$S$_2$O$_3$. The aqueous layer was separated from the organic layer and extracted with DCM (×3). The combined organic layers were dried over anhydrous Na$_2$SO$_4$, and the resulting mixture was vacuum filtered through a coarse fritted glass funnel. The filtrate was concentrated in vacuo to afford the crude product, which was purified by flash column chromatography on silica gel with 90:10 hexanes-ethyl acetate to afford steroid 211 (214 mg, 72%) as a white solid.

Analytical data for 211:

$^1$H NMR (600 NMR, CDCl$_3$) δ 8.17 (d, J=9.2 Hz, 1H), 7.27 (s, 1H), 7.23 (dd, J=9.2, 2.4 Hz, 1H), 7.20 (d, J=2.5 Hz, 1H), 4.16 (s, 1H), 3.96 (s, 3H), 3.80 (dd, J=12.6, 8.3 Hz, 1H), 3.28 (dd, J=17.8, 7.8 Hz, 1H), 3.20-3.09 (m, 1H), 2.95 (dd, J=18.4, 8.3 Hz, 1H), 2.42 (ddd, J=18.4, 12.6, 1.0 Hz, 1H), 2.34 (td, J=12.0, 7.8 Hz, 1H), 2.10-2.05 (m, 1H), 0.95 (s, 3H)

3S. Steroid 212

This Example describes the production of steroid 212 used in subsequent reactions.

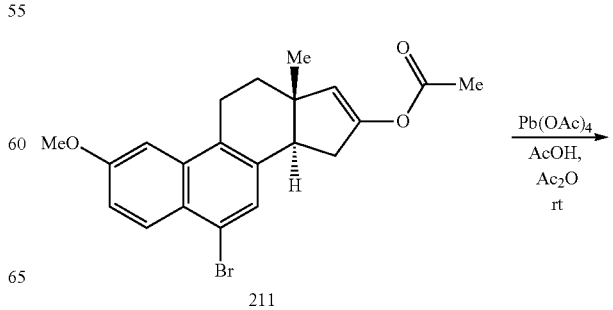

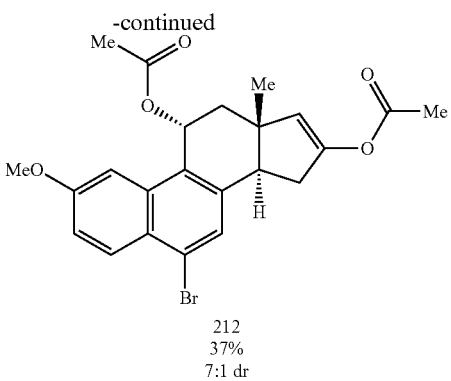

212
37%
7:1 dr

Synthesis of steroid 212: To a solution of 211 (60 mg, 0.186 mmol) in acetic acid (1.5 mL) and acetic anhydride (0.12 mL) was added Pb(OAc)$_4$ (165 mg, 0.372 mmol) at room temperature. After the reaction mixture was stirred for 5 hours, it was quenched with saturated aqueous NaHCO$_3$. The aqueous layer was separated from the organic layer and extracted with ethyl acetate (×3). The combined organic layers were dried over anhydrous Na$_2$SO$_4$, and the resulting mixture was vacuum filtered through a coarse fritted glass funnel. The filtrate was concentrated in vacuo to afford the crude product, which was purified by flash column chromatography on silica gel with 93:7 to 70:30 hexanes-ethyl acetate gradient elution to afford steroid 212 (25 mg, 37%, 7:1 dr) as a white solid.

Analytical data for 212:
$^1$H NMR (600 NMR, CDCl$_3$) δ 8.17 (d, J=8.9 Hz, 1H), 7.40 (s, 1H), 7.19 (dd, J=9.3, 2.4 Hz, 1H), 7.08 (d, J=2.4 Hz, 1H), 6.80 (dd, J=9.0, 5.3 Hz, 1H), 5.68 (d, J=2.0 Hz, 1H), 3.88 (s, 3H), 3.66 (dd, J=11.6, 7.1 Hz, 1H), 2.89-2.78 (m, 2H), 2.77-2.70 (m, 1H), 2.19 (s, 4H), 2.05 (s, 4H), 1.97 (dd, J=13.0, 5.4 Hz, 1H), 0.66 (s, 3H)

Example 4: Further Reactions with Steroids

4A. Non-Aromatic A Ring Formation

This Example describes the production of steroid 37 used in subsequent reactions.

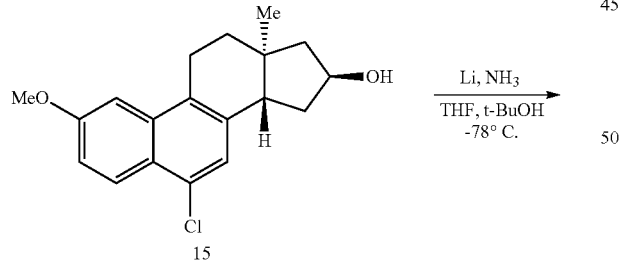

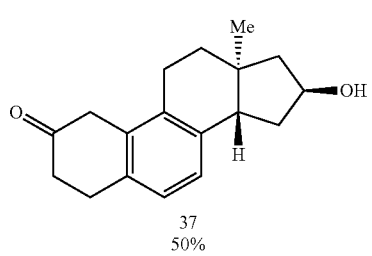

37
50%

Briefly, a solution of steroid 15 (14 mg, 0.044 mmol, 1.0 equiv) and t-BuOH (26 mg, 0.35 mmol, 8.0 equiv) in 1 mL THF followed by lithium metal (31 mg, 4.4 mmol, 100.0 equiv) was added to a Schlenk tube charged with 4 mL liq. NH$_3$ under N$_2$ atmosphere at −78° C. The resulting mixture was stirred at −78° C. for 1 h, and NH$_4$Cl(s) was added. The cooling bath was removed, and the reaction mixture was slowly warmed to rt. 3 mL 3 M HCl (aq) was added to the reaction mixture, stirred for 30 min, and 10 mL ethyl acetate was added. The organic layer was separated, and the aqueous layer was extracted with ethyl acetate (10 mL×3). The combined organic layers were washed with water, sat. NaHCO$_3$ (aq), brine, and then dried over anhydrous MgSO$_4$. The resulting suspension was filtered through a coarse fritted glass funnel, and the filtrate was concentrated in vacuo. Purification of the crude product by flash column chromatography afforded 5.9 mg of compound steroid 37 as a yellow film (50%).

4B. Regioselective Enolization & Formation of Enolacetate 38

This Example describes the production of ketone S21 used in subsequent reactions and the production of the steroidal enolacetate 38.

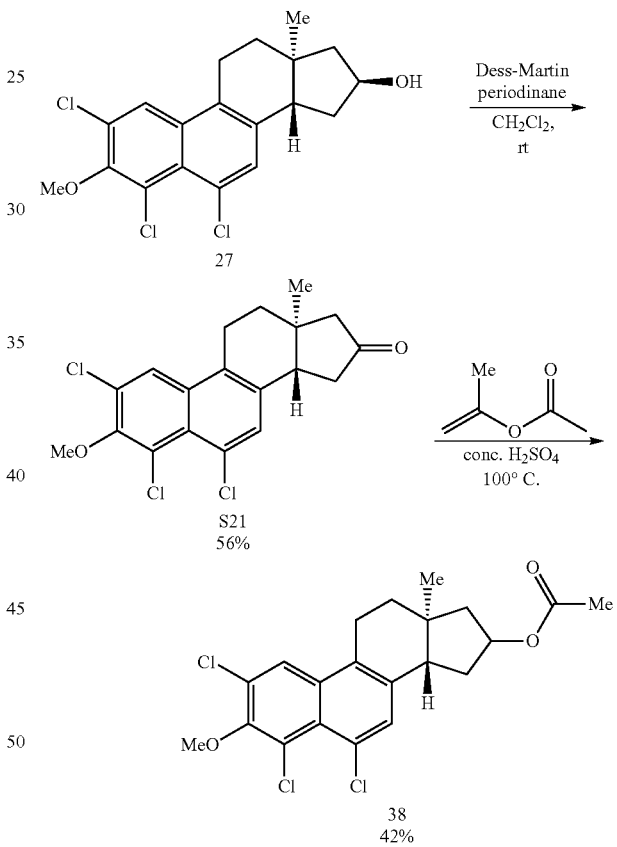

To a stirring solution of steroid 27 (0.13 g, 0.34 mmol, 1.0 equiv) in 3 mL CH$_2$Cl$_2$ was added DMP (0.43 g, 1.0 mmol, 3.0 equiv). The mixture was stirred until the reaction was judged to be complete by TLC analysis, then partitioned between 10 mL of sat. NaHCO$_3$ (aq) and 30 mL CH$_2$Cl$_2$. The organic layer was separated, and the aqueous layer was extracted with CH$_2$Cl$_2$ (50 mL×2). The combined organic layers were dried over anhydrous MgSO$_4$, filtered through a coarse fritted glass funnel, and the filtrate was concentrated in vacuo. Purification of the crude product by flash column chromatography afforded 0.11 g of compound ketone S21 as a colorless film (85%).

To a solution of ketone S21 (0.11 g, 0.29 mmol, 1.0 equiv) in 2.5 mL isopropenyl acetate at rt under N$_2$ atmosphere was added 50 μL of 2% conc. H$_2$SO$_4$ (aq) in isopropenyl acetate. The resulting brown solution was warmed to 100° C. and stirred for 2.5 hr. Then, the solution was cooled to rt and another 50 μL of 2% conc. H$_2$SO$_4$ (aq) in isopropenyl acetate was added. The resulting mixture was further stirred at 100° C. until the reaction was complete based on TLC analysis, then partitioned between 10 mL sat. NaHCO$_3$ (aq) and 20 mL ethyl acetate. The organic layer was separated, and the aqueous layer was extracted with ethyl acetate (20 mL×3). The combined organic layers were dried over anhydrous Na$_2$SO$_4$, filtered through a coarse fritted glass funnel, and the filtrate was concentrated in vacuo. Purification of the crude product by flash column chromatography afforded 51 mg of compound 38 as a white amorphous solid (42%).

4C. B-Ring Functionalization

This Example describes the production of steroid 39 used in subsequent reactions.

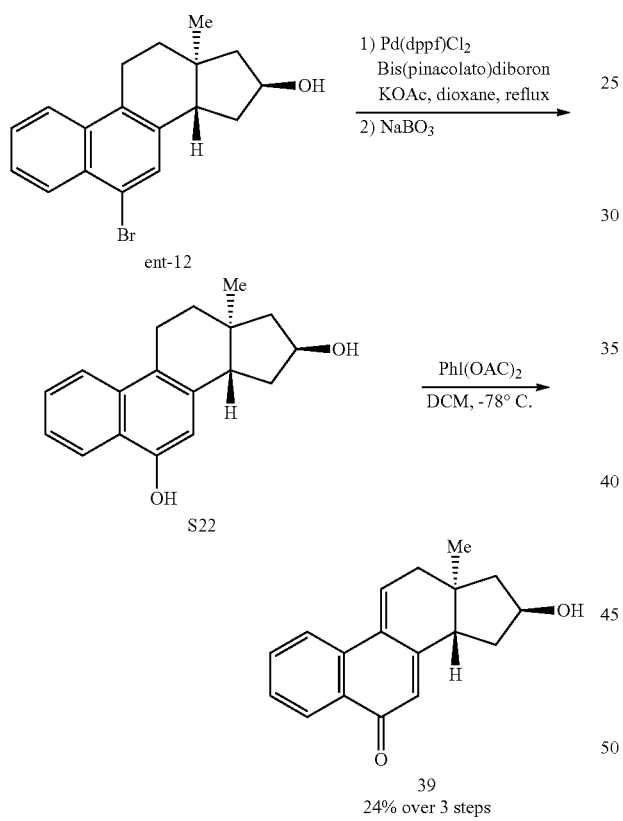

Pd(dppf)Cl$_2$ (5.8 mg, 0.0080 mmol, 0.050 equiv), KOAc (30.0 mg, 0.30 mmol, 2.0 equiv), bis(pinacolato)diboron (46 mg, 0.18 mmol, 1.2 equiv) and ent-12 (50.0 mg, 0.15 mmol, 1.0 equiv) were added to a Schlenk tube equipped with a magnetic stir bar. The reaction vessel was evacuated with vacuum and backfilled with nitrogen 3 times, and then 2 mL dioxane was added. The resulting mixture was warmed to 110° C. and stirred overnight (approx. 12 h). The solution was cooled to rt, and 10 mL ethyl acetate was added. The resulting mixture was passed through a pad of celite, and the filtrate was concentrated in vacuo. Purification of the crude product by flash column chromatography afforded 32 mg of the borated product as a film (56%).

To a solution of the above borated compound (23 mg, 0.061 mmol, 1.0 equiv) in 2 mL THF under N$_2$ atmosphere at rt was added NaBO$_3$·4H$_2$O (18 mg, 0.12 mmol, 2 equiv). The resulting mixture was stirred at rt until the reaction was judged to be complete by TLC analysis, then partitioned between 5 ml sat. NH$_4$Cl (aq) and 5 mL ethyl acetate. The organic layer was separated, and the aqueous layer was extracted with ethyl acetate (5 mL×3). The combined organic layers were washed with water, brine, and dried over anhydrous MgSO$_4$. The resulting suspension was filtered through a coarse fritted glass funnel, and the filtrate was concentrated in vacuo. Purification of the crude product by flash column chromatography afforded 14 mg of compound S22 as a white amorphous solid (86%).

To a solution of steroid S22 (10.0 mg, 0.037 mmol, 1.0 equiv) in 2 mL CH$_2$Cl$_2$ under N$_2$ atmosphere at −78° C. was added a solution of PhI(OAc)$_2$ (17.8 mg, 0.055 mmol, 1.5 equiv) in 0.1 mL CH$_2$Cl$_2$ dropwise. The resulting mixture was stirred for 5 min at −78° C., then partitioned between 4 mL sat. NaHCO$_3$ (aq) and 3 mL CH$_2$Cl$_2$. The organic layer was separated, and the aqueous layer was extracted with CH$_2$Cl$_2$ (5 mL×2). The combined organic layers were washed with brine and dried over anhydrous MgSO$_4$. The resulting suspension was filtered through a coarse fritted glass funnel, and the filtrate was concentrated in vacuo. Purification of the crude product by flash column chromatography afforded 4.9 mg of compound steroid 39 as a film (50%).

4D. Suzuki Coupling at C6

This Example describes the production of steroid 40 used in subsequent reactions.

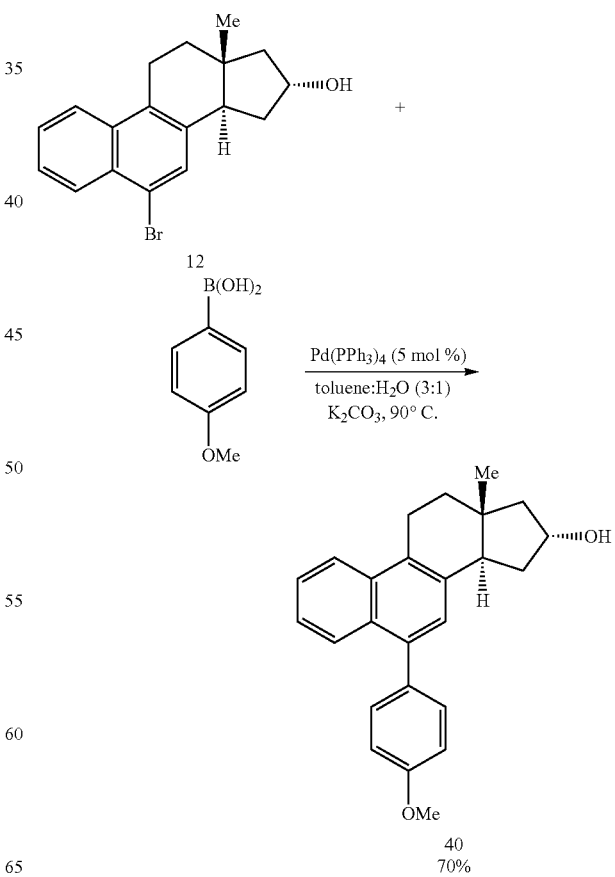

Pd(PPh$_3$)$_4$ (1.7 mg, 0.0015 mmol, 0.05 equiv), K$_2$CO$_3$ (8.2 mg, 0.06 mmol, 2 equiv), 4-methoxyphenylboronic acid (9.2 mg, 0.06 mmol, 2 equiv) and compound steroid 12 (10 mg, 0.03 mmol, 1 equiv) were added to a Schlenk tube equipped with a magnetic stir bar. The reaction vessel was evacuated with vacuum and backfilled with nitrogen 3 times, and then 0.9 mL toluene and 0.3 mL water was added. The resulting mixture was heated to 90° C. and stirred overnight. The reaction mixture was cooled to rt, and (5 mL) ethyl acetate was added. The mixture was filtered through a pad of celite, and the filtrate was concentrated in vacuo. Purification of the crude product by flash column chromatography afforded 7.5 mg of compound steroid 40 as a film (70%).

4E. C11 Oxygenation

This Example describes the production of steroid 41 used in subsequent reactions.

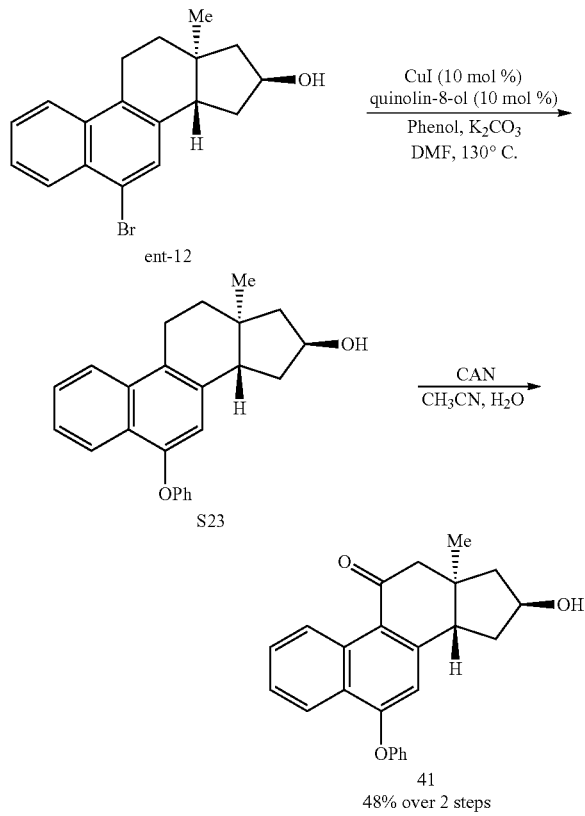

Cul (1.7 mg, 0.009 mmol, 0.1 equiv), quinolin-8-ol (1.3 mg, 0.009 mmol, 0.1 equiv), K$_2$CO$_3$ (25 mg, 0.182 mmol, 2 equiv) and ent-12 (30 mg, 0.091 mmol, 1 equiv) were added to a Schlenk tube equipped with a magnetic stir bar. The reaction vessel was evacuated with vacuum and backfilled with nitrogen 3 times. Phenol (17 mg, 0.182 mmol, 2 equiv) and 1 mL DMF was added, and the resulting mixture was stirred overnight at 130° C. (approx. 12 h). The reaction mixture was cooled to rt, and ethyl acetate (5 mL) was added. The resulting mixture was filtered through a pad of celite, and the filtrate was concentrated in vacuo. Purification of the crude product by flash column chromatography afforded 21 mg of the S23 as a film (68%).

To a solution of S23 (6 mg, 0.02 mmol) in 1 mL CH$_3$CN was added CAN (48 mg, 0.087 mmol, 5.0 equiv) in 0.3 mL DI water at rt. The resulting solution was stirred at rt for 30 min, then partitioned between 5 mL ethyl acetate and 3 mL DI water. The organic layer was separated and the aqueous layer was extracted with ethyl acetate (5 mL×3). The combined organic layers were washed with water, brine, and dried over anhydrous MgSO$_4$. The resulting suspension was filtered through a coarse fritted glass funnel, and the filtrate was concentrated in vacuo. Purification of the crude product by flash column chromatography afforded 4.3 mg of steroid 41 as a film (48% over 2 steps).

Example 5: Multigram-Scale Preparation of Synthetic Steroid ent-12

5A. Steroid ent-12

This Example describes the production of steroid ent-12 used in subsequent reactions.

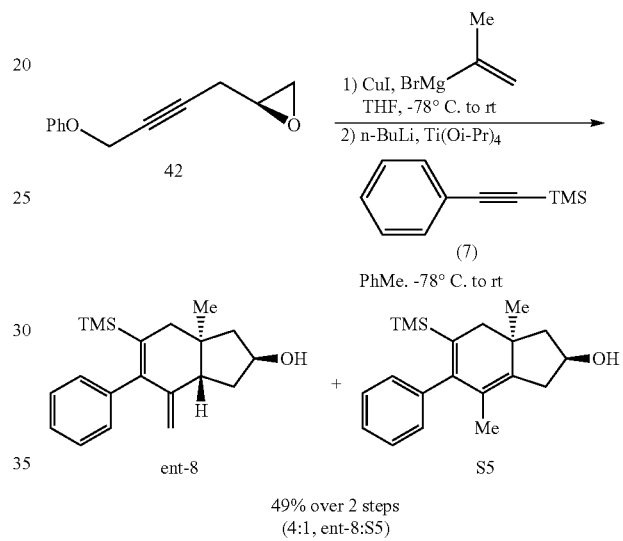

To a stirring solution of epoxide 42 (14.8 g, 0.0786 mol, 1.0 equiv) in 300 mL THF under N$_2$ atmosphere at −78° C. was added CuI (3.0 g, 0.016 mol, 0.2 equiv) followed by isopropenyl magnesium bromide (0.50 M in THF, 0.19 L, 0.094 mol, 1.2 equiv). The resulting yellow suspension was stirred for 1 h at −78° C., warmed to rt, and then stirred until the reaction was judged to be complete by TLC analysis. The reaction was quenched by adding 200 mL sat. NH$_4$Cl (aq) to the reaction mixture. The organic layer was separated, and the aqueous layer was extracted with ethyl acetate (200 mL×3). The combined organic layers were dried over anhydrous MgSO$_4$, filtered through a coarse fritted glass funnel, and the filtrate was concentrated in vacuo. Purification of the crude product by SiO$_2$ flash column chromatography using 20% ethyl acetate: 80% hexanes as the eluent afforded 14.8 g of the enyne ent-6 as a yellow oil (81%).

To a stirring solution of alkyne 7 (30.0 g 0.172 mol, 2.7 equiv) in 1.2 L of dry toluene at rt under N$_2$ atmosphere was added Ti(Oi-Pr)$_4$ (49.1 g, 0.172 mmol 2.7 equiv). The resulting mixture was cooled to −78° C., and n-BuLi (2.7 M in hexanes, 135 mL, 0.364 mol, 5.7 equiv) was added dropwise. The resulting black Ti-alkyne complex was warmed first to rt, then heated to 50° C. and stirred at 50° C. for 1 h (a reflux condenser was not used). In a separate flask under N$_2$ atmosphere, enyne ent-6 (14.7 g, 0.0638 mol, 1.0 equiv) was dissolved in 300 mL of dry toluene, cooled to −78° C., and treated with n-BuLi (2.5 M in hexanes, 25 mL, 0.064 mmol, 1.0 equiv) dropwise at −78° C. The resulting yellow solution was warmed to rt, and then transferred by cannula to the black Ti-alkyne complex at −78° C. The resulting mixture was slowly warmed to rt overnight (approx. 17 h). After this period, 1.5 L of dry MeOH in a separate flask was cooled to −78° C. under $N_2$ atmosphere, and the reaction mixture was transferred by cannula to the pre-cooled MeOH. Once the addition was complete, the reaction mixture was warmed to rt, and 500 mL of DI $H_2O$ was added. The reaction mixture was further diluted with 500 mL ethyl acetate. The organic layer was separated, and the aqueous layer was extracted with ethyl acetate (500 mL×3). The combined organic layers were dried over anhydrous $MgSO_4$, filtered through a coarse fritted glass funnel, and then the filtrate was concentrated in vacuo. Purification of the crude product by flash column chromatography using 25% ethyl acetate: 75% hexanes as the eluent afforded 12.4 g of the compounds steroid ent-8 and S5 as a yellow oil (60%, isolated as a 4:1 mixture of ent-8:S5).

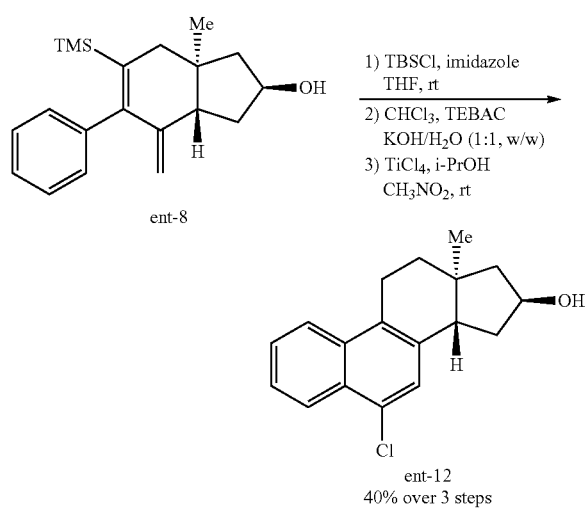

The following three-step procedure was used to convert 9.9 g of the trans-fused hydrindane ent-8 to the steroidal product ent-12 with an overall 40% isolated yield. This yield is based on the amount of hydrindane ent-8 present in a 4:1 mixture with the unreactive "endo" diene isomer S5.

To a solution of 12.4 g of 4:1 mixture of hydrindane ent-8 (9.9 g, 0.030 mol, 1.0 equiv) and its corresponding endo diene isomer S5 (2.5 g, 0.0080 mol) in 500 mL THF was added TBSCl (11.4 g, 0.0756 mol, 2.5 equiv) and imidazole (5.2 g, 0.076 mol, 2.5 equiv). The reaction mixture was stirred at rt under $N_2$ atmosphere overnight (approx. 17 h), then partitioned between 200 mL sat. $NaHCO_3$ (aq) and 200 mL ethyl acetate. The organic layer was separated, and the aqueous layer was extracted with ethyl acetate (200 mL×3). The combined organic layers were washed with brine and dried over anhydrous $MgSO_4$. The resulting suspension was filtered through a coarse fritted glass funnel, and the filtrate was concentrated in vacuo. The crude product was passed through a pad of silica gel using 1% hexanes: 99% ethyl acetate as the eluent to afford 15.8 g of the crude product as a yellow oil. The crude product was used in the next step without further purification.

To a solution of the above crude product (15.8 g) and TEBAC (1.7 g, 7.3 mmol) in 73 mL $CHBr_3$ at rt was added KOH (24.6 g, 0.438 mol) in water (25 mL). The reaction mixture was stirred at 45° C. overnight (approx. 17 h). The reaction mixture was cooled to rt, then partitioned between 100 mL DI water and 200 mL $CH_2Cl_2$. The organic layer was separated, and the aqueous layer was extracted with $CH_2Cl_2$ (200 mL×3). The combined organic layers were washed with brine and dried over anhydrous $MgSO_4$. The resulting suspension was filtered through a coarse fritted glass funnel, and the filtrate was concentrated in vacuo to afford 19.6 g of the crude product as a brown oil. The crude product was used in the next step without further purification.

To a solution of the above crude product (19.6 g) in 600 mL nitromethane was added i-PrOH (20.4 g, 0.34 mol) and $TiCl_4$ (15.9 g, 0.084 mol). The resulting mixture was stirred at rt for 1 h under $N_2$ atmosphere, and a second aliquot of i-PrOH (20.4 g, 0.34 mol) and $TiCl_4$ (15.9 g, 0.084 mol) was added. The mixture was stirred for another 1 h at rt under $N_2$ atmosphere, then partitioned between 200 mL sat. $NaHCO_3$ (aq) and 200 mL $CH_2Cl_2$. The organic layer was separated, and the aqueous layer was extracted with $CH_2Cl_2$ (200 mL×3). The combined organic layers were washed with brine and dried over anhydrous $MgSO_4$. The resulting suspension was filtered through a coarse fritted glass funnel, and the filtrate was concentrated in vacuo. Purification of the crude product by flash column chromatography using 20% ethyl acetate:80% hexanes as the eluent afforded 4.0 g of compound steroid ent-12 as a yellow amorphous solid (40% over 3 steps).

The invention may be embodied in other specific forms without departing from the spirit or essential characteristics thereof. The foregoing embodiments are therefore to be considered in all respects illustrative rather than limiting of the invention described herein.

Example 6: In Vitro Growth Inhibition

Fifteen (15) exemplary compounds were investigated for growth inhibition in two cancer cell lines (one for breast and one for pancreatic cancer: MDA-MB-231 and AsPC-1, respectively).

Procedure: Inhibition of cell growth was accessed by plating 1000 cells per well of a 96-well plate. The following day, compounds were added as 2-fold dilutions from 40 μM (8 wells/concentration). After 6 days, cells were washed, lysed and stained with Hoechst 33258. Fluorescence was read on a microplate spectrofluorometer. Results are expressed as the concentration that inhibited growth by 50% ($GI_{50}$). See Rao, J., Otto, W. R. Fluorometric DNA assay for cell growth estimation. Anal Biochem. 1992; 207:186-192.

| Compound | MDA-MB-231 $GI_{50}$ (μM) | AsPC-1 $GI_{50}$ (μM) |
|---|---|---|
| 205b | 0.8 | 2 |
| 201a | 15 | 15 |
| 201b | 25 | 30 |
| 206a | 20 | 20 |
| 201c | 20 | 30 |
| 206c | 15 | 15 |
| 205c | 8 | 9 |
| 205a | 17 | 10 |
| 208a | 25 | 30 |
| 206b | 30 | 40 |
| 207b | 20 | 40 |
| 207c | 5 | 15 |
| 207a | 30 | 30 |
| 208b | 4 | 8 |
| 208c | 5 | 25 |

Compound 205b has been identified as a uniquely potent and selective agonist of ER-β, having an EC$_{50}$=20 nM for ER-β and an EC$_{50}$ over 3000 nM for ER-α. Compound 205b also has been found to have affinity to CLK-4 (a member of the family of CDC-2-like kinases at ~350 nM. Growth of several cancer cell lines (MDA-MB-231, AsPC-1, and A549) incubated with Compound 205b was inhibited at 0.8-5 μM. Parallel experiments demonstrated that these concentrations arrested cells in G2/M phase of the cell cycle, and microscopic analysis showed the cells arrested in mitosis at prometaphase.

Figure 3D:
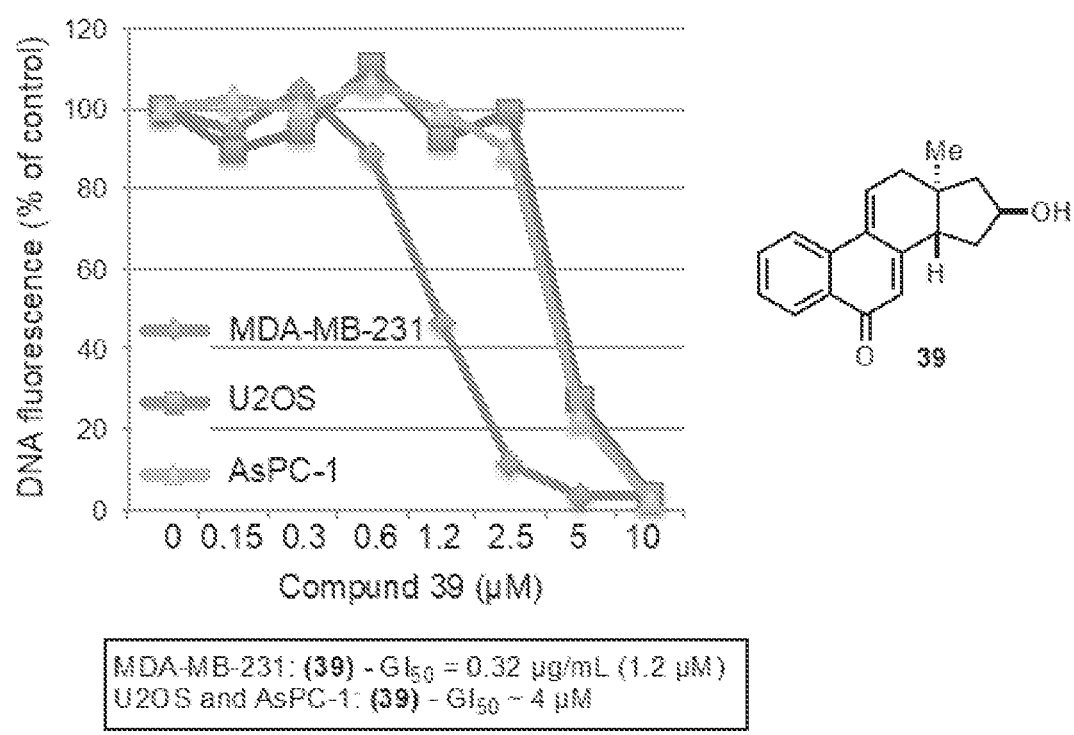
FIG. 3D shows an ent-steroid with cytotoxic properties wherein cells were plated at 1000 cells/well of a 96 well plate. The following day, ent-steroidal compound 39 was added in 2-fold dilutions (8 wells/concentration). After 7 days growth, cells were lysed and analyzed for total DNA content as described in Montano et al. (See, Montano, R., et al., Mol. Cancer Therap., 11:427-438 [2012]).

Compound 39 was also investigated for growth inhibition in three cancer cell lines: MDA-MB-231, AsPC-1, and U2OS (human osteosarcoma). DNA fluorescence as a percent of control for increasing concentrations of Compound 39 are shown in FIG. 3D. The calculated GI$_{50}$ for Compound 39 against MDA-MB-231 was 0.32 ug/mL (1.2 uM) and the calculated GI$_{50}$ for Compound 39 against U2OS and AsPC-1 was ~4 uM.

INCORPORATION BY REFERENCE

The contents of all cited references including literature references as well as all foreign and patents and patent applications that are cited throughout this application are hereby expressly incorporated by reference in their entirety, as are the references cited therein. The present disclosure specifically incorporates U.S. Pat. Publication Nos: 20020132802; 20050054624; 20060009438; 20150250801; 20150259376; 20150361125; 20160326127; and U.S. Pat. Nos. 5,554,601; 5,843,934; 5,877,169; 6,350,739; 6,503,894; 6,680,331; 6,844,456; 7,781,421; 8,759,330; 9,156,876; 9,365,502; 9,388,210; 9,505,743; 9,512,170; 9,562,026; 9,630,986; and 9,676,812, by reference in their entireties.

What is claimed is:

1. A method for making a compound of Formula (G):

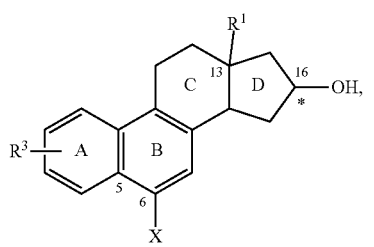

(G)

the method comprising:
forming a B-ring by cyclopropanation and intramolecular Friedel-Crafts alkylation of an intermediate compound of Formula (E) using a compound of CH(X)$_3$

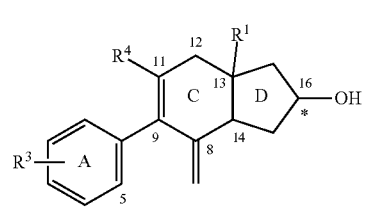

(E)

wherein R$^1$ is C$_1$-C$_4$ alkyl optionally substituted with a C$_6$-C$_{10}$ aryl; R$^3$ is hydrogen, C$_1$-C$_4$ alkyl, halogen, or —O-(C$_1$-C$_4$-alkyl); R$^4$ is trimethylsilyl; and X is halogen.

2. The method of claim 1, wherein the intermediate compound of Formula (E) is formed by reacting a compound of Formula (C) with a compound of Formula (D):

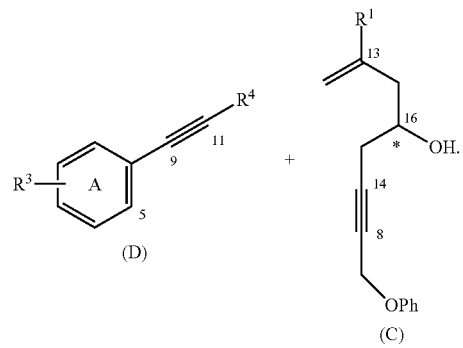

3. The method of claim 2, wherein the compound of Formula (D) is selected from the group consisting of:

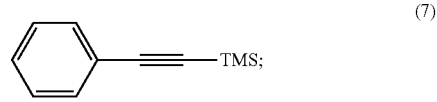
(7)

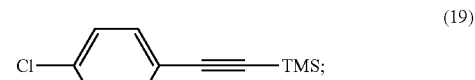
(19)

(13)

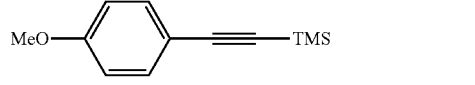
(22)

(16)

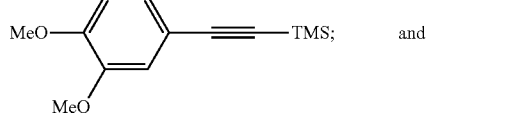
(16) and

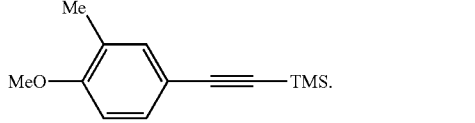
(28)

4. The method of claim 1, wherein R$^1$ is C$_1$-C$_4$ alkyl.
5. The method of claim 1, wherein R$^1$ is methyl, ethyl, or benzyl.
6. The method of claim 1, wherein R$^1$ is methyl.
7. The method of claim 1, wherein R$^1$ is ethyl.
8. The method of claim 1, wherein R$^1$ is benzyl.
9. The method of claim 1, wherein X is Br or Cl.
10. The method of claim 1, wherein R$^3$ is hydrogen, halogen, or methoxy.

11. The method of claim 1, wherein $R^3$ is hydrogen.

12. The method of claim 1, wherein $R^3$ is halogen.

13. The method of claim 1, wherein $R^3$ is methoxy.

14. The method of claim 1, wherein $R^1$ is $C_1$-$C_4$ alkyl or benzyl and $R^3$ is hydrogen, halogen, or methoxy.

15. The method of claim 1, wherein the compound of Formula (G) is selected from the group consisting of:

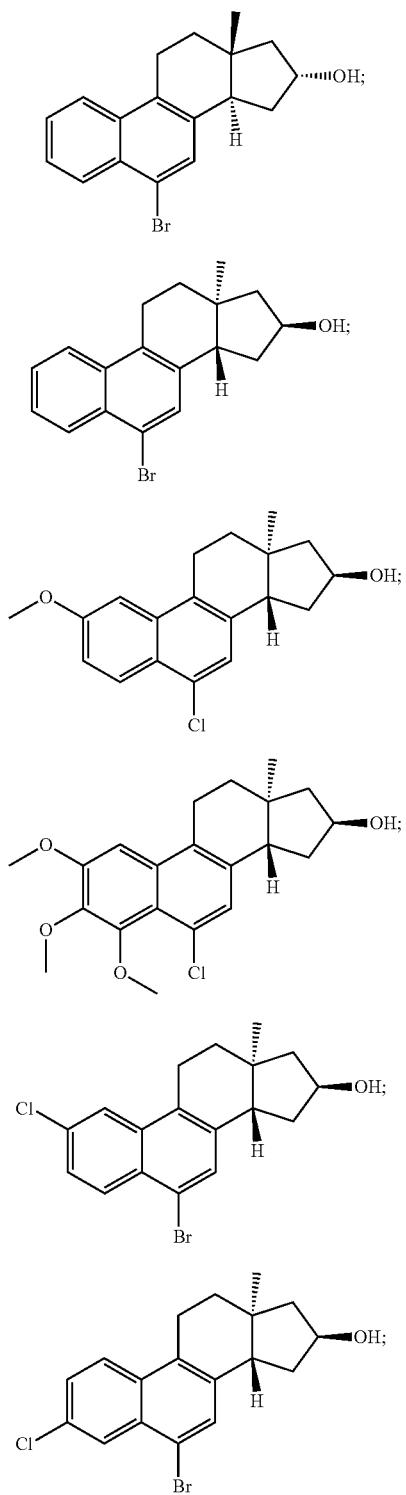

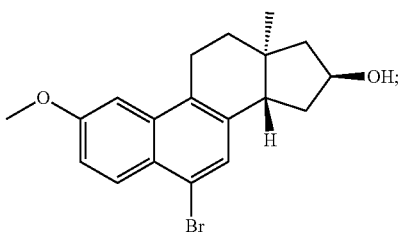

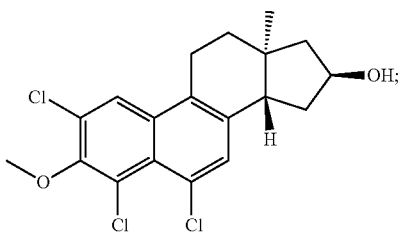

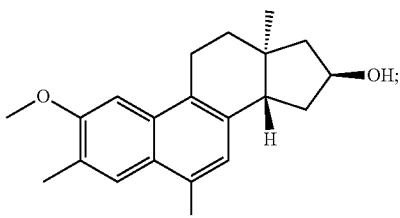

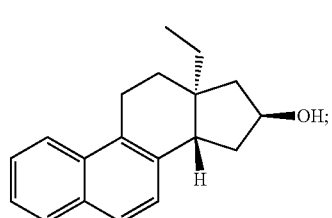

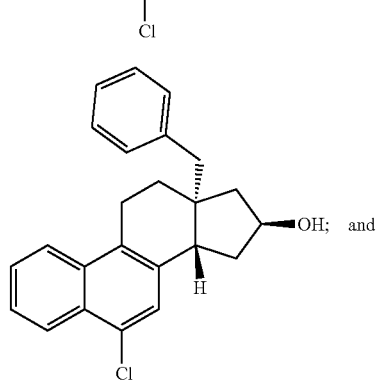

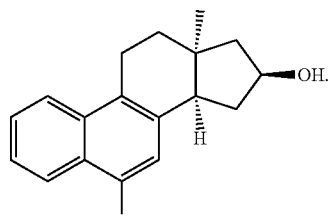

16. The method of claim 1, wherein the intermediate compound of Formula (E) is selected from the group consisting of:

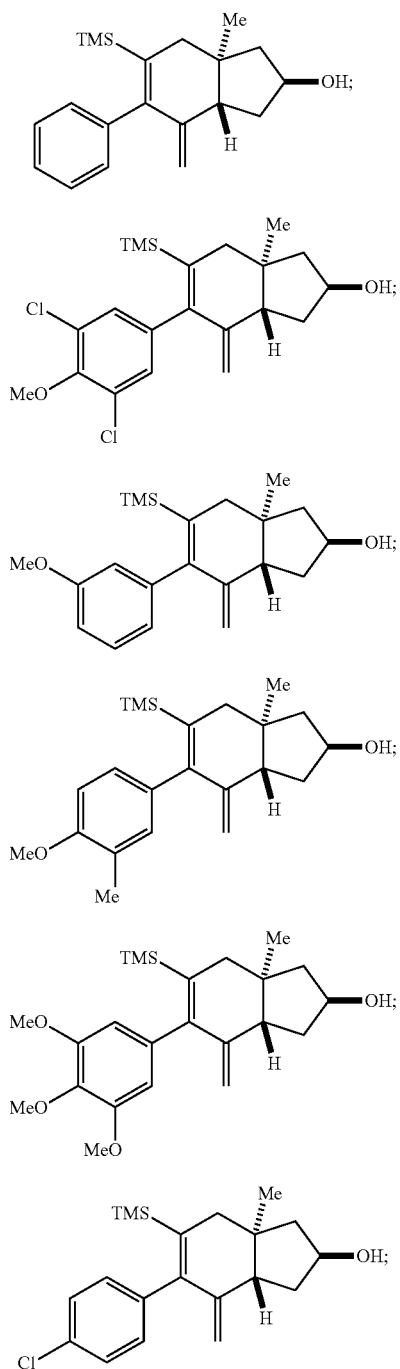

17. The method of claim 1, further comprising a dehalogenation step to remove X from the compound of Formula (G).

18. The method of claim 17, further comprising selective B-ring functionalization at C6 to introduce a substituent selected from the group consisting of —$OR^{BX}$, wherein $R^{BX}$ is $C_{1-6}$-alkyl; $C_{6-10}$-aryl optionally substituted with one or more $C_{1-6}$-alkoxy; and $C_{6-10}$-aryl-$C_{2-6}$-alkynyl.

19. The method of claim 18, wherein the substituent is -OPh.

20. The method of claim 18, wherein the substituent is methoxyphenyl.

21. The method of claim 18, wherein the selective functionalization is by Suzuki coupling or Ullman coupling.

\* \* \* \* \*